(12) United States Patent
Mihara et al.

(10) Patent No.: US 8,372,867 B2
(45) Date of Patent: Feb. 12, 2013

(54) INSECTICIDAL ARYL ISOXAZOLINE DERIVATIVES

(75) Inventors: Jun Mihara, Oyama (JP); Tetsuya Murata, Oyama (JP); Daiei Yamazaki, Oyama (JP); Yasushi Yoneta, Hanyu (JP); Katsuhiko Shibuya, Shimotsuke (JP); Eiichi Shimojo, Oyama (JP); Ulrich Görgens, Ratingen (DE); Andreas Turberg, Haan (DE); Thomas Bach, Wuppertal (DE)

(73) Assignee: Bayer CropScience AG, Monheim (DE)

( * ) Notice: Subject to any disclaimer, the term of this patent is extended or adjusted under 35 U.S.C. 154(b) by 279 days.

(21) Appl. No.: 12/593,047

(22) PCT Filed: Mar. 28, 2008

(86) PCT No.: PCT/EP2008/002474
§ 371 (c)(1),
(2), (4) Date: Mar. 22, 2010

(87) PCT Pub. No.: WO2008/122375
PCT Pub. Date: Oct. 16, 2008

(65) Prior Publication Data
US 2010/0179194 A1    Jul. 15, 2010

(30) Foreign Application Priority Data

Apr. 10, 2007 (JP) ................................ 2007-102395
Dec. 20, 2007 (EP) .................................... 07123793

(51) Int. Cl.
*A01N 43/80* (2006.01)
*A01N 43/40* (2006.01)
*C07D 261/04* (2006.01)
*C07D 413/10* (2006.01)
*C07D 401/12* (2006.01)

(52) U.S. Cl. .................... 514/340; 514/378; 546/272.1; 548/240

(58) Field of Classification Search .................... None
See application file for complete search history.

(56) References Cited

U.S. PATENT DOCUMENTS

| | | | | |
|---|---|---|---|---|
| 7,897,630 B2 * | 3/2011 | Lahm et al. | | 514/378 |
| 7,947,715 B2 * | 5/2011 | Mita et al. | | 514/340 |
| 2005/0250822 A1 | 11/2005 | Mita et al. | | |
| 2007/0066617 A1 | 3/2007 | Mita et al. | | |
| 2009/0156643 A1 | 6/2009 | Mita et al. | | |

FOREIGN PATENT DOCUMENTS

| | | |
|---|---|---|
| EP | 1 731 512 A1 | 12/2006 |
| WO | WO 2004/018410 A1 | 3/2004 |
| WO | WO 2004/067522 A1 | 8/2004 |
| WO | WO 2005/085216 A1 | 9/2005 |
| WO | WO 2007/105814 A1 | 9/2007 |

OTHER PUBLICATIONS

Banks, B.J., et al., "Novel anionic reagents for the stereoselective synthesis of γ-hydroxy-α-amino-acids. An X-ray crystallographic study of 2R(S)-benzoylamino-N-t-butyl-4R(S)-hydroxy-4-(4-methoxyphenyl)-3R(S)-methylbutanamide," *J. Chem. Soc., Chem. Commun.* 16:873-875, Royal Society of Chemistry, England (1983).
Jiang, B. and Xu, Y., "Trifluoroisopropenylzinc Reagent as a Useful α-(Trifluoromethyl)ethenyl Carbanion Synthetic Equivalent. Preparation and Palladium-Catalyzed Coupling with Aryl Halides," *J. Org. Chem.* 56:7336-7340, American Chemical Society, United States (1991).
Kanemasa, S., et al., "Synthesis of Hydroximoyl Chlorides from Aldoximes and Benzyltrimethylammonium Tetrachloroiodate (BTMA ICl$_4$)," *Tetrahedron* 56: 1057-1064, Elsevier Science Ltd., England (2000).
Nader, B.S., et al., "A Novel Fluoride Ion Mediated Olefination of Electron-Deficient Aryl Ketones by Alkanesulfonyl Halides," *J. Org. Chem.* 59:2898-2901, American Chemical Society, United States (1994).
Noguchi, S., et al., "Steroid [16,17-c]isoxazoline," *Chem. Pharm. Bull.* 12:1189-1192, Pharmaceutical Society of Japan, Japan (1964).
Quan, H.-D., et al., "Fluorination of n-dodecane adsorbed on porous aluminium fluoride by gaseous fluorine," *Journal of Fluorine Chemistry* 99: 167-170, Elsevier Science S.A., United States (1999).
Soli, E.D., et al., "Azide and Cyanide Displacements via Hypervalent Silicate Intermediates," *J. Org. Chem.* 64:3171-3177, American Chemical Society, United States (1999).
Sosnovskikh, V.Y., et al., "Ketone-Ketone Condensation with the Participation of Polyhaloalkyl Phenyl Ketones," English language translation of *Zhurnal Organicheskoi Khimii* 28:518-526, Plenum Publishing Corporation (1992).
International Search Report for International Patent Application No. PCT/EP2008/002474, European Patent Office, Rijswijk, Netherlands, mailed on Nov. 4, 2008.
Third Party Observation submitted to the European Patent Office in co-pending European Application No. 08734848.8, dated Oct. 21, 2010.

* cited by examiner

*Primary Examiner* — Kamal Saeed
(74) *Attorney, Agent, or Firm* — Sterne, Kessler, Goldstein & Fox P.L.L.C.

(57) ABSTRACT

The present invention relates to novel aryl isoxazoline derivatives having excellent insecticidal activity as insecticides and represented by the formula:

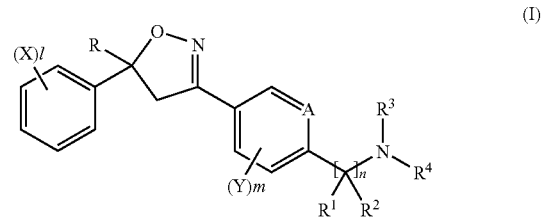

(I)

and their use as insecticides and acarizides.

9 Claims, No Drawings

INSECTICIDAL ARYL ISOXAZOLINE DERIVATIVES

The present invention relates to novel aryl isoxazoline derivatives and the use thereof as insecticides and acarizides.

Isoxazoline substituted benzamide compounds have been known to be useful as pest control agents as described in WO2005/085216.

As a result of an intensive and extensive study to develop novel compounds having more potent activity and broader spectrum as insecticides, the inventors have now found novel aryl isoxazoline derivatives which have a more pronounced activity and a broader spectrum as well as safety, and, moreover, also exert efficacy against pests which have acquired resistance to organophosphorus agents and carbamate agents.

The compounds of the present invention are represented by the following formula (I):

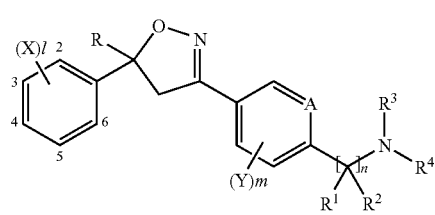

wherein

A represents C or N;

R represents alkyl or haloalkyl;

X which may be identical or different, represents Cl, Br, F, I, haloalkyl, nitro, alkyl, alkoxy, cyano, haloalkoxy, alkylsulfinyl, alkylsulfenyl, alkylsulfonyl, haloalkylsulfinyl, haloalkylsulfenyl, haloalkylsulfonyl, amino, acylamino, alkoxycarbonylamino, haloalkylcarbonylamino, haloalkoxycarbonylamino, alkylsulfonylamino, haloalkylsulfonylamino, hydroxyl or mercapto;

Y which may be identical or different, represents halogen, haloalkyl, nitro, alkyl, alkoxy, cyano, haloalkoxy, alkylsulfinyl, alkylsulfenyl, alkylsulfonyl, haloalkylsulfinyl, haloalkylsulfenyl, haloalkylsulfonyl, hydroxyl, mercapto, amino, acylamino, alkoxycarbonylamino, haloalkylcarbonylamino, haloalkoxycarbonylamino, alkylsulfonylamino or haloalkylsulfonylamino; or two adjacent Y, together with the carbon atoms to which they are attached to, form an optionally substituted cycle;

l stands for 0, 1, 2, 3, 4 or 5;

m stands for 0, 1, 2, 3 or 4;

n stands for 1, 2 or 3;

$R^1$ and $R^2$ each independently represent hydrogen, alkyl, optionally substituted cycloalkyl, haloalkyl, cyano, alkoxycarbonyl, alkenyl or alkynyl, or alternatively $R^1$ and $R^2$ together represent $C_{2-5}$ alkylene;

$R^3$ represents hydrogen, alkyl, optionally substituted cycloalkyl, haloalkyl, cyano, alkenyl, alkynyl, alkylcarbonyl or $CH_2$—$R^5$ wherein $R^5$ represents optionally substituted phenyl or an optionally substituted heterocyclic group; and $R^4$ represents formyl, cyano, alkylcarbonyl, alkylthiocarbonyl, haloalkylcarbonyl, haloalkylthiocarbonyl, alkylaminocarbonyl, alkylaminothiocarbonyl, dialkylaminocarbonyl, dialkylaminothiocarbonyl, alkoxyaminocarbonyl, alkoxythiocarbonyl, alkoxyaminothiocarbonyl, alkoxycarbonyl, thioalkoxycarbonyl, thioalkoxythiocarbonyl,

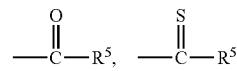

alkylsulfonyl or haloalkylsulfonyl, wherein $R^5$ is as defined above; or $R^3$ and $R^4$ taken together with the nitrogen atom to which they are attached may form a 3 to 6-membered ring which may contain, in addition to the N atom, 1 or 2 hetero atoms selected from N, O or S, and wherein the carbon atoms constituting the ring may be substituted with keto or thioketo.

In an embodiment, the invention encompasses compounds according to formula (I), wherein A represents C, R represents haloalkyl, $R^3$ represents $CH_2$—$R^5$, wherein $R^5$ stands for optionally substituted phenyl or an optionally substituted heterocyclic group selected from the group consisting of furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, quinolyl; and X, Y, l, m, n, $R^1$, $R^2$, $R^4$ are defined as above or as in one of the preferred or particularly preferred embodiments as defined herein.

In another embodiment, the invention encompasses compounds according to formula (I), wherein A represents C, R represents haloalkyl, l stands for 3

X, Y, l, m, n, $R^1$, $R^2$, $R^3$, $R^4$ are defined as above or as in one of the preferred or particularly preferred embodiments as defined herein, with the provisos (1) that when two X are identical and stand for either F, Cl, or Br, the third X does not stand for either F, $CH_3$, $CF_3$, OH, $NH_2$, $NO_2$, CN, $OCH_3$, $OCH_2CH_3$, O-(n-propyl), O—$CHF_2$ or $OCF_3$ when bound at the 4-position, or (2) that when $R^4$ represents another substituent than methyl carbonyl, X does not stand for $CF_3$ when bound at the 5-position, or (3) that when one X at the 5-position stands for Br and another X at the 3-position stands for either F or Cl, then the third X does not stand for $OCH_3$ at the 4-position.

In an embodiment of the invention the respective compounds are represented by formula (Ia)

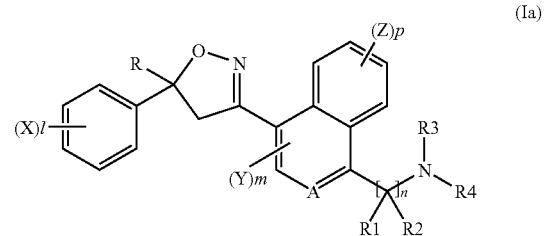

wherein

A represents C or N, each of which may be substituted with a substituent Y;

R represents alkyl or haloalkyl;

X which may be identical or different, represents halogen, haloalkyl, nitro, alkyl, alkoxy, cyano, haloalkoxy, alkylsulfinyl, alkylsulfenyl, alkylsulfonyl, haloalkylsulfinyl, haloalkylsulfenyl, haloalkylsulfonyl, amino, acylamino, alkoxycarbonylamino, haloalkylcarbonylamino, haloalkoxycarbonylamino, alkylsulfonylamino, haloalkylsulfonylamino, hydroxyl or mercapto;

Z or Y which may be identical or different, represent halogen, haloalkyl, nitro, alkyl, alkoxy, cyano, haloalkoxy, alkylsulfinyl, alkylsulfenyl, alkylsulfonyl, haloalkylsulfinyl, haloalkylsulfenyl, haloalkylsulfonyl, hydroxyl, mercapto, amino, acylamino, alkoxycarbonylamino, haloalkylcarbonylamino, haloalkoxycarbonylamino, alkylsulfonylamino or haloalkylsulfonylamino;

l stands for 0, 1, 2, 3, 4 or 5;

m stands for 0, 1, or 2;

n stands for 1, 2 or 3;

p stands for 0, 1, 2, 3, or 4;

$R^1$ and $R^2$ each independently represent hydrogen, alkyl, optionally substituted cycloalkyl, haloalkyl, cyano, alkoxycarbonyl, alkenyl or alkynyl, or alternatively $R^1$ and $R^2$ together represent $C_{2-5}$ alkylene $R^3$ represents hydrogen, alkyl, optionally substituted cycloalkyl, haloalkyl, cyano, alkenyl, alkynyl, alkylcarbonyl or $CH_2$—$R^5$ wherein $R^5$ represents optionally substituted phenyl or an optionally substituted heterocyclic group; and $R^4$ represents formyl, cyano, alkylcarbonyl, alkylthiocarbonyl, haloalkylcarbonyl, haloalkylthiocarbonyl, alkylaminocarbonyl, alkylaminothiocarbonyl, dialkylaminocarbonyl, dialkylaminothiocarbonyl, alkoxyaminocarbonyl, alkoxythiocarbonyl, alkoxyaminothiocarbonyl, alkoxycarbonyl, thioalkoxycarbonyl, thioalkoxythiocarbonyl,

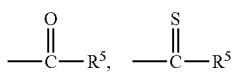

alkylsulfonyl or haloalkylsulfonyl, wherein $R^5$ is as defined above; or $R^3$ and $R^4$ taken together with the nitrogen atom to which they are attached may form a 3 to 6-membered ring which may contain, in addition to the N atom, 1 or 2 hetero atoms selected from N, O or S, and wherein the carbon atoms constituting the ring may be substituted with keto or thioketo.

The compounds of formula (I) may be obtained by the preparation processes (a) to (d) described below.

Preparation Process (a):

A process for the preparation of a compound according to the invention comprising the step of reacting a compound of formula (II)

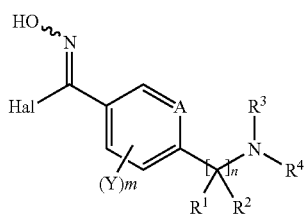

(II)

wherein A, Y, m, n, $R^1$, $R^2$, $R^3$ and $R^4$ are as defined above, and Hal represents halogen, with a compound of formula (III)

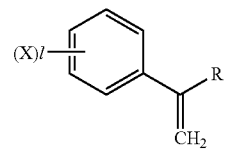

(III)

wherein R, X and l are as defined above.

Preparation Process (b):

A process for the preparation of a compound according to the invention comprising the step of reacting a compound of formula (IV)

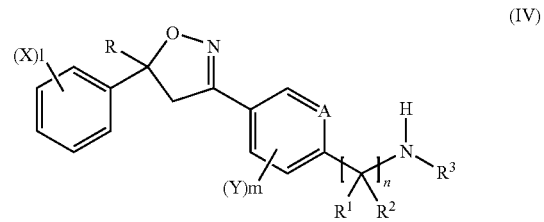

(IV)

wherein A, R, X, l, Y, m, n, $R^1$, $R^2$ and $R^3$ are as defined above, with a compound of formula (V)

$R^4$-L    (V)

wherein $R^4$ is as defined above and L represents halogen, alkylsulfonyloxy, arylsulfonyloxy or alkylcarbonyloxy.

Preparation Process (c)

A process for the preparation of a compound according to the invention comprising the step of reacting a compound of formula (IV)

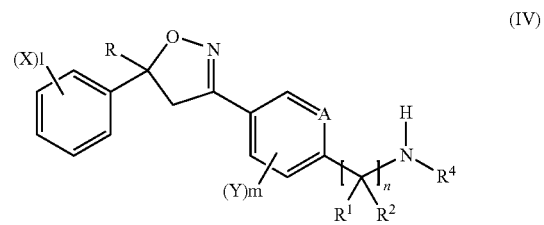

(IV)

wherein A, R, X, l, Y, m, n, $R^1$, $R^2$ and $R^4$ are as defined above, with a compound of formula (VII)

$R^3$-L    (VII)

wherein $R^3$ is as defined above and L represents halogen, alkylsulfonyloxy, arylsulfonyloxy or alkylcarbonyloxy.

Preparation Process (d)

A process for the preparation of a compound according to the invention comprising the step of reacting a compound of formula (VIII)

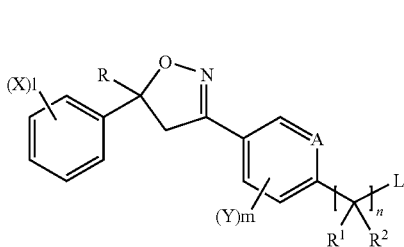

(VIII)

wherein A, R, X, l, Y, m, n and L are as defined above, with a compound of formula (IX)

(IX)

wherein $R^3$ and $R^4$ are as defined above.

According to the present invention, aryl isoxazoline derivatives of the aforementioned formula (I) have potent insecticidal and acaricidal activity.

As used herein, the term "alkyl" refers to linear or branched $C_{1-12}$ alkyl including, for example, ethyl, methyl, n- or isopropyl, n-, iso-, sec-, or tert-butyl, n-pentyl, n-hexyl, n-heptyl, n-octyl, n-nonyl, n-decyl, n-undecyl and n-dodecyl, and preferably refers to $C_{1-6}$ alkyl. The alkyl moiety in a group having alkyl as a part of its formula may have the same meaning as described for the aforementioned "alkyl". The alkyl group can be unsubstituted or substituted with at least one suitable substituent.

The term "acylamino" refers to, for example, alkylcarbonylamino, cycloalkylcarbonylamino and benzoylamino, wherein the alkyl moiety may the same meaning as described for the aforementioned "alkyl", and cycloalkyl moiety may have the same meaning as described below. The acylamino group can be unsubstituted or substituted with at least one suitable substituent.

The term "halogen" and a halogen moiety in a group substituted with halogen represent fluorine, chlorine, bromine and iodine. Preferred halogens are fluorine, chlorine and bromine.

The term "cycloalkyl" refers to $C_{3-8}$ cycloalkyl including, for example, cyclopropyl, cyclobutyl, cyclopentyl, cyclohexyl, cycloheptyl and cyclooctyl, and preferably refers to $C_{3-7}$ cycloalkyl. The cycloalkyl group can be unsubstituted or substituted with at least one suitable substituent.

The term "alkenyl" refers to $C_{2-5}$ alkenyl including, for example, vinyl, allyl, 1-propenyl, 1-(or 2- or 3-) butenyl and 1-pentenyl, and preferably refers to $C_{2-4}$ alkenyl. The alkenyl group can be unsubstituted or substituted with at least one suitable substituent.

A "cyclic group" preferably refers to a cycle containing 3 to 6 carbon atoms. This group is preferably an aromatic ring, most preferred a benzene ring. The cyclic group can be unsubstituted or substituted with at least one suitable substituent.

A "heterocyclic group" preferably refers to a 5- or 6-membered heterocyclic group containing at least one of hetero atoms selected from N, O or S, and said heterocyclic group also refers to a condensed heterocyclic group which may be benzo-condensed. The heterocyclic group can be unsubstituted or substituted with at least one suitable substituent.

Specific examples of "heterocyclic groups" include furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, quinolyl and the like.

Suitable substituents include for example the following chemical groups, namely amino, hydroxy, halogen, intro, cyano, isocyano, mercapto, isothiocyanato, carboxy, carbonamide, SF5, aminosulfonyl, alkyl, cycloalkyl, alkenyl, cycloalkenyl, alkinyl, monoalkyl-amino, dialkyl-amino, N-alkanoyl-amino, alkoxy, alkenyloxy, alkinyloxy, cycloalkoxy, cycloalkenyloxy, alkoxy-carbonyl, alkenyloxy-carbonyl, alkinyloxy-carbonyl, aryloxycarbonyl, alkanoyl, alkenyl-carbonyl, alkinyl-carbonyl, aryl-carbonyl, alkylthio, cycloalkylthio, alkenylthio, cycloalkenylthio, alkinylthio, alkylsulfenyl, alkylsulfinyl, including both enantiomeric forms of alkylsulfinyl, alkylsulfonyl, monoalkyl-aminosulfonyl, dialkyl-aminosulfonyl, alkylphosphinyl, alkylphosphonyl, including both enantiomeric forms of alkylphosphinyl and alkylphosphonyl, respectively, N-alkyl-aminocarbonyl, N,N-dialkyl-aminocarbonyl, N-alkanoyl-amino-carbonyl, N-alkanoyl-N-alkyl-aminocarbonyl, aryl, aryloxy, benzyl, benzyloxy, benzylthio, arylthio, arylamino, benzylamino, heterocyclyl and trialkylsilyl. Substituents which are further substituted, like for example alkoxyalkyl, alkylthioalkyl, alkylthioalkoxy, alkoxyalkoxy, phenethyl, benzyloxy, haloalkyl, haloalkoxy, haloalkylthio, haloalkanoyl, haloalkylcarbonyl, haloalkoxycarbonyl, haloalkoxyalkoxy, haloalkoxyalkylthio, haloalkoxyalkanoyl, haloalkoxyalkyl are also included.

Among the compounds represented by formula (I) of the present invention, preferred are the compounds wherein A represents C or N;

R represents $C_{1-6}$ alkyl or $C_{1-6}$ haloalkyl;

X which may be identical or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfinyl, $C_{1-6}$ alkylsulfenyl, $C_{1-6}$ alkylsulfonyl, $C_{1-6}$ haloalkylsulfinyl, $C_{1-6}$ haloalkylsulfenyl, $C_{1-6}$ haloalkylsulfonyl, amino, $C_{1-6}$ alkyl-carbonyl, $C_{1-6}$ alkoxycarbonylamino, $C_{1-6}$ haloalkylcarbonylamino, $C_{1-6}$ haloalkoxycarbonylamino, $C_{1-6}$ alkylsulfonylamino, $C_{1-6}$ haloalkylsulfonylamino, hydroxyl or mercapto;

Y which may be identical or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfinyl, $C_{1-6}$ alkylsulfenyl, $C_{1-6}$ alkylsulfonyl, $C_{1-6}$ haloalkylsulfinyl, $C_{1-6}$ haloalkylsulfenyl, $C_{1-6}$ haloalkylsulfonyl, hydroxyl, mercapto, amino, $C_{1-4}$ alkylcarbonylamino, benzoylamino, $C_{1-6}$ alkoxycarbonylamino, $C_{1-6}$ haloalkyl-carbonylamino, $C_{1-6}$ haloalkoxycarbonylamino, $C_{1-6}$ alkylsulfonylamino or $C_{1-6}$ haloalkylsulfonylamino;

l represents 0, 1, 2 or 3;

m represents 0, 1 or 2;

n represents 1;

$R^1$ and $R^2$ each independently represent hydrogen, $C_{1-6}$ alkyl, optionally substituted $C_{3-7}$ cycloalkyl, $C_{1-6}$ haloalkyl, cyano, $C_{1-6}$ alkoxycarbonyl, $C_{2-4}$ alkenyl or $C_{2-4}$ alkynyl, or $R^1$ and $R^2$ together represent $C_{2-5}$ alkylene;

$R^3$ represents hydrogen, $C_{1-6}$ alkyl, optionally substituted $C_{3-7}$ cycloalkyl, $C_{1-6}$ haloalkyl, cyano, $C_{2-4}$ alkenyl, $C_{2-4}$ alkynyl, $C_{1-6}$ alkynylcarbonyl or $CH_2$—$R^5$ wherein $R^5$ represents optionally substituted phenyl or an optionally substituted heterocyclic group; and $R^4$ represents formyl, cyano, $C_{1-6}$ alkylcarbonyl, $C_{1-6}$ alkylthiocarbonyl, $C_{1-6}$ haloalkylcarbonyl, $C_{1-6}$ haloalkylthiocarbonyl, $C_{1-6}$ alkylaminocarbonyl, $C_{1-6}$ alkyl-aminothiocarbonyl, $C_{2-8}$ (total number of carbons) dialkylaminocarbonyl, $C_{2-8}$ (total number of carbons) dialkylaminothiocarbonyl, $C_{1-6}$ alkoxyaminocarbonyl, $C_{1-6}$ alkoxythiocarbonyl, $C_{1-6}$ alkoxyaminothiocarbonyl, $C_{1-6}$ alkoxycarbonyl, thio-$C_{1-6}$ alkoxycarbonyl, thio-$C_{1-6}$ alkoxythiocarbonyl,

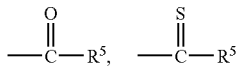

$C_{1-6}$ alkylsulfonyl or $C_{1-6}$ haloalkyl-sulfonyl, wherein $R^5$ is as defined above; or $R^3$ and $R^4$ taken together with the nitrogen atom to which they are attached may form a 4- or 5-membered ring which may contain, in addition to the N atom, 1 or 2 hetero atoms selected from N, O or S, and wherein the carbon atoms constituting the ring may be substituted with keto or thioketo.

In an also preferred embodiment of the invention the compounds are represented by formula (Ia) wherein A represents C which may be substituted with a substituent Y;

R represents $C_{1-6}$ alkyl or $C_{1-6}$ haloalkyl;

X which may be identical or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfinyl, $C_{1-6}$ alkylsulfenyl, $C_{1-6}$ alkylsulfonyl, $C_{1-6}$ haloalkyl-sulfinyl, $C_{1-6}$ haloalkylsulfenyl, $C_{1-6}$ haloalkylsulfonyl, amino, $C_{1-6}$ alkylcarbonyl, $C_{1-6}$ alkoxycarbonylamino, $C_{1-6}$ haloalkylcarbonylamino, $C_{1-6}$ haloalkoxycarbonylamino, $C_{1-6}$ alkylsulfonylamino, $C_{1-6}$ haloalkyl-sulfonylamino, hydroxyl or mercapto;

Z or Y, which may be identical or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfinyl, $C_{1-6}$ alkylsulfenyl, $C_{1-6}$ alkylsulfonyl, $C_{1-6}$ haloalkylsulfinyl, $C_{1-6}$ haloalkylsulfenyl, $C_{1-6}$ haloalkylsulfonyl, hydroxyl, mercapto, amino, $C_{1-4}$ alkylcarbonylamino, benzoylamino, $C_{1-6}$ alkoxycarbonylamino, $C_{1-6}$ haloalkylcarbonylamino, $C_{1-6}$ haloalkoxycarbonylamino, $C_{1-6}$ alkylsulfonylamino or $C_{1-6}$ haloalkylsulfonylamino;

l stands for 0, 1, 2 or 3;

m stands for 0, 1 or 2;

n stands for 1;

p stands for 0, 1, 2, 3 or 4;

$R^1$ and $R^2$ each independently represent hydrogen, $C_{1-6}$ alkyl, optionally substituted $C_{3-7}$ cycloalkyl, $C_{1-6}$ haloalkyl, cyano, $C_{1-6}$ alkoxycarbonyl, $C_{2-4}$ alkenyl or $C_{2-4}$ alkynyl, or $R^1$ and $R^2$ together represent $C_{2-5}$ alkylene;

$R^3$ represents hydrogen, $C_{1-6}$ alkyl, optionally substituted $C_{3-7}$ cycloalkyl, $C_{1-6}$ haloalkyl, cyano, $C_{2-4}$ alkenyl, $C_{2-4}$ alkynyl, $C_{1-6}$ alkynylcarbonyl or $CH_2$—$R^5$ wherein $R^5$ represents optionally substituted phenyl or an optionally substituted heterocyclic group; and $R^4$ represents formyl, cyano, $C_{1-6}$ alkylcarbonyl, $C_{1-6}$ alkylthiocarbonyl, $C_{1-6}$ haloalkylcarbonyl, $C_{1-6}$ haloalkylthiocarbonyl, $C_{1-6}$ alkylaminocarbonyl, $C_{1-6}$ alkylamino-thiocarbonyl, $C_{2-8}$ (total number of carbons) dialkylaminocarbonyl, $C_{2-8}$ (total number of carbons) dialkylaminothiocarbonyl, $C_{1-6}$ alkoxyaminocarbonyl, $C_{1-6}$ alkoxythio-carbonyl, $C_{1-6}$ alkoxyaminothiocarbonyl, $C_{1-6}$ alkoxycarbonyl, thio-$C_{1-6}$ alkoxycarbonyl, thio-$C_{1-6}$ alkoxythiocarbonyl,

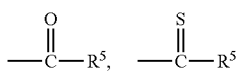

$C_{1-6}$ alkylsulfonyl or $C_{1-6}$ haloalkyl-sulfonyl, wherein $R^5$ is as defined above; or $R^3$ and $R^4$ taken together with the nitrogen atom to which they are attached may form a 4- or 5-membered ring which may contain, in addition to the N atom, 1 or 2 hetero atoms selected from N, O or S, and wherein the carbon atoms constituting the ring may be substituted with keto or thioketo.

In a further preferred embodiment of the invention the compounds are represented by formula (Ia) wherein A represents N, which may be substituted with a substituent Y;

R represents $C_{1-6}$ alkyl or $C_{1-6}$ haloalkyl;

X which may be identical or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfinyl, $C_{1-6}$ alkylsulfenyl, $C_{1-6}$ alkylsulfonyl, $C_{1-6}$ haloalkyl-sulfinyl, $C_{1-6}$ haloalkylsulfenyl, $C_{1-6}$ haloalkylsulfonyl, amino, $C_{1-6}$ alkylcarbonyl, $C_{1-6}$ alkoxycarbonylamino, $C_{1-6}$ haloalkylcarbonylamino, $C_{1-6}$ haloalkoxycarbonylamino, $C_{1-6}$ alkylsulfonylamino, $C_{1-6}$ haloalkyl-sulfonylamino, hydroxyl or mercapto;

Z or Y, which may be identical or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfinyl, $C_{1-6}$ alkylsulfenyl, $C_{1-6}$ alkylsulfonyl, $C_{1-6}$ haloalkylsulfinyl, $C_{1-6}$ haloalkylsulfenyl, $C_{1-6}$ haloalkylsulfonyl, hydroxyl, mercapto, amino, $C_{1-4}$ alkylcarbonylamino, benzoylamino, $C_{1-6}$ alkoxycarbonylamino, $C_{1-6}$ haloalkylcarbonylamino, $C_{1-6}$ haloalkoxycarbonylamino, $C_{1-6}$ alkylsulfonylamino or $C_{1-6}$ haloalkylsulfonylamino;

l stands for 0, 1, 2 or 3;

m stands for 0, 1 or 2;

n stands for 1;

p stands for 0, 1, 2, 3 or 4;

$R^1$ and $R^2$ each independently represent hydrogen, $C_{1-6}$ alkyl, optionally substituted $C_{3-7}$ cycloalkyl, $C_{1-6}$ haloalkyl, cyano, $C_{1-6}$ alkoxycarbonyl, $C_{2-4}$ alkenyl or $C_{2-4}$ alkynyl, or $R^1$ and $R^2$ together represent $C_{2-5}$ alkylene;

$R^3$ represents hydrogen, $C_{1-6}$ alkyl, optionally substituted $C_{3-7}$ cycloalkyl, $C_{1-6}$ haloalkyl, cyano, $C_{2-4}$ alkenyl, $C_{2-4}$ alkynyl, $C_{1-6}$ alkynylcarbonyl or $CH_2$—$R^5$ wherein $R^5$ represents optionally substituted phenyl or an optionally substituted heterocyclic group; and $R^4$ represents formyl, cyano, $C_{1-6}$ alkylcarbonyl, $C_{1-6}$ alkylthiocarbonyl, $C_{1-6}$ haloalkylcarbonyl, $C_{1-6}$ haloalkylthiocarbonyl, $C_{1-6}$ alkylaminocarbonyl, $C_{1-6}$ alkylaminothiocarbonyl, $C_{2-8}$ (total number of carbons) dialkylaminocarbonyl, $C_{2-8}$ (total number of carbons) dialkylaminothiocarbonyl, $C_{1-6}$ alkoxyaminocarbonyl, $C_{1-6}$ alkoxythio-carbonyl, $C_{1-6}$ alkoxyaminothiocarbonyl, $C_{1-6}$ alkoxycarbonyl, thio-$C_{1-6}$ alkoxycarbonyl, thio-$C_{1-6}$ alkoxythiocarbonyl,

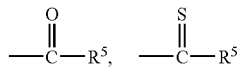

$C_{1-6}$ alkylsulfonyl or $C_{1-6}$ haloalkyl-sulfonyl, wherein $R^5$ is as defined above; or $R^3$ and $R^4$ taken together with the nitrogen atom to which they are attached may form a 4- or 5-membered ring which may contain, in addition to the N atom, 1 or 2 hetero atoms selected from N, O or S, and wherein the carbon atoms constituting the ring may be substituted with keto or thioketo.

Among those compounds of formula (I), particularly preferred are the compounds wherein A represents C or N;

R represents $C_{1-4}$ alkyl or $C_{1-4}$ haloalkyl;

X which may be identical or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylsulfinyl, $C_{1-4}$ alkylsulfenyl, $C_{1-4}$ alkylsulfonyl, $C_{1-4}$ haloalkylsulfinyl, $C_{1-4}$ haloalkylsulfenyl, $C_{1-4}$ haloalkylsulfonyl, amino, $C_{1-4}$ alkylcarbonyl, $C_{1-4}$ alkoxycarbonylamino, $C_{1-4}$ haloalkylcarbonylamino, $C_{1-4}$ haloalkoxycarbonylamino, $C_{1-4}$ alkylsulfonylamino, $C_{1-4}$ haloalkylsulfonylamino, hydroxyl or mercapto;

Y which may be identical or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylsulfinyl, $C_{1-4}$ alkylsulfenyl, $C_{1-4}$ alkylsulfonyl, $C_{1-4}$ haloalkylsulfinyl, $C_{1-4}$ haloalkylsulfenyl, $C_{1-4}$ haloalkylsulfonyl, hydroxyl, mercapto, amino, $C_{1-4}$ alkylcarbonylamino, benzoylamino, $C_{1-4}$ alkoxycarbonylamino, $C_{1-4}$ haloalkylcarbonylamino, $C_{1-4}$ haloalkoxycarbonylamino, $C_{1-4}$ alkylsulfonylamino or $C_{1-4}$ haloalkylsulfonylamino;

l represents 0, 1, 2 or 3;
m represents 1;
n represents 1;

$R^1$ and $R^2$ each independently represent hydrogen, $C_{1-4}$ alkyl, optionally substituted $C_{3-6}$ cycloalkyl, $C_{1-4}$ haloalkyl, cyano, $C_{1-4}$ alkoxycarbonyl, $C_{2-3}$ alkenyl or $C_{2-3}$ alkynyl, or alternatively $R^1$ and $R^2$ together represent $C_{2-5}$ alkylene;

$R^3$ represents hydrogen, $C_{1-4}$ alkyl, optionally substituted $C_{3-6}$ cycloalkyl, $C_{1-4}$ haloalkyl, cyano, $C_{2-3}$ alkenyl, $C_{2-3}$ alkynyl, $C_{1-4}$ alkylcarbonyl or $CH_2$—$R^5$ wherein $R^5$ represents optionally substituted phenyl or an optionally substituted heterocyclic group; and $R^4$ represents formyl, cyano, $C_{1-4}$ alkylcarbonyl, $C_{1-4}$ alkylthiocarbonyl, $C_{1-4}$ haloalkylcarbonyl, $C_{1-4}$ haloalkylthiocarbonyl, $C_{1-4}$ alkylaminocarbonyl, $C_{1-4}$ alkylaminothiocarbonyl, $C_{2-6}$ (total number of carbons) dialkylaminocarbonyl, $C_{2-6}$ (total number of carbons) dialkylaminothiocarbonyl, $C_{1-4}$ alkoxyaminocarbonyl, $C_{1-4}$ alkoxythiocarbonyl, $C_{1-4}$ alkoxyaminothiocarbonyl, $C_{1-4}$ alkoxycarbonyl, thio-$C_{1-4}$ alkoxycarbonyl, thio-$C_{1-4}$ alkoxythiocarbonyl,

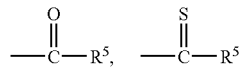

$C_{1-4}$ alkylsulfonyl or $C_{1-4}$ haloalkyl-sulfonyl, wherein $R^5$ is as defined above; or $R^3$ and $R^4$ taken together with the nitrogen atom to which they are attached may form a 4- or 5-membered ring which may contain, in addition to the N atom, 1 or 2 hetero atoms optionally selected from N, O or S, and wherein the carbon atoms constituting the ring may be substituted with keto or thioketo.

In an also particularly preferred embodiment of the invention the compounds are represented by formula (Ia) wherein A represents C, which may be substituted with a substitutent Y;

R represents $C_{1-4}$ alkyl or $C_{1-4}$ haloalkyl;

X which may be identical or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylsulfinyl, $C_{1-4}$ alkylsulfenyl, $C_{1-4}$ alkylsulfonyl, $C_{1-4}$ haloalkylsulfinyl, $C_{1-4}$ haloalkylsulfenyl, $C_{1-4}$ haloalkylsulfonyl, amino, $C_{1-4}$ alkylcarbonyl, $C_{1-4}$ alkoxycarbonylamino, $C_{1-4}$ haloalkylcarbonylamino, $C_{1-4}$ haloalkoxycarbonylamino, $C_{1-4}$ alkylsulfonylamino, $C_{1-4}$ haloalkylsulfonylamino, hydroxyl or mercapto;

Z or Y, which may be identical or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylsulfinyl, $C_{1-4}$ alkylsulfenyl, $C_{1-4}$ alkylsulfonyl, $C_{1-4}$ haloalkylsulfinyl, $C_{1-4}$ haloalkylsulfenyl, $C_{1-4}$ haloalkylsulfonyl, hydroxyl, mercapto, amino, $C_{1-4}$ alkylcarbonylamino, benzoylamino, $C_{1-4}$ alkoxycarbonylamino, $C_{1-4}$ haloalkylcarbonylamino, $C_{1-4}$ haloalkoxycarbonylamino, $C_{1-4}$ alkylsulfonylamino or $C_{1-4}$ haloalkylsulfonylamino;

l stands for 0, 1, 2 or 3;
m is 0 or 1;
n is 1;
p stands for 0, 1, or 3

$R^1$ and $R^2$ each independently represent hydrogen, $C_{1-4}$ alkyl, optionally substituted $C_{3-6}$ cycloalkyl, $C_{1-4}$ haloalkyl, cyano, $C_{1-4}$ alkoxycarbonyl, $C_{2-3}$ alkenyl or $C_{2-3}$ alkynyl, or alternatively $R^1$ and $R^2$ together represent $C_{2-5}$ alkylene;

$R^3$ represents hydrogen, $C_{1-4}$ alkyl, optionally substituted $C_{3-6}$ cycloalkyl, $C_{1-4}$ haloalkyl, cyano, $C_{2-3}$ alkenyl, $C_{2-3}$ alkynyl, $C_{1-4}$ alkylcarbonyl or $CH_2$—$R^5$ wherein $R^5$ represents optionally substituted phenyl or an optionally substituted heterocyclic group; and $R^4$ represents formyl, cyano, $C_{1-4}$ alkylcarbonyl, $C_{1-4}$ alkylthiocarbonyl, $C_{1-4}$ haloalkylcarbonyl, $C_{1-4}$ haloalkylthiocarbonyl, $C_{1-4}$ alkylaminocarbonyl, $C_{1-4}$ alkylaminothiocarbonyl, $C_{2-6}$ (total number of carbons) dialkylaminocarbonyl, $C_{2-6}$ (total number of carbons) dialkylaminothiocarbonyl, $C_{1-4}$ alkoxyaminocarbonyl, $C_{1-4}$ alkoxythiocarbonyl, $C_{1-4}$ alkoxyaminothiocarbonyl, $C_{1-4}$ alkoxycarbonyl, thio-$C_{1-4}$ alkoxycarbonyl, thio-$C_{1-4}$ alkoxythiocarbonyl,

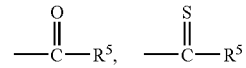

$C_{1-4}$ alkylsulfonyl or $C_{1-4}$ haloalkyl-sulfonyl, wherein $R^5$ is as defined above; or $R^3$ and $R^4$ taken together with the nitrogen atom to which they are attached may form a 4- or 5-membered ring which may contain, in addition to the N atom, 1 or 2 hetero atoms optionally selected from N, O or S, and wherein the carbon atoms constituting the ring may be substituted with keto or thioketo.

In an equally preferred embodiment of the invention the compounds are represented by formula (I), wherein A represents C;

R represents $CF_3$;

X which may be identical or different, represents Cl, F, I, Br, $CF_3$, $NO_2$, $C_{1-4}$ alkoxy, cyano, $C_{1-4}$ fluoroalkoxy, $C_{1-4}$ alkylsulfonyl, amino, $C_{1-4}$ alkylcarbonyl, hydroxyl or mercapto;

Y which may be identical or different, represents Cl, F, I, Br, $CF_3$, $NO_2$, $C_{1-4}$ alkyl, $C_{1-4}$ alkoxy, cyano, $C_{1-4}$ haloalkoxy, hydroxyl, amino;

l represents 1, 2 or 3;
m represents 1;
n represents 1;

$R^1$ and $R^2$ each independently represent hydrogen or $C_{1-4}$ alkyl;

$R^3$ represents hydrogen, $C_{1-4}$ alkyl, or $CH_2$—$R^5$ wherein $R^5$ represents optionally substituted phenyl or an optionally substituted heterocyclic group, selected from the group consisting of furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, quinolyl; and $R^4$ represents $C_{1-4}$ alkylcarbonyl, vinylcarbonyl, $C_{1-4}$ alkylthiocarbonyl, $C_{1-4}$ haloalkylcarbonyl, $C_{1-4}$ alkylaminocarbonyl, di-$(C_1-C_2)$alkylaminocarbonyl, $C_{1-4}$ alkoxyaminocarbonyl, $C_{1-4}$ alkoxycarbonyl, thio-$C_{1-4}$ alkoxycarbonyl, $C_{1-4}$ alkylsulfonyl, —C(O)$R^5$, C(S)$R^5$, wherein $R^5$ represents optionally substituted phenyl or an optionally substituted heterocyclic group selected from the group consisting of furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, quinolyl.

In a further particularly preferred embodiment of the invention the compounds are represented by formula (Ia) wherein A represents N, which may be substituted with a substituent Y;

R represents $C_{1-4}$ alkyl or $C_{1-4}$ haloalkyl;

X which may be identical or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylsulfinyl, $C_{1-4}$ alkylsulfenyl, $C_{1-4}$ alkylsulfonyl, $C_{1-4}$ haloalkylsulfinyl, $C_{1-4}$ haloalkylsulfenyl, $C_{1-4}$ haloalkylsulfonyl, amino, $C_{1-4}$ alkylcarbonyl, $C_{1-4}$ alkoxycarbonylamino, $C_{1-4}$ haloalkylcarbonylamino, $C_{1-4}$ haloalkoxycarbonylamino, $C_{1-4}$ alkylsulfonylamino, $C_{1-4}$ haloalkylsulfonylamino, hydroxyl or mercapto;

Z or Y, which may be identical or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylsulfinyl, $C_{1-4}$ alkylsulfenyl, $C_{1-4}$ alkylsulfonyl, $C_{1-4}$ haloalkylsulfinyl, $C_{1-4}$ haloalkylsulfenyl, $C_{1-4}$ haloalkylsulfonyl, hydroxyl, mercapto, amino, $C_{1-4}$ alkylcarbonylamino, benzoylamino, $C_{1-4}$ alkoxycarbonylamino, $C_{1-4}$ haloalkylcarbonylamino, $C_{1-4}$ haloalkoxycarbonylamino, $C_{1-4}$ alkylsulfonylamino or $C_{1-4}$ haloalkylsulfonylamino;

l stands for 0, 1, 2 or 3;

m is 0 or 1;

n is 1;

p stands for 0, 1, or 3

$R^1$ and $R^2$ each independently represent hydrogen, $C_{1-4}$ alkyl, optionally substituted $C_{3-6}$ cycloalkyl, $C_{1-4}$ haloalkyl, cyano, $C_{1-4}$ alkoxycarbonyl, $C_{2-3}$ alkenyl or $C_{2-3}$ alkynyl, or alternatively $R^1$ and $R^2$ together represent $C_{2-5}$ alkylene;

$R^3$ represents hydrogen, $C_{1-4}$ alkyl, optionally substituted $C_{3-6}$ cycloalkyl, $C_{1-4}$ haloalkyl, cyano, $C_{2-3}$ alkenyl, $C_{2-3}$ alkynyl, $C_{1-4}$ alkylcarbonyl or CH$_2$—$R^5$ wherein $R^5$ represents optionally substituted phenyl or an optionally substituted heterocyclic group; and $R^4$ represents formyl, cyano, $C_{1-4}$ alkylcarbonyl, $C_{1-4}$ alkylthiocarbonyl, $C_{1-4}$ haloalkylcarbonyl, $C_{1-4}$ haloalkylthiocarbonyl, $C_{1-4}$ alkylaminocarbonyl, $C_{1-4}$ alkylaminothiocarbonyl, $C_{2-6}$ (total number of carbons) dialkylaminocarbonyl, $C_{2-6}$ (total number of carbons) dialkylaminothiocarbonyl, $C_{1-4}$ alkoxyaminocarbonyl, $C_{1-4}$ alkoxythiocarbonyl, $C_{1-4}$ alkoxyaminothiocarbonyl, $C_{1-4}$ alkoxycarbonyl, thio-$C_{1-4}$ alkoxycarbonyl, thio-$C_{1-4}$ alkoxythiocarbonyl,

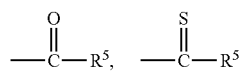

$C_{1-4}$ alkylsulfonyl or $C_{1-4}$ haloalkyl-sulfonyl, wherein $R^5$ is as defined above; or $R^3$ and $R^4$ taken together with the nitrogen atom to which they are attached may form a 4- or 5-membered ring which may contain, in addition to the N atom, 1 or 2 hetero atoms optionally selected from N, O or S, and wherein the carbon atoms constituting the ring may be substituted with keto or thioketo.

In another aspect the invention is directed to a pharmaceutical composition comprising at least one compound according to the invention, preferably to at least one compound according to one of the embodiments as defined herein, more preferably to at least one compound according to a preferred embodiment as defined herein, and most preferably to at least one compound according to a particularly preferred embodiment as defined herein, which is useful for combating animal parasites.

The compounds of formula (I) possess asymmetric carbons, and thus encompass optical isomers. Additionally, compounds according to the invention can be present in different polymorphic forms or as a mixture of different polymorphic forms. Both the pure polymorphs and the polymorph mixtures are provided by the invention and can be used according to the invention.

When using, for example, 4-(acetamidomethyl)-N-hydroxybenzene carboximidoyl chloride and 1,3-dichloro-5-[1-(trifluoromethyl)vinyl]benzene as starting materials, the aforementioned preparation process (a) may be represented by the following reaction scheme.

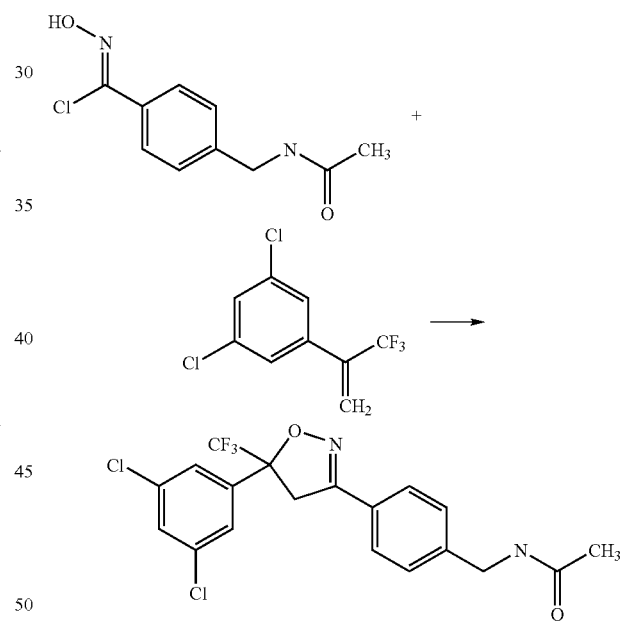

When using, for example, 1-{4-[5-(3,5-dichlorophenyl)-5-(trifluoromethyl)-4,5-dihydroisoxazole-3-yl]phenyl}-methanamine and acetyl chloride as starting materials, the aforementioned preparation process (b) may be represented by the following reaction scheme.

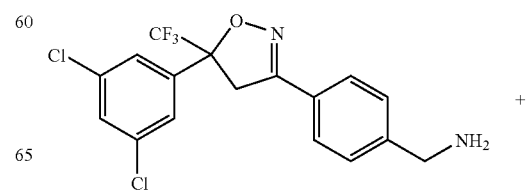

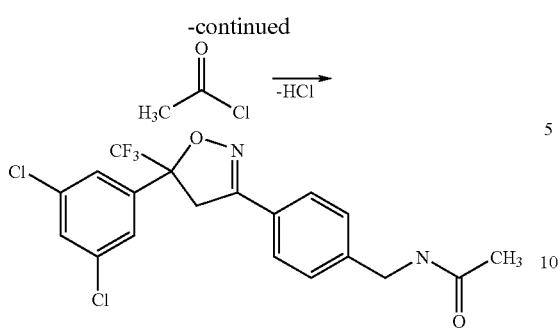

When using, for example, N-{4-[5-(3,5-dichlorophenyl)-5-(trifluoromethyl)-4,5-dihydroisoxazole-3-yl]benzyl}acetamide and iodomethane as starting materials, above preparation process (c) may be represented by the following reaction scheme.

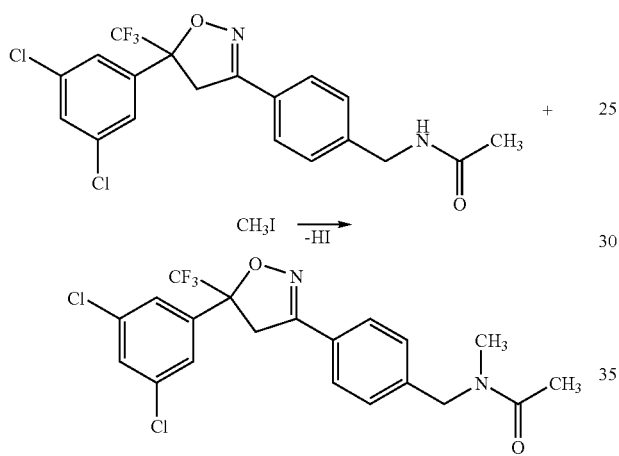

When using, for example, 3-[3-bromo-4-(bromomethyl)phenyl]-5-(3,5-dichlorophenyl)-5-(trifluoromethyl)-4,5-dihydroisoxazole and thioacetamide as starting materials, the aforementioned preparation process (d) may be represented by the following reaction scheme.

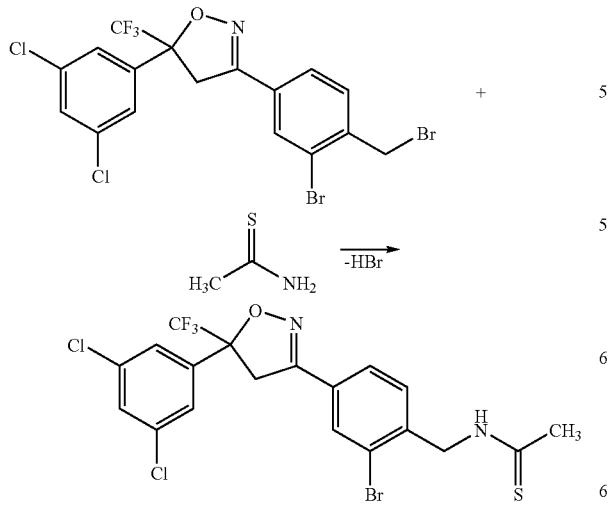

The compounds of formula (II) used as starting materials in preparation process (a) are novel compounds and may be obtained by reacting a compound represented by the formula:

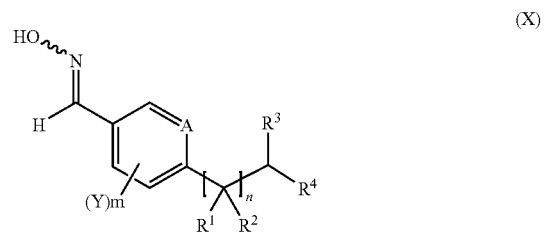

(X)

wherein A, Y, m, n, $R^1$, $R^2$, $R^3$ and $R^4$ are defined above, with a halogenating agent.

Many of the compounds of the aforementioned formula (X) are novel compounds and may be obtained by reacting a compound represented by the following formula:

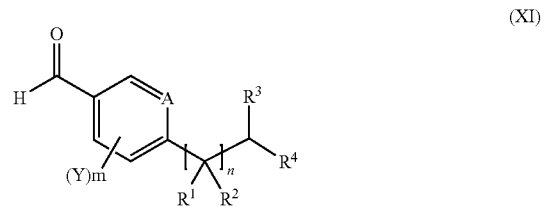

(XI)

wherein A, Y, m, n, $R^1$, $R^2$, $R^3$ and $R^4$ are as defined above, with hydroxylamine or salt thereof.

Many of the compounds of the aforementioned formula (XI) are novel compounds and may be obtained according to the process described, for example, in WO 2004/067522.

A typical reaction process is represented by the following scheme:

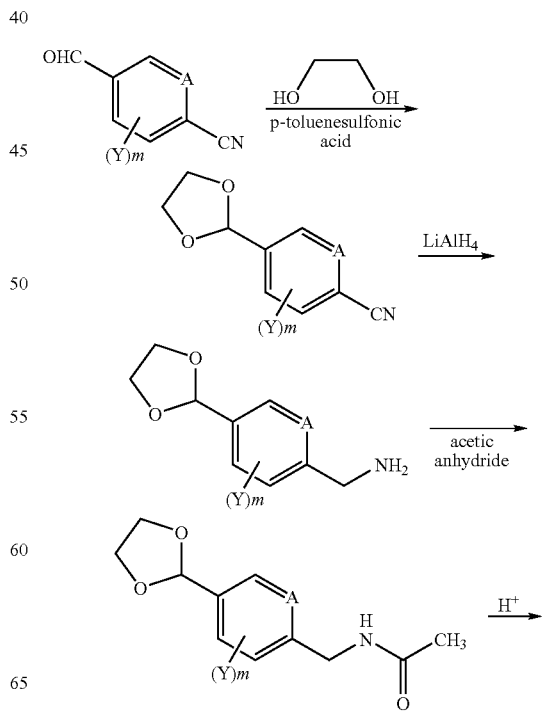

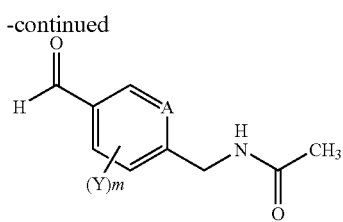

wherein A, Y and m are as defined above.

Examples of 4-cyanobenzaldehydes used as starting materials of the above reaction scheme include 4-cyanobenzaldehyde, 4-cyano-2-fluorobenzaldehyde, 2-chloro-4-cyanobenzaldehyde, 2-bromo-4-cyanobenzaldehyde, 4-cyano-2-iodobenzaldehyde, and 5-formylpyridine-2-carbonitrile. When two adjacent Y, together with the carbon atoms to which they are attached to, form an optionally substituted cycle, such as a benzene ring, an example of a starting compound of above mentioned reaction process scheme is 4-formylnaphtalene-1 carbonitrile.

The compounds of the aforementioned formula (XI) may also be synthesized by the alternative process represented by the following reaction scheme:

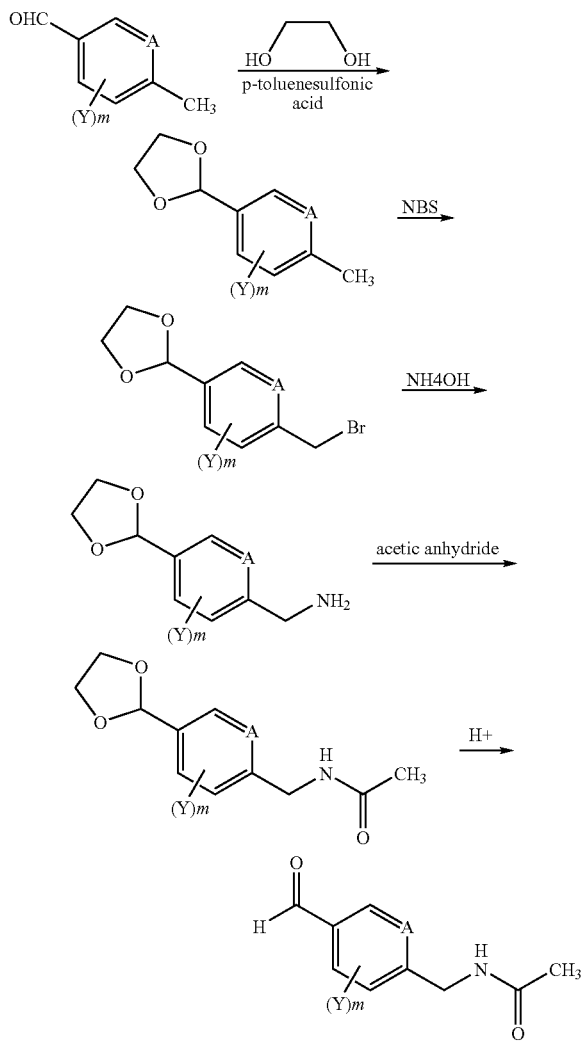

wherein A, Y and m are as defined above.

Examples of 4-methylbenzaldehydes, the starting materials of the above reaction scheme, include 3-fluoro-4-methylbenzaldehyde, 3-chloro-4-methylbenzaldehyde, 3-bromo-4-methylbenzaldehyde, 4-methyl-3-iodobenzaldehyde, 3-methoxy-4-methylbenzaldehyde, 4-methyl-3-nitrobenzaldehyde, and 6-methylnicotinealdehyde. When two adjacent Y, together with the carbon atoms to which they are attached to, form an optionally substituted cycle, such as a benzene ring, an example of a starting compound of above mentioned reaction process scheme is 4-methylnaphtalene-1-carbaldehyde.

Examples of halogenating agents in the preparation of the compounds of the aforementioned formula (II) include, for example, chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin, benzyltrimethylammonium tetrachloroiodate, sodium hypochlorite and the like.

Typical examples of the compounds of formula (II) used as starting materials in preparation process (a) include 4-(acetamidomethyl)-N-hydroxybenzene carboximidoyl chloride, 4-(acetamidomethyl)-N-hydroxy-3-methylbenzene carboximidoyl chloride, 4-(acetamidomethyl)-3-fluoro-N-hydroxybenzene carboximidoyl chloride, 4-(acetamidomethyl)-3-chloro-N-hydroxybenzene carboximidoyl chloride, 4-(acetamidomethyl)-3-bromo-N-hydroxybenzene carboximidoyl chloride, 4-(acetamidomethyl)-N-hydroxy-3-iodobenzene carboximidoyl chloride, and 4-(acetamidomethyl)-N-hydroxy-3-nitrobenzene carboximidoyl chloride.

When two adjacent Y, together with the carbon atoms to which they are attached to, form an optionally substituted cycle, such as a benzene ring, an example of a compound of formula (II) is N-({4-[(hydroxyimino)methyl]naphthalen-1-yl}methyl)acetamide.

The compounds of formula (III) used as another starting materials in preparation process (a) encompass known compounds described, for example, in the Journal of Organic Chemistry, 1991, Vol. 56, pp. 7336-7340 and 1994, Vol. 59, pp. 2898-2901; Journal of Fluorine Chemistry, 1999, Vol. 95, pp. 167-170; and WO 2005/05085216. Such compounds can be synthesized by the processes described in these publications. Typical examples of the compounds of formula (III) include [1-(trifluoromethyl)vinyl]benzene, 1,3-difluoro-5-[1-(trifluoromethyl)vinyl]benzene, 1-chloro-3-[1-(trifluoromethyl)vinyl]benzene, 1,3-dichloro-5-[1-(trifluoromethyl)vinyl]benzene, 1-trifluoromethyl-3-[1-(trifluoromethyl)vinyl]benzene, 1-trifluoromethyl-4-[1-(trifluoromethyl)-vinyl]benzene, 1,3-bis(trifluoromethyl)-5-[1-(trifluoromethyl)vinyl]benzene, 1,3-dibromo-5-[1-(trifluoromethyl)vinyl]benzene, 1,2,3-trichloro-5-[1-(trifluoromethyl)vinyl]benzene, and 1-fluoro-2-(trifluoromethyl)-4-[1-(trifluoromethyl)vinyl]benzene.

Preparation process (a) may be carried out according to the process described in WO 2004/018410, WO 2005/085216, Tetrahedron (2000), Vol. 56, pp. 1057-1064.

The reaction of preparation process (a) may be carried out in a suitable diluent, and examples thereof which may be used during the process include, for example, aliphatic hydrocarbons (e.g. hexane, cyclohexane, heptane), aromatic hydrocarbons (e.g. benzene, toluene, xylene, chlorobenzene), alcohols (e.g. methanol, ethanol, isopropanol), ethers (e.g. diethylether, dibutylether, dimethoxyethane (DME), tetrahydrofuran, dioxane, acid amides (e.g. dimethylformamide (DMF), dimethylacetamide (DMA), N-methylpyrrolidone), nitriles (e.g. acetonitrile, propionitrile), dimethyl sulfoxide (DMSO), water or mixtures thereof.

The reaction of preparation process (a) may be carried out using as a base the following: alkali metal bases including, for example, sodium carbonate, potassium carbonate, sodium hydrogen carbonate, potassium hydrogen carbonate, sodium acetate, potassium acetate, sodium methoxide, sodium ethoxide and potassium tert-butoxide; and organic bases including triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane and imidazole.

The reaction of preparation process (a) may be carried out within a substantially wide range of temperature. In general, the reaction may be carried out at a temperature of from about −78° C. to about 200° C., preferably from −10° C. to about 150° C. The reaction is preferably carried out under normal pressure, but it may be carried out under increased pressure or reduced pressure. The reaction time may 0.1 to 72 hours, preferably 1 to 24 hours.

In carrying out preparation process (a), for example, 1 mole of the compound of formula (II) may be reacted with 1 to 2 moles of the compound of formula (III) and 1 mole or slightly excess amount of a base in a diluent, for example, DMF to obtain the objective compound of formula (I).

The compounds of formula (IV) used as starting materials in preparation process (b) are novel compounds, and may be obtained by the following processes (e) to (k).

Preparation Process (e) (when $R^3$ Represents Hydrogen and n is 1 in Formula (IV)):

A process of reacting a compound represented by the formula:

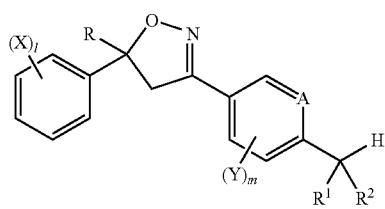

(XII)

wherein A, R, X, l, Y, m, $R^1$ and $R^2$ are as defined above, with a halogenating agent to obtain a compound represented by the formula:

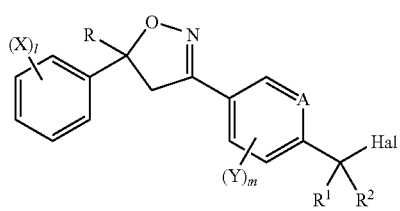

(XIII)

wherein A, R, X, l, Y, m, $R^1$ and $R^2$ are as defined above, and Hal represents halogen, reacting the resulting compound with potassium phthalimide to obtain the compound represented by the formula:

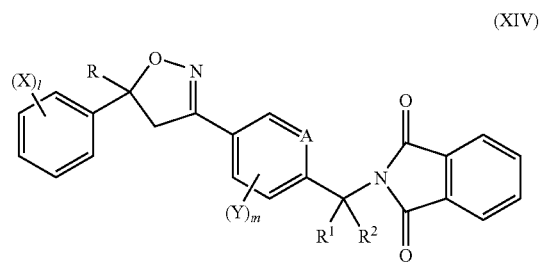

(XIV)

wherein A, R, X, l, Y, m, $R^1$ and $R^2$ are as defined above, and hydrolyzing the resulting compound.

Preparation Process (f)

A process of reacting a compound of the aforementioned formula (XIII) with a compound represented by the formula:

$$R^3\text{—}NH_2 \qquad \qquad (XV)$$

wherein $R^3$ is as defined above.

Preparation Process (g) (when n Represents 1 and $R^1$ and $R^2$ Represent Hydrogen in Formula (IV)):

A process of reducing a compound represented by the formula:

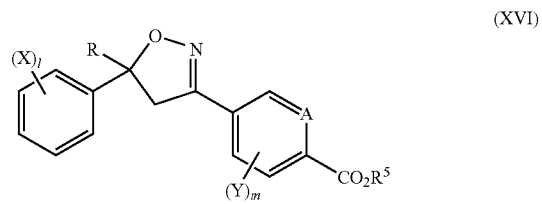

(XVI)

wherein A, R, X, l, Y and m are as defined above and $R^5$ represents alkyl to obtain a compound represented by the formula:

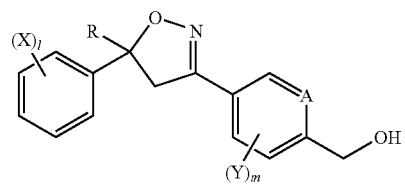

(XVII)

wherein A, R, X, l, Y and m are as defined above, reacting the resulting compound with methanesulfonyl chloride or a halogenating agent to obtain the compound represented by the formula:

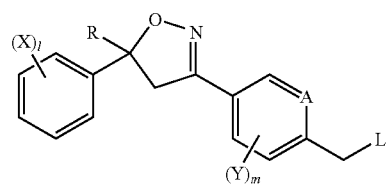

(XVIII)

wherein A, R, X, l, Y, m and L are as defined above, and subsequently reacting the resulting compound with a compound of the aforementioned formula (XV)

Preparation Process (h) (when $R^3$ Represents Hydrogen in Formula (IV)):

A process of reducing a compound represented by the formula:

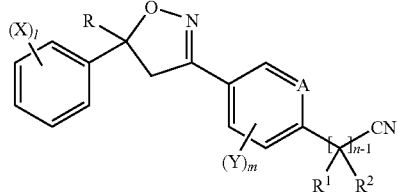
(XIX)

wherein A, R, X, l, Y, m, n, $R^1$ and $R^2$ are as defined above.

Some of the compounds of the aforementioned formula (XII) in preparation process (e) are the compounds described in WO 2005/085216, and may be obtained according to, for example, the following preparation processes (i) to (k).

Preparation Process (i)

A process of reacting a compound of the aforementioned formula (III) with a compound represented by the formula:

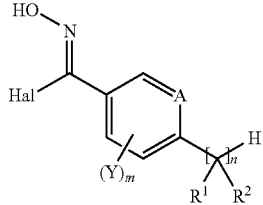
(XX)

wherein A, Y, m, n, $R^1$, $R^2$ and Hal are as defined above.

Preparation Process (j)

A process of an intramolecular cyclization of a compound represented by the formula:

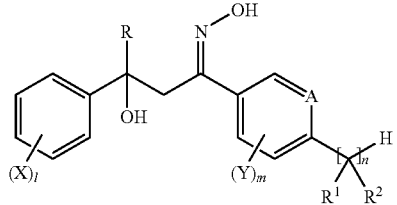
(XXI)

wherein A, R, X, l, Y, m, $R^1$ and $R^2$ are as defined above.

Preparation Process (k)

A process of reacting a compound represented by the formula:

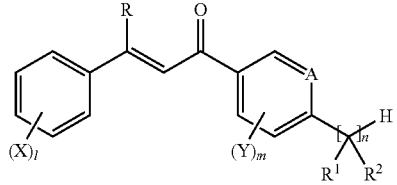
(XXII)

wherein A, R, X, l, Y, m, $R^1$ and $R^2$ are as defined above, with hydroxylamine hydrochloride.

Some of the compounds of formula (XX) in the aforementioned preparation process (i) are novel compounds, and may be obtained by, for example, a preparation processes analogous to those for the compounds of formula (II) in the aforementioned preparation process (a).

Typical examples of the compounds of formula (XX) include:

N-hydroxy-4-methylbenzene carboximidoyl chloride, 3-fluoro-N-hydroxy-4-methylbenzene carboximidoyl chloride, 3-chloro-N-hydroxy-4-methylbenzene carboximidoyl chloride, 3-bromo-N-hydroxy-4-methylbenzene carboximidoyl chloride, N-hydroxy-3-iodo-4-methylbenzene carboximidoyl chloride, and N-hydroxy-4-methyl-3-nitrobenzene carboximidoyl chloride. When two adjacent Y, together with the carbon atoms to which they are attached to, form an optionally substituted cycle, such as a benzene ring, an example of a compound of formula (XX) is N-hydroxy-4-methylnaphthalene-1-carboximidoyl chloride The aforementioned preparation process (j) may be carried out according to the methods described, for example, in J. Chem. Soc. Chem. Commun., Vol. 16, 1983, pp. 873-875; Chem. Pharm. Bull., Vol. 12, 1964, pp. 1189-1192.

Many of the compounds of the aforementioned formula (XXI) are novel compounds and may be obtained by reacting a compound represented by the formula:

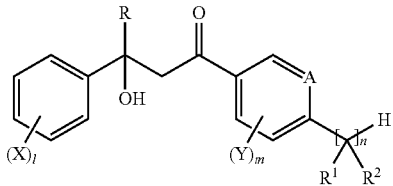
(XXIII)

wherein A, R, X, l, Y, m, $R^1$ and $R^2$ are as defined above, with hydroxylamine or salt thereof.

Many of the compounds of the aforementioned formula (XXIII) are novel compounds and may be synthesized according to the process described, for example, in Zhurnal Organicheskoi Khimii, Vol. 28 (No. 3), pp. 518-526. That is, the compound of formula (XXIII) may be obtained by reacting a compound represented by the formula:

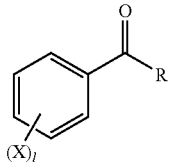
(XXIV)

wherein X, l and R are as defined above, with the compound represented by the formula:

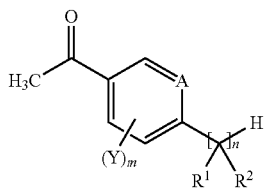

(XXV)

wherein A, Y, m, n, $R^1$ and $R^2$ are as defined above.

Typical examples of the compounds of the aforementioned formula (XXIV) include, trifluoroacetophenone, 3',5'-dichloro-2,2,2-trifluoroacetophenone, 3',4'-dichloro-2,2,2-trifluoroacetophenone, 3',4',5'-trichloro-2,2,2-trifluoroacetophenone, 3'-fluoro-2,2,2-trifluoroacetophenone, 3'-chloro-2,2,2-trifluoroacetophenone, 3'-bromo-2,2,2-trifluoroacetophenone, 3'-iodo-2,2,2-trifluoroacetophenone, 3'-nitro-2,2,2-trifluoroacetophenone, 3'-cyano-2,2,2-trifluoroacetophenone, 3'-(trifluoromethyl)-2,2,2-trifluoroacetophenone, and 3',5'-bis(trifluoromethyl)-2,2,2-trifluoroacetophenone.

Typical examples of the compounds of the aforementioned formula (XXV) include, 4-methylacetophenone, 2-fluoro-4-methylacetophenone, 2-chloro-4-methylacetophenone, 2-bromo-4-methylacetophenone, 2-iodo-4-methylacetophenone, 4-methyl-2-nitroacetophenone, methyl 4-acetylbenzoate, methyl 4-acetyl-2-nitrobenzoate, methyl 4-acetyl-2-iodobenzoate, and 4-acethylbenzonitrile. When two adjacent Y, together with the carbon atoms to which they are attached to, form an optionally substituted cycle, such as a benzene ring, an example of a compound of formula (XXV) is 1-(4-methylnaphthalen-1-yl)ethanone.

Typical examples of the compounds of the aforementioned formula (XXIII) include:
3-(3,5-dichlorophenyl)-4,4,4-trifluoro-3-hydroxy-1-(4-methylphenyl)butan-1-one, dichlorophenyl)-4,4,4-trifluoro-1-(3-fluoro-4-methylphenyl)-3-hydroxybutan-1-one, 1-(3-chloro-4-methylphenyl)-3-(3,5-dichlorophenyl)-4,4,4-trifluoro-3-hydroxybutan-1-one, 1-(3-bromo-4-methylphenyl)-3-(3,5-dichlorophenyl)-4,4,4-trifluoro-3-hydroxybutan-1-one, 3-(3,5-dichlorophenyl)-4,4,4-trifluoro-3-hydroxy-1-(3-iodo-4-methylphenyl)butan-1-one, dichlorophenyl)-4,4,4-trifluoro-3-hydroxy-1-(4-methyl-3-nitrophenyl)butan-1-one, and 4,4,4-trifluoro-3-hydroxy-1-(4-methylphenyl)-3-[3-(trifluoromethyl)phenyl]butan-1-one. When two adjacent Y, together with the carbon atoms to which they are attached to, form an optionally substituted cycle, such as a benzene ring, an example of a compound of formula (XXIII) is 3-(3,5-dichlorophenyl)-4,4,4-trifluoro-3-hydroxy-1-(4-methylnaphthalen-1-yl)butan-1-one.

The compounds of formula (XXII) in the aforementioned preparation process (k) are novel compounds and may be obtained by reacting a compound of the aforementioned formula (XXIII) with thionylchloride.

Typical examples of the compounds of formula (XXII) include: 4,4,4-trifluoro-1-(4-methylphenyl)-3-[3-(trifluoromethyl)-phenyl]but-2-en-1-one, 3-(3,5-dichlorophenyl)-4,4,4-trifluoro-1-(4-methylphenyl)but-2-en-1-one, 3-(3,5-dichlorophenyl)-4,4,4-trifluoro-1-(3-fluoro-4-methylphenyl)but-2-en-1-one, 1-(3-chloro-4-methylphenyl)-3-(3,5-dichlorophenyl)-4,4,4-trifluorobut-2-en-1-one, 1-(3-bromo-4-methylphenyl)-3-(3,5-dichlorophenyl)-4,4,4-trifluorobut-2-en-1-one, 3-(3,5-dichlorophenyl)-4,4,4-trifluoro-1-(3-iodo-4-methylphenyl)but-2-en-1-one, and 3-(3,5-dichlorophenyl)-4,4,4-trifluoro-1-(4-methyl-3-nitrophenyl)but-2-en-1-one. When two adjacent Y, together with the carbon atoms to which they are attached to, form an optionally substituted cycle, such as a benzene ring, an example of a compound of formula (XXII) is 3-(3,5-dichlorophenyl)-4,4,4-trifluoro-1-(4-methylnaphthalen-1-yl)but-2-en-1-one.

The compounds of the aforementioned formula (XV) in preparation process (f) are well known compounds and include, for example, aqueous ammonia, methylamine, ethylamine, n-propylamine, isopropylamine, cyclopropylamine, allylamine, propargylamine, benzylamine, 1-pyridin-2-yl-methanamine, 1-pyridin-3-ylmethanamine, 1-pyridin-4-il-methanamine.

The compounds of the aforementioned formula (XVI) in the preparation process (g) may be obtained by the following process (l) or (m).

Preparation Process (l)

A process of reacting a compound of the aforementioned formula (III) with a compound represented by the formula:

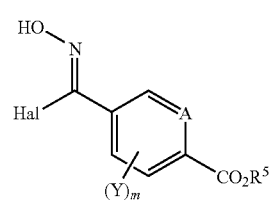

(XXVI)

wherein A, Y, m, Hal and $R^5$ are as defined above.

Preparation Process (m)

A process of an intramolecular cyclization of a compound represented by the formula:

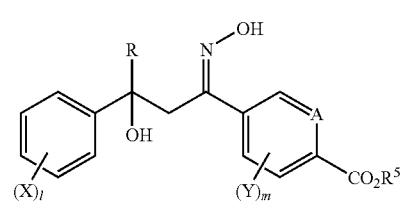

(XXVII)

wherein A, R, X, l, Y, m and $R^5$ are as defined above.

Some of the compounds of formula (XXVI) in the aforementioned preparation process (l) are novel compounds and may be obtained using, for example, a preparation process analogous to that for the compounds of formula (II) in the aforementioned preparation process (a).

Typical examples of the compounds of formula (XXVI) include: methyl 4-[chloro(hydroxyimino)methyl]benzoate, methyl 4-[chloro(hydroxyimino)methyl]-2-methylbenzoate, methyl 4-[chloro(hydroxyimino)methyl]-2-fluorobenzoate, methyl 2-chloro-4-[chloro(hydroxyimino)methyl]benzoate, methyl 2-bromo-4-[chloro(hydroxyimino)methyl]benzoate, methyl 4-[chloro(hydroxyimino)methyl]-2-iodobenzoate, and methyl 4-[chloro(hydroxyimino)methyl]-2-nitrobenzoate. When two adjacent Y, together with the carbon atoms to which they are attached, form an optionally substituted cycle, such as a benzene ring, an example of a compound of formula (XXVI) is methyl 4-[chloro(hydroxyimino)methyl] naphthalene-1-carboxylate.

The aforementioned preparation process (m) may be carried out according to a process analogous to the aforementioned preparation process (j). The compounds of the aforementioned formula (XXVII) may be obtained by reacting a compound represented by the formula:

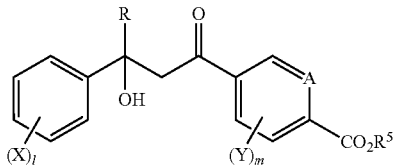

(XXVIII)

wherein A, R, X, l, Y, m and $R^5$ are as defined above, with hydroxylamine or salt thereof.

The compounds of the aforementioned formula (XXVIII) are novel compounds and may be obtained by reacting a compound of the aforementioned formula (XXIV) with the compound represented by the formula:

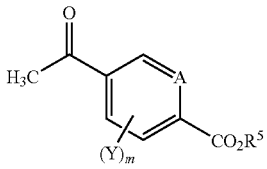

(XXIX)

wherein A, Y, m and $R^5$ are as defined above.

The compounds of the aforementioned formula (XXIX) are well known compounds and include, for example, methyl-4-acetylbenzoate, methyl-4-acetyl-2-methylbenzoate, methyl-4-acetyl-2-fluorobenzoate, methyl-4-acetyl-2-chlorobenzoate, methyl-4-acetyl-2-bromobenzoate, methyl-4-acetyl-2-iodobenzoate, and methyl-4-acetyl-2-nitrobenzoate. When two adjacent Y, together with the carbon atoms to which they are attached to, form an optionally substituted cycle, such as a benzene ring, an example of a compound of formula (XXIX) is methyl-4-acetylnaphthalene-1-carboxylate.

The compounds of formula (XIX) in the aforementioned preparation process (h) include known compounds and may be synthesized according to a process described in, for example, J. Org. Chem., 1999, Vol. 64, pp. 3171-3177.

Typical examples of the compounds of formula (XII) in the aforementioned preparation process (e) include, for example, 5-(3,5-dichlorophenyl)-3-(4-methylphenyl)-5-(trifluoromethyl)-4,5-dihydroisoxazole, 5-(3,5-dichlorophenyl)-3-(3-fluoro-4-methylphenyl)-5-(trifluoromethyl)-4,5-dihydroisoxazole, 3-(3-chloro-4-methylphenyl)-5-(3,5-dichlorophenyl)-5-(trifluoromethyl)-4,5-dihydroisoxazole, 3-(3-bromo-4-methylphenyl)-5-(3,5-dichlorophenyl)-5-(trifluoromethyl)-4,5-dihydroisoxazole, 5-(3,5-dichlorophenyl)-3-(3-iodo-4-methylphenyl)-5-(trifluoromethyl)-4,5-dihydroisoxazole, and 5-(3,5-dichlorophenyl)-3-(4-methyl-3-nitrophenyl)-5-(trifluoromethyl)-4,5-dihydroisoxazole. When two adjacent Y, together with the carbon atoms to which they are attached to, form an optionally substituted cycle, such as a benzene ring, an example of a compound of formula (XII) is 5-(3,5-dichlorophenyl)-3-(4-methylnaphthalen-1-yl)-5-(trifluoromethyl)-4,5-dihydroisoxazole.

Typical examples of the compounds of formula (XVI) in preparation process (g) include
methyl 4-[5-(3,5-dichlorophenyl)-5-(trifluoromethyl)-4,5-dihydroisoxazol-3-yl]benzoate, methyl 4-[5-(3,5-dichlorophenyl)-5-(trifluoromethyl)-4,5-dihydroisoxazol-3-yl]-2-methylbenzoate, methyl 4-[5-(3,5-dichlorophenyl)-5-(trifluoromethyl)-4,5-dihydroisoxazol-3-yl]2-fluorobenzoate, methyl 2-chloro-4-[5-(3,5-dichlorophenyl)-5-(trifluoromethyl)-4,5-dihydroisoxazol-3-yl]benzoate, methyl 2-bromo-4-[5-(3,5-dichlorophenyl)-5-(trifluoromethyl)-4,5-dihydroisoxazol-3-yl]benzoate, methyl 4-[5-(3,5-dichlorophenyl)-5-(trifluoromethyl)-4,5-dihydroisoxazol-3-yl]-2-iodobenzoate, and methyl 4-[5-(3,5-dichlorophenyl)-5-(trifluoromethyl)-4,5-dihydroisoxazol-3-yl]-2-nitrobenzoate. When two adjacent Y, together with the carbon atoms to which they are attached to, form an optionally substituted cycle, such as a benzene ring, an example of a compound of formula (XVI) is 4-[5-(3,5-dichlorophenyl)-5-(trifluoromethyl)-4,5-dihydroisoxazol-3-yl]naphthalene-1-carboxylate.

Typical examples of the compounds of formula (XIX) in preparation process (h) include
4-[5-(3,5-dichlorophenyl)-5-(trifluoromethyl)-4,5-dihydroisoxazol-3-yl]benzonitrile, 4-[5-(3,5-dichlorophenyl)-5-(trifluoromethyl)-4,5-dihydrosoxazol-3-yl]-2-methylbenzonitrile, 4-[5-(3,5-dichlorophenyl)-5-(trifluoromethyl)-4,5-dihydroisoxazol-3-yl]-2-fluorobenzonitrile, 2-chloro-4-[5-(3,5-dichlorophenyl)-5-(trifluoromethyl)-4,5-dihydroisoxazol-3-yl]benzonitrile, 2-bromo-4-[5-(3,5-dichlorophenyl)-5-(trifluoromethyl)-4,5-dihydroisoxazol-3-yl]benzonitrile, 4-[5-(3,5-dichlorophenyl)-5-(trifluoromethyl)-4,5-dihydroisoxazol-3-yl]-2-iodobenzonitrile, 4-[5-(3,5-dichlorophenyl)-5-(trifluoromethyl)-4,5-dihydroisoxazol-3-yl]-2-nitrobenzonitrile, {4-[5-(3,5-dichlorophenyl)-5-(trifluoromethyl)-4,5-dihydroisoxazol-3-yl]phenyl}acetonitrile, and {2-bromo-4-[5-(3,5-dichlorophenyl)-5-(trifluoromethyl)-4,5-dihydroisoxazol-3-yl]phenyl}acetonitrile. When two adjacent Y, together with the carbon atoms to which they are attached to, form an optionally substituted cycle, such as a benzene ring, an example of a compound of formula (XIX) is 4-[5-(3,5-dichlorophenyl)-5-(trifluoromethyl)-4,5-dihydroisoxazol-3-yl]naphthalene-1-carbonitrile.

The compounds represented by formula (V) used as starting materials in the preparation process (b) are well known compounds in the art of organic chemistry and include, for example, acetyl chloride, propionyl chloride, pivaloyl chloride, acryloyl chloride, methyl chloroformate, N,N-dimethylcarbamoyl chloride, cyclopropylcarbonyl chloride, N,N-dimethylthiocarbamoyl chloride, benzoyl chloride, nicotinoyl chloride, acetic anhydride, trifluoroacetic anhydride, methanesulfonyl chloride.

The reaction of the preparation process (b) may be carried out in a suitable diluent including, for example, aliphatic hydrocarbons (e.g. hexane, cyclohexane, heptane), aromatic hydrocarbons (e.g. benzene, toluene, xylene, chlorobenzene), ethers (e.g. diethylether, dibutylether, dimethoxyethane (DME), tetrahydrofuran, dioxane), amides (e.g. dimethylformamide (DMF), dimethylacetamide (DMA), N-methylpyrrolidone), nitriles (e.g. acetonitrile, propionitrile), dimethyl sulfoxide (DMSO), water or mixtures thereof.

The reaction of preparation process (b) may be carried out using as a base the following: alkali metal bases including lithium hydride, sodium hydride, potassium hydride, lithium amide, sodium amide, lithium diisopropylamide, butyl lithium, tert-butyl lithium, trimethylsilyl lithium, lithium hexamethyldisilazide, sodium carbonate, potassium carbonate, sodium acetate, potassium acetate, sodium methoxide, sodium ethoxide, potassium-tert-butoxide; and organic bases including triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole.

The reaction of preparation process (b) may be carried out in a wide range of temperature. In general, the reaction may be carried out at temperature of from about −78° C. to about 200° C., preferably from about −10° C. to about 150° C. The reaction is preferably carried out under normal pressure, ie. of about 1000 mbar, but it may be carried out under increased, ie. pressure above 1000 mbar, or reduced pressure, ie. pressure below 1000 mbar. The reaction time may be in the range from 0.1 to 72 hours, preferably 0.1 to 24 hours.

In carrying out preparation process (b), for example, 1 mole of the compound of formula (IV) may be reacted with 1 to 3 moles of the compound of formula (V) in the presence of 1 mole to 3 moles of a base in a diluent, for example DMF, to obtain the objective compound of formula (I).

The compounds of formula (VI) used as starting materials in preparation process (c) are novel compounds and may be obtained, for example, by the following processes (n) to (p).
Preparation Process (n)
A process of reacting a compound represented by the formula:

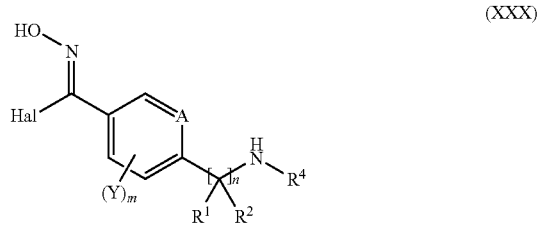

(XXX)

wherein A, Y, m, n, $R^1$, $R^2$, $R^4$ and Hal are as defined above, with a compound of the aforementioned formula (III).
Preparation Process (o)
A process of reacting a compound represented by the formula:

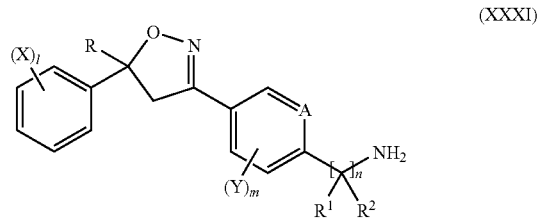

(XXXI)

wherein A, R, X, l, Y, m, n, $R^1$ and $R^2$ are as defined above, with a compound of the aforementioned formula (VII).
Preparation Process (p)
A process of reacting a compound represented by the aforementioned formula (VIII) with a compound represented by the formula:

$R^4$—$NH_2$     (XXXII)

wherein $R^4$ is as defined above.

The compounds of formula (XXX) in the aforementioned preparation process (n) are novel compounds and may be obtained by a process analogous to the preparation process for the compounds of formula (II) in the aforementioned preparation process (a).

Typical examples of the compounds of formula (XXX) include, for example:
4-(formamidomethyl)-N-hydroxybenzene carboximidoyl chloride, 4-(acetamidomethyl)-N-hydroxybenzene carboximidoyl chloride, 4-(acetamidomethyl)-N-hydroxy-3-methylbenzene carboximidoyl chloride, 4-(acetamidomethyl)-3-fluoro-N-hydroxybenzene carboximidoyl chloride, 4-(acetamidomethyl)-3-chloro-N-hydroxybenzene carboximidoyl chloride, 4-(acetamidomethyl)-3-bromo-N-hydroxybenzene carboximidoyl chloride, 4-(acetamidomethyl)-N-hydroxy-3-iodobenzene carboximidoyl chloride, and 4-(acetamidomethyl)-N-hydroxy-3-nitrobenzene carboximidoyl chloride. When two adjacent Y, together with the carbon atoms to which they are attached to, form an optionally substituted cycle, such as a benzene ring, an example of a compound of formula (XXX) is 4-[(acetylamino)methyl]-N-hydroxynaphthalene-1-carboximidoyl chloride.

The compound of formula (XXXI) in the aforementioned preparation process (o) corresponds to the compound of the aforementioned formula (IV) wherein $R^3$ is hydrogen.

The compounds of formula (XXXII) in preparation process (p) are well known compounds and include, for example, formamide, acetamide, propionamide, 2,2,2-trifluoroacetamide, benzamide, ethylcarbamate, and ethanethioamide.

The reaction of preparation process (c) may be carried out under the same conditions as those in the aforementioned preparation process (b).

Some of the compounds represented by formula (VIII) used as starting materials in preparation process (d) correspond to some of the compounds of the aforementioned formulas (XIII) and (XVIII).

Amide compounds of the aforementioned formula (IX) are known compounds, and include, for example acetamide, 2,2, 2-trifluoroacetamide, 2,2,2-trifluoro-N-methylacetamide, and pyrrolidin-2-one, piperidin-2-one, N-(pyridin-2-ylmethyl)acetamide.

The reaction of preparation process (d) may be carried out in the same conditions as those of the aforementioned preparation process (b).

The compounds according to the present invention have potent insecticidal and acaricidal activity. Therefore, the compounds represented by formula (I) or formula (Ia) of the present invention can be used as insecticides and acaricides. They are particularly useful in the agricultural field. The compounds according to the present invention also exert an appropriate controlling effect against harmful insects without phytotoxicity against cultured plants. In addition, the compounds of the present invention can be used for controlling a wide variety of pests including, for example, harmful sucking insects, biting insects and other plant-parasitic pests, stored grain pests and hygienic pests as well as pests in the veterinary field and can be applied for their control, in particular eradication and extermination. Therefore, the present invention also encompasses a method for combating harmful pests.

The compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, in the hygiene and animal health sector. They may be preferably employed as plant protection agents. They are active against normally sensitive and resistant species and against all or some stages of development. The pests which can be combated by using the compounds and compositions according to the invention include inter alia:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro*, *Aceria sheldoni*, *Aculops* spp., *Aculus* spp., *Amblyomma* spp., *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Hemitarsonemus* spp., *Hyalomma* spp., *Ixodes* spp., *Latrodectus mactans*, *Metatetranychus* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.; as well as *Callosobruchus Chinensis*, *Sitophilus zeamais*, *Tribolium Castaneum*, *Epilachna vigintioctomaculata*, *Agriotes fuscicollis*, *Anomala rufocuprea*, *Leptinotarsa decemlineata*, *Diabrotica* spp., *Monochamus alternatus*, *Lissorhoptrus oryzophilus*, *Lyctus bruneus*, and *Aulacophora femoralis*.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.; as well as *Musca domestica*, *Aedes aegypti*, *Hylemia platura*, *Culex pipiens*, *Anopheles sinensis*, *Culex tritaeniorhychus* and *Liriomyza trifolii*.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahibergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.; as well as *Reticulitermes speratus* and *Coptotermes formosanus.*

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.; as well as *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis, Heliothis virescens* and *Phyllocnistis citrella.*

From the order of the Orthoptera, for example, *Acheta domesticus, Blatta orientalis, Gryllotalpa* spp., *Leucophaea maderae, Locusta* spp., *Melanoplus* spp., *Schistocerca gregaria*; as well as *Blattella germanica, Periplaneta americana, Gryllotalpa africana* and *Locusta migratoria migratoriaodes.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Franidiniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.; as well as *Thrips palmi* and *Franldiniella occidentalis.*

From the order of Hemiptera, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nazara* spp., *Trialeurodes vaporariorm* and *Pshylla* spp.;

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Radopholus similis, Rotylenchus* spp., *Trichodorus* spp., *Tylenchorhynchus* spp., *Tylenchulus* spp., *Tylenchulus semipenetrans, Xiphinema* spp.; as well as *Meloidogyne incognita, Bursaphelenchus lignicolus Mamiya et Kiyohara, Aphelenchoides besseyi,* and *Heterodera glycines* and *Pratylenchus* spp.

Mites include, for example, *Tetranychus cinnabarinus, Tetranychus urticae, Panonychus citri, Aculops pelekassi* and *Tarsonemus* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

In the field of veterinary medicine, the novel compounds of the present invention can be effectively used against various harmful animal parasites (ectoparasites and endoparasites) like for example insects and helminths.

Examples of such animal parasites include the following pests:

Insects including, for example, *Gastrophilus* spp., *Stomoxys* spp., *Trichodectes* spp., *Rhodnius* spp., *Ctenocephalides canis, Cimex lecturius, Ctenocephalides felis* and *Lucilia cuprina;*

Acarids including, for example, *Ornithodoros* spp., *Ixodes* spp. and *Boophilus* (now referred to as *Rhipicephalus*) spp.

As already mentioned before, in the veterinary fields, i.e. in the field of veterinary medicine, the active compounds according to the present invention are active against animal parasites, in particular ectoparasites or endoparasites. The term endoparasites includes in particular helminths, such as cestodes, nematodes or trematodes, and protozoae, such as coccidia. Ectoparasites are typically and preferably arthropods, in particular insects such as flies (stinging and licking), parasitic fly larvae, sucking lice, biting lice, fleas and the like; or acarids, such as ticks, for example hard ticks or soft ticks, or mites, such as scab mites, harvest mites, bird mites and the like.

These parasites include:

From the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;* from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi;* from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haemato-* bia spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca;* from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis;* from the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp. (e.g. *Suppella longipalpa*);

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus (Boophilus)* spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;* from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic Mange, Pneumonyssoides caninum, Acarapis woodi.*

The active compounds according to the invention are also suitable for controlling arthropods, helminths and protozoae, which attack animals. The control of arthropods is preferred. The control of insects is particularly preferred. Equally, the control of acarids is particularly preferred.

Animals which may be treated to control the parasites include birds, insects and in particular mammals. Animals include agricultural livestock such as, for example, cattle, sheep, goats, horses, pigs, donkeys, camels, buffaloes, rabbits, chickens, fur-bearing animals, turkeys, ducks, geese, cultured fish, honeybees. Moreover, animals include domestic animals—also referred to as companion animals—such as, for example, dogs, cats, ferrets, cage birds, aquarium fish, reptiles and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it is desirable to prevent or interrupt the uptake of blood by the parasites from the hosts (when applicable). Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

The active compounds of the present invention, when used as insecticides, may be formed into conventional formulation forms. Such formulation forms include, for example, solutions, emulsions, wettable powders, water dispersible granules, suspensions, powders, foams, pastes, tablets, granules, aerosols, active compound-impregnated natural and synthetic substances, microcapsules, seed coating agents, formulations used with burning device (burning devices include, for example, fumigation and smoking cartridges, cans and coils) and UVL [cold mist, warm mist].

These formulations may be prepared according to known methods. For example, they can be prepared by mixing the active compounds with extenders, i.e. liquid diluents or carriers; liquefied gas diluents or carriers; solid diluents or carriers, and, optionally by using surfactants i.e. emulsifiers and/or dispersants and/or foam-forming agents. The formulations are prepared in advance in suitable facilities or directly before or during the application.

Suitable for use as auxiliaries are substances which are suitable for imparting to the compounds and compositions itself and/or to preparations derived therefrom (for example spray liquors, seed dressings) particular properties such as certain technical properties and/or also particular biological properties. Typical suitable auxiliaries are: extenders, solvents or diluents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents.

Suitable solid carriers are for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Liquid diluents, solvents or carriers include, for example, aromatic hydrocarbons (for example, xylene, toluene, alkylnaphthalene), chlorinated aromatic or chlorinated aliphatic hydrocarbons (for example, chlorobenzens, ethylene chlorides, methylene chlorides), aliphatic hydrocarbons [for example, cyclohexanes or paraffins (for example, mineral oil fractions or vegetable oils)], alcohols (for example, butanol, glycol and their ethers or esters), ketones (for example, acetone, methylethylketone, methylisobutylketone, cyclohexanone), strongly polar solvents (for example, dimethylformamide, dimethyl sulfoxide) and water.

Liquefied gas diluents or carriers include substances which are present as gases at normal temperature and pressure, and include, for example, aerosol propellants such as furan, propane, nitrogen gas, carbon dioxide and halogenated hydrocarbons.

Solid diluents include, for example, ground natural minerals (for example, kaolin, clay, talc, chalk, quartz, attapulgite, montmorillonite or diatomaceous earth) and ground synthetic minerals (for example, highly-dispersive silicic acid, alumina, silicate).

Solid carriers for granules include, for example, crushed and fractionated rocks (for example, calcite, marble, pumice stone, sepiolite, dolomite), synthetic granules of inorganic or organic powders, and fine particles of organic materials (for example, sawdust, coconut shells, maize cob, tobacco stalks).

Emulsifiers and/or foam-forming agents include, for example, nonionic or anionic emulsifiers [for example, polyoxyethylene fatty acid esters, polyoxyethylene fatty alcohol ethers (for example, alkylaryl polyglycol ether), alkyl sulfonates, alkyl sulfates, aryl sulfonates], and albumin hydrolysis products.

Dispersants include, for example, lignin sulfite waste liquor and methylcellulose.

Binding agents may also be used in the formulations (powders, granules, emulsions) and include, for example, carboxymethylcellulose and natural or synthetic polymers (for example, gum Arabic, polyvinyl alcohol, polyvinyl acetate).

Colorants may be used and include, for example, inorganic pigments (e.g. iron oxide, titanium oxide, Prussian Blue), organic dyes (e.g. alizarin dyes, azo dyes or metal phthalocyanine dyes) and trace elements (e.g. salts of iron, manganese, boron, copper, cobalt, molybdenum and zinc).

Other possible auxiliaries are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

In general, formulations according to the invention may contain the above-enumerated active components at an amount ranging from 0.1 to 95% by weight, preferably from 0.5 to 90% by weight.

The active compounds according to the present invention may exist in combination with other active compounds, for example, insecticides, toxic baits, bactericides, acaricides, nematicides, fungicides, growth regulating agents, herbicides in the form of commercially useful formulations or in the application forms prepared from such formulations. The aforementioned insecticides include, for example, organophosphorus agents, carbamate agents, carboxylate agents, chlorinated hydrocarbon type agents, insecticidal substances produced by microorganisms.

In addition, the active compounds according to the present invention may exist as mixed agents with synergists, and such formulations and application forms include commercially useful ones. The synergists are not necessarily active per se, but can enhance the action of the active compounds.

The content of the active compound according to the present invention in a commercially useful application form may vary in a wide range.

The concentration of the active compound according to the present invention for application may be in the range of from 0.0000001 to 100% by weight, preferably in the range of from 0.00001 to 1% by weight.

The compounds according to the present invention may be used in ordinary manners suitable for their application forms. It is understood that the compounds according to the invention can also be present in compositions containing further ingredients, such as auxiliaries or active ingredients. The skilled person will choose a suitable ingredient among those named herein and known in the art and which are supposed to enhance a property which is considered being favorable in view of the intended application and use.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts", "parts of plants" and "plant parts" have been explained above.

Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive "synergistic" effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds or compositions according to the invention. The preferred ranges stated above for the active compounds or compositions also apply to the treatment of these plants. Particular emphasis is given to the treatment of plants with the compounds or compositions specifically mentioned in the present text.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, a combination with other suitable active compounds, such as phosphoric esters, carbamates, pyrethroids, neonicotinoids, growth regulators or active compounds from other known classes of insecticides can be used and is especially preferable.

The compounds or compositions according to the invention, preferable in their suitable application form, can be used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

The compounds or compositions according to the invention are particularly suitable for treating seed. A large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seed of plants has been known for a long time and is subject-matter of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and also the germinating plant with a minimum of crop protection agents being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the resulting plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

Furthermore, it must be considered as advantageous that the compounds or compositions according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally be protected by the compositions according to the invention against damage.

The compounds or compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*.

The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The active compounds of the present invention, when used against hygienic pests and stored grain pests, have a good stability to alkali on calcareous substances and also show an excellent residual activity in wood and soil.

Generally, when used for the treatment of animals the active compounds according to the invention can be applied directly. Preferably they are applied as pharmaceutical compositions which may contain pharmaceutically acceptable excipients and/or auxiliaries which are known in the art.

In the veterinary field and in animal keeping, the active compounds are applied (=administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols, unpressurized sprays, for example pump sprays and atomizer sprays.

When used for livestock, poultry, domestic animals and the like, the active compounds according to the present invention can be applied as formulations (for example powders, wettable powders ["WP"], emulsions, emulsifiable concentrates ["EC"], flowables, homogeneous solutions and suspension concentrates ["SC"]) which comprise the active compounds in an amount of from 1 to 80% by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

The present invention will be illustrated more specifically by examples. The present invention, however, should not be limited only to these examples.

SYNTHESIS EXAMPLE 1

N-{4-[5-(3,5-dichlorophenyl)-5-(trifluoromethyl)-4,5-dihydroisoxazol-3-yl]benzyl}acetamide (No. 1-1)

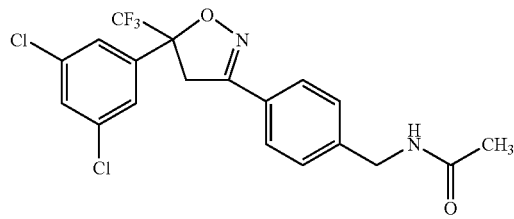 [SMILES: CC(=O)NCc1ccc(C2=NOC(c3cc(Cl)cc(Cl)c3)(C(F)(F)F)C2)cc1]

SYNTHESIS EXAMPLE 1-1

Synthesis of 4-methylbenzaldehyde oxime

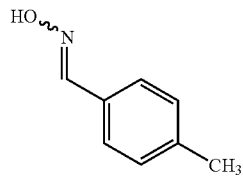

A solution of 4-methylbenzaldehyde (5 g), hydroxylamine hydrochloride (4.34 g) and sodium acetate (6.23 g) in ethanol and water was stirred for one hour at room temperature. After the reaction solution was diluted with t-butylmethylether, the solution was washed with water and saturated brine. The organic layer was dried over anhydrous magnesium sulfate. The solvent was distilled off under reduced pressure to obtain 4-methylbenzaldehyde oxime (5 g).

1H-NMR (CDCl3) δ: 2.37 (3H, s), 7.19 (2H, d), 7.46 (2H, d), 8.12 (1H, s)

SYNTHESIS EXAMPLE 1-2

Synthesis of [5-(3,5-dichlorophenyl)-3-(4-methylphenyl)-5-(trifluoromethyl)-4,5-dihydroisoxazole

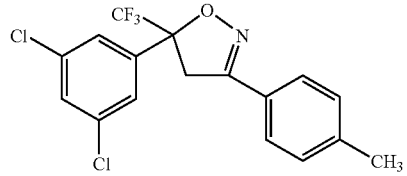 [SMILES: Cc1ccc(C2=NOC(c3cc(Cl)cc(Cl)c3)(C(F)(F)F)C2)cc1]

A solution of 4-methylbenzaldehyde oxime (2 g) and N-chlorosuccinimide (2.17 g) in dimethylformamide (20 mL) was stirred for one hour at 55° C. After the reaction solution was diluted with t-butylmethylether, the solution was washed with water and saturated brine. The organic layer was dried over anhydrous magnesium sulfate. The solvent was distilled off under reduced pressure to obtain N-hydroxy-4-methylbenzene carboximidoyl chloride (2 g). A solution of resultant N-hydroxy-4-methylbenzene carboximidoyl chloride and 1,3-dichloro-5-[1-(trifluoromethyl)-vinyl]benzene (5.3 g) in toluene (50 mL) was heated to reflux for 8 hours. The solvent was distilled off under reduced pressure, and the residue was purified by silica gel chromatography to obtain [5-(3,5-dichlorophenyl) 3-(4-methylphenyl)-5-(trifluoromethyl)-4,5-dihydroisoxazole (5.0 g).

1H-NMR (CDCl3) δ: 2.37 (3H, s), 3.87 (2H, dd), 7.22-7.25 (3H, m), 7.51-7.56 (4H, m).

SYNTHESIS EXAMPLE 1-3

Synthesis of 3-[4-(bromomethyl)phenyl]-5-(3,5-dichlorophenyl)-5-(trifluoromethyl)-4,5-dihydroisoxazole

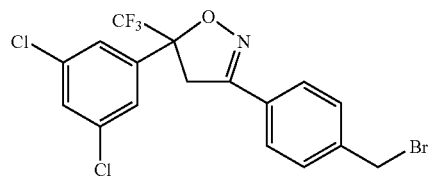 [SMILES: FC(F)(F)C1(c2cc(Cl)cc(Cl)c2)CC(c2ccc(CBr)cc2)=NO1]

A solution of 5-(3,5-dichlorophenyl)-3-(4-methylphenyl)-5-(trifluoromethyl)-4,5-dihydroisoxazole (5.3 g), N-bromosuccinimide (3.7 g) and 2,2'-azobisisobutylonitrile (0.1 g) in dichloroethane (40 mL) was heated to reflux for 3 hours. After the solvent was distilled off under reduced pressure, the residue was diluted with t-butylmethylether, and the solution was washed with water and saturated brine. The organic layer was dried over anhydrous magnesium sulfate. The solvent was distilled off under reduced pressure, and the residue was then purified by silica gel chromatography to obtain 3-[4-(bromomethyl)phenyl]-5-(3,5-dichlorophenyl)-5-(trifluoromethyl)-4,5-dihydroisoxazole (2.5 g).

1H-NMR (CDCl3) δ: 3.66-4.10 (2H, m), 4.49 (2H, s), 7.26-7.69 (7H, m).

SYNTHESIS EXAMPLE 1-4

Synthesis of 2-{4-[5-(3,5-dichlorophenyl)-5-(trifluoromethyl)-4,5-dihydroisoxazol-3-yl]benzyl}-1H-isoindol-1,3(2H)-dione

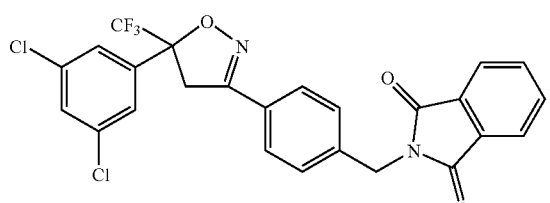

A solution of 3-[4-(bromomethyl)phenyl]-5-(3,5-dichlorophenyl)-5-(trifluoromethyl)-4,5-dihydroisoxazole (1.5 g) and potassium phthalimide (0.61 g) in N,N-dimethylformamide (20 mL) was stirred for 8 hours at room temperature. After the reaction solution was diluted with t-butylmethylether, the solution was washed with water and saturated brine.

The organic layer was dried over anhydrous magnesium sulfate. The solvent was distilled off under reduced pressure, and the residue was then purified by silica gel chromatography to obtain 3-[4-(bromomethyl)phenyl]-5-(3,5-dichlorophenyl)-5-(trifluoromethyl)-4,5-dihydroisoxazole (0.8 g).

1H-NMR (CDCl3) δ: 3.85 (2H, dd), 4.87 (2H, s), 7.40-7.89 (13H, m).

SYNTHESIS EXAMPLE 1-5

Synthesis of 1-{4-[5-(3,5-dichlorophenyl)-5-(trifluoromethyl)-4,5-dihydroisoxazol-3-yl]phenyl}methanamine

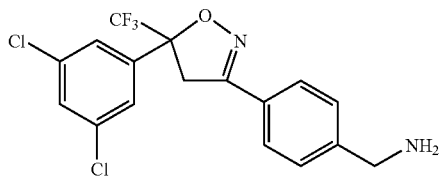 [SMILES: NCc1ccc(C2=NOC(c3cc(Cl)cc(Cl)c3)(C(F)(F)F)C2)cc1]

A solution of 2-{4-[5-(3,5-dichlorophenyl)-5-(trifluoromethyl)-4,5-dihydroisoxazol-3-yl]benzyl}-1H-isoindole-1,3(2H)-dione (0.65 g) and aqueous hydrazine solution (0.07 g) in methanol (5 mL) was refluxed for one hour. After the reaction solution was diluted with t-butylmethylether, the solution was washed with water and saturated brine. The organic layer was dried over anhydrous magnesium sulfate. The solvent was distilled off under reduced pressure, and the residue was then purified by silica gel chromatography to yield 1-{4-[5-(3,5-dichlorophenyl)-5-(trifluoromethyl)-4,5-dihydroisoxazol-3-yl]phenyl}methanamine (0.2 g).

1H-NMR (CDCl3) δ: 3.89 (2H, dd), 4.47 (2H, s), 7.39-7.40 (3H, m), 7.52-7.52 (2H, m), 7.61-7.63 (2H, m).

SYNTHESIS EXAMPLE 1-6

Synthesis of N-{4-[5-(3,5-dichlorophenyl)-5-(trifluoromethyl)-4,5-dihydroisoxazol-3-yl]benzyl}acetamide

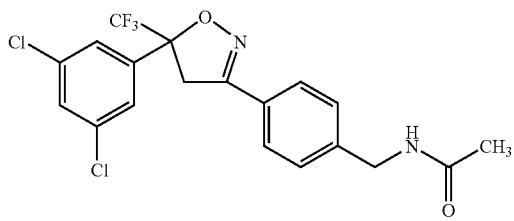 [SMILES: CC(=O)NCc1ccc(C2=NOC(c3cc(Cl)cc(Cl)c3)(C(F)(F)F)C2)cc1]

To a solution of 1-{4-[5-(3,5-dichlorophenyl)-5-(trifluoromethyl)-4,5-dihydroisoxazol-3-yl]phenyl}methanamine (0.2 g) and triethylamine (0.08 g) in tetrahydrofuran (5 mL), acetyl chloride (0.05 g) was added dropwise and the mixture was stirred for one hour at room temperature. After the reaction solution was diluted with t-butylmethylether, the solution was washed with water and saturated brine. The organic layer was dried over anhydrous magnesium sulfate. The solvent was distilled off under reduced pressure, and the residue was then purified by silica gel chromatography to obtain N-{4-[5-(3,5-dichlorophenyl)-5-(trifluoromethyl)-4,5-dihydroisoxazol-3-yl]benzyl}acetamide (0.05 g).

1H-NMR (CDCl3) δ: 2.04 (3H, s), 3.88 (2H, dd), 4.45 (2H, d), 6.06 (1H, s), 7.32 (2H, d), 7.42-7.42 (1H, m), 7.49-7.52 (2H, m), 7.59-7.62 (2H, m)

SYNTHESIS EXAMPLE 2

N-{4-[5-(3,5-dichlorophenyl)-5-(trifluoromethyl)-4,5-dihydroisoxazol-3-yl]benzyl}acetamide (No. 1-1)

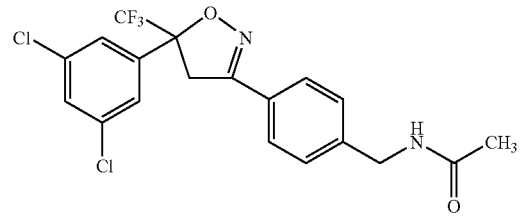 [SMILES: CC(=O)NCc1ccc(C2=NOC(c3cc(Cl)cc(Cl)c3)(C(F)(F)F)C2)cc1]

SYNTHESIS EXAMPLE 2-1

Synthesis of N-{4-[(hydroxyimino)methyl]benzyl}acetamide

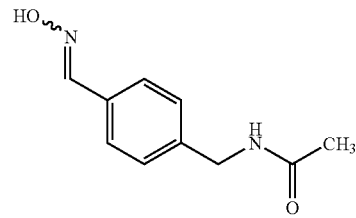

A solution of N-(4-formylbenzyl)acetamide (1.7 g), hydroxylamine hydrochloride (1.0 g) and sodium acetate (1.0 g) in ethanol (10 mL) and water (6 mL) was stirred for one hour at room temperature. After the reaction solution was diluted with t-butylmethylether, the solution was washed with water and saturated brine. The organic layer was dried over anhydrous magnesium sulfate. The solvent was distilled off under reduced pressure to yield crude N-{4-[(hydroxyimino)methyl]-benzyl}acetamide (1.8 g).

SYNTHESIS EXAMPLE 2-2

Synthesis of N-{4-[5-(3,5-dichlorophenyl)-5-(trifluoromethyl)-4,5-dihydroisoxazol-3-yl]benzyl}acetamide

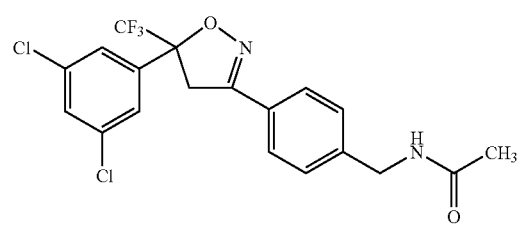 [SMILES: CC(=O)NCc1ccc(C2=NOC(c3cc(Cl)cc(Cl)c3)(C(F)(F)F)C2)cc1]

N-{4-[(hydroxyimino)methyl]benzyl}acetamide (0.5 g) was dissolved in N,N-dimethylformamide (20 mL), N-chlorosuccinimide (0.38 g) was added to this solution, and the mixture was stirred for two hours at room temperature. To the reaction solution, 1,3-dichloro-5-[1-(trifluoromethyl)vinyl]benzene (0.75 g) was added, and after the mixture was cooled to 0° C., a solution of triethylamine (0.58 g) in N,N-dimethylformamide (2 mL) was added dropwise to the mixture, which was then stirred for 8 hours at room temperature. After addition of water and extraction with ethyl acetate, the organic layer was washed with saturated brine and dried over anhydrous magnesium sulfate. The solvent was distilled off under reduced pressure, and the residue was then purified by silica gel chromatography to yield N-{4-[5-(3,5-dichlorophenyl)-5-(trifluoromethyl)-4,5-dihydroisoxazol-3-yl]benzyl}acetamide (0.3 g).

1H-NMR (CDCl3) δ: 2.04 (3H, s), 3.88 (2H, dd), 4.45 (2H, d), 6.06 (1H, s), 7.32 (2H, d), 7.42-7.42 (1H, m), 7.49-7.52 (2H, m), 7.59-7.62 (2H, m)

SYNTHESIS EXAMPLE 3

N-{2-bromo-4-[5-(3,5-dichlorophenyl)-5-(trifluoromethyl)-4,5-dihydroisoxazol-3-yl]benzyl}-N-(pyridin-2-ylmethyl)acetamide (No. 1-15)

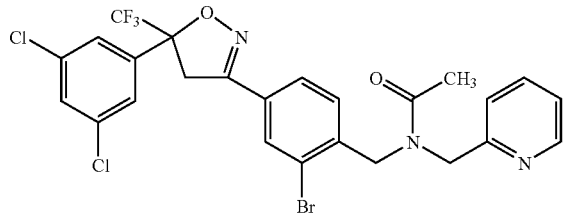 [SMILES: CC(=O)N(Cc1ccccn1)Cc1ccc(C2=NOC(c3cc(Cl)cc(Cl)c3)(C(F)(F)F)C2)cc1Br]

SYNTHESIS EXAMPLE 3-1

Synthesis of 3-[3-bromo-4-(bromomethyl)phenyl]-5-(3,5-dichlorophenyl)-5-(trifluoromethyl)-4,5-dihydroisoxazole

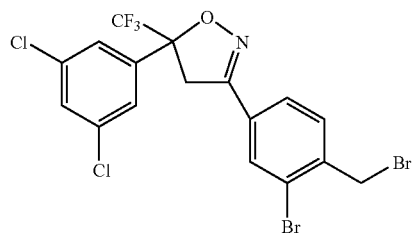 [SMILES: FC(F)(F)C1(c2cc(Cl)cc(Cl)c2)CC(c2ccc(CBr)c(Br)c2)=NO1]

A solution of 3-(3-bromo-4-methylphenyl)-5-(3,5-dichlorophenyl)-5-(trifluoromethyl)-4,5-dihydroisoxazole (1.2 g), N-bromosuccinimide (0.54 g) and 2,2'-azobisisobutylonitrile (0.05 g) in dichloroethane (20 mL) was heated to reflux for 3 hours. The solvent was distilled off under reduced pressure, the residue was diluted with t-butylmethylether, and the solution was washed with water and saturated brine. The organic layer was dried over anhydrous magnesium sulfate. The solvent was distilled off under reduced pressure, and the residue was purified by silica gel chromatography to yield 3-[3-bromo-4-(bromomethyl)-phenyl]-5-(3,5-dichlorophenyl)-5-(trifluoromethyl)-4,5-dihydroisoxazole (1.0 g).

1H-NMR (CDCl3) δ: 3.86 (2H, dd), 4.59 (2H, s), 7.46-7.61 (5H, m), 7.85-7.86 (1H, m).

SYNTHESIS EXAMPLE 3-2

Synthesis of 1-{2-bromo-4-[5-(3,5-dichlorophenyl)-5-(trifluoromethyl)-4,5-dihydroisoxazol-3-yl]phenyl}-N-(pyridin-2-ylmethyl)methanamine

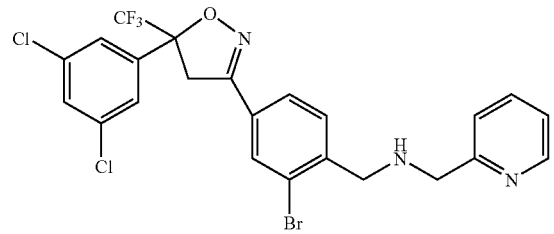 [SMILES: FC(F)(F)C1(c2cc(Cl)cc(Cl)c2)CC(c2ccc(CNCc3ccccn3)c(Br)c2)=NO1]

A solution of 3-[3-bromo-4-(bromomethyl)phenyl]-5-(3,5-dichlorophenyl)-5-(trifluoromethyl)-4,5-dihydroisoxazole (1.8 g), 2-aminomethylpyridine (0.38 g) and potassium carbonate (0.97 g) in acetonitrile (20 mL) was heated to reflux for 3 hours. After the reaction solution was diluted with t-butylmethylether, the solution was washed with water and saturated brine. The organic layer was dried over anhydrous magnesium sulfate. The solvent was distilled off under reduced pressure, and the residue was purified by silica gel chromatography to yield 1-{2-bromo-4-[5-(3,5-dichlorophenyl)-5-(trifluoromethyl)-4,5-dihydroisoxazol-3-yl]phenyl}-N-(pyridin-2-ylmethyl)methanamine (1.0 g).

1H-NMR (CDCl3) δ: 3.67 (1H, d), 3.95-3.96 (4H, m), 4.03-4.09 (1H, m), 7.17-7.19 (1H, m), 7.31-7.34 (1H, m), 7.43-7.43 (1H, m), 7.49-7.52 (2H, m), 7.57-7.58 (2H, m), 7.62-7.69 (1H, m), 7.82-7.85 (1H, m), 8.56-8.58 (1H, m).

SYNTHESIS EXAMPLE 3-3

Synthesis of N-{2-bromo-4-[5-(3,5-dichlorophenyl)-5-(trifluoromethyl)-4,5-dihydroisoxazol-3-yl]benzyl}-N-(pyrodin-2-ylmethyl)acetamide

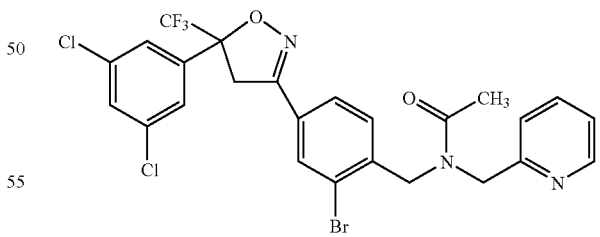

To a solution of 1-{2-bromo-4-[5-(3,5-dichlorophenyl)-5-(trifluoromethyl)-4,5-dihydroisoxazol-3-yl]phenyl}-N-(pyridin-2-ylmethyl)methanamine (0.22 g) and triethylamine (0.06 g) in tetrahydrofuran (5 mL), acetylchloride (0.04 g) was added dropwise, and the mixture was stirred one hour at room temperature. After the reaction solution was diluted with t-butylmethylether, the solution was washed with water and saturated brine. The organic layer was dried over anhydrous magnesium sulfate. The solvent was distilled off under reduced pressure, and the residue was then purified by silica gel chromatography to yield N-{2-bromo-4-[5-(3,5-dichlorophenyl)-5-(trifluoromethyl)-4,5-dihydroisoxazol-3-yl]benzyl}-N-(pyrodin-2-ylmethyl)acetamide (0.15 g).

1H-NMR (CDCl3) δ: 2.10-2.22 (3H, m), 3.63-4.13 (2H, m), 4.63-4.74 (4H, m), 7.14-7.90 (9H, m), 8.51-8.59 (1H, m)

SYNTHESIS EXAMPLE 4

Synthesis of N-{4-[5-(3,5-dichlorophenyl)-5-(trifluoromethyl)-4,5-dihydroisoxazol-3-yl]-2-nitrobenzyl}acetamide (1-60)

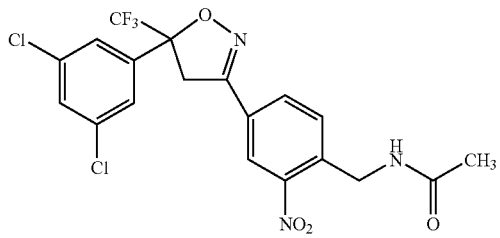 [SMILES: CC(=O)NCc1ccc(C2=NOC(c3cc(Cl)cc(Cl)c3)(C(F)(F)F)C2)cc1[N+](=O)[O-]]

SYNTHESIS EXAMPLE 4-1

Synthesis of 4-methyl-3-nitrobenzaldehyde

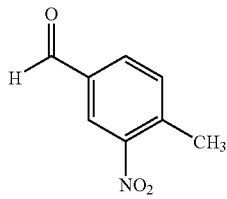

A solution of 4-methyl-3-nitrobenzoylchloride (5.5 g) in dioxane (30 mL) was added dropwise to a solution of water (30 mL), dioxane (30 mL) and sodium borohydride (2.5 g) under ice cooling. The reaction solution was refluxed for one hour, and after cooling, the solution was filtered through Celite. Water was added to the filtrate, the mixture was extracted with ethyl acetate, and the organic layer was dried over anhydrous magnesium sulfate. The solvent was distilled off under reduced pressure to obtain a crude product of (4-methyl-3-nitrophenyl)methanol (4 g).

This crude product was dissolved in dichloromethane (200 mL), manganese dioxide (20 g) was added to the solution, and the mixture was stirred for 10 hours at room temperature. After suction filtration of the reaction mixture, the solvent was distilled off under reduced pressure, and the residue was then purified by silica gel chromatography to yield 4-methyl-3-nitrobenzaldehyde (3.5 g).

1H-NMR (CDCl3) δ: 2.70 (3H, s), 7.55 (1H, d), 8.03 (1H, dd), 8.46 (1H, d), 10.04 (1H, s).

SYNTHESIS EXAMPLE 4-2

Synthesis of 5-(3,5-dichlorophenyl)-3-(4-methyl-3-nitrophenyl)-5-(trifluoromethyl)-4,5-dihydroisoxazole

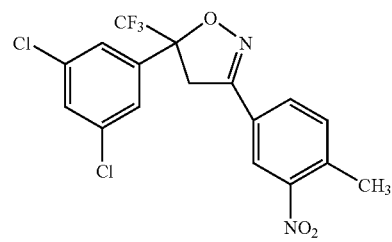 [SMILES: Cc1ccc(C2=NOC(c3cc(Cl)cc(Cl)c3)(C(F)(F)F)C2)cc1[N+](=O)[O-]]

A solution of 4-methyl-3-nitrobenzaldehyde (3.5 g) in tetrahydrofuran (50 mL) was added dropwise to a solution of hydroxylamine hydrochloride (3.0 g) and sodium acetate (4.0 g) in tetrahydrofuran (50 mL) and water (50 mL) under ice cooling, and, on completion of the dropwise addition, the mixture was stirred for one hour at room temperature. The reaction solution was diluted with water and then extracted with ethyl acetate, and the organic layer was dried over anhydrous magnesium sulfate. The solvent was distilled off under reduced pressure to obtain a crude product of 4-methyl-3-nitrobenzaldehyde oxime (3.5 g).

This crude product was dissolved in N,N-dimethylformamide (30 mL), and N-chlorosuccinimide (1.4 g) was added to the solution, and the mixture was stirred for one hour at 55° C. After finishing the stirring, 1,3-dichloro-5-[1-(trifluoromethyl)vinyl]benzene (2.5 g), triethylamine (1.2 g) was added to the mixture under ice cooling, and the mixture was stirred for 10 hours at room temperature. The reaction solution was diluted with water and then extracted with ethyl acetate, and the organic layer was dried over anhydrous magnesium sulfate. The solvent was distilled off under reduced pressure, and the residue was then purified by silica gel chromatography to yield 5-(3,5-dichlorophenyl)-3-(4-methyl-3-nitrophenyl)-5-(trifluoromethyl)-4,5-dihydroisoxazole (2.1 g).

1H-NMR (CDCl3) δ: 2.63 (3H, s), 3.72 (1H, d), 4.10 (1H, d), 7.43-7.51 (4H, m), 7.88-7.91 (1H, m), 8.15-8.16 (1H, m).

SYNTHESIS EXAMPLE 4-3

Synthesis of 3-[4-(bromomethyl)-3-nitrophenyl]-5-(3,5-dichlorophenyl)-5-(trifluoromethyl)-4,5-dihydroisoxazole

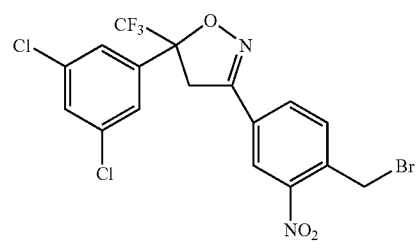 [SMILES: O=[N+]([O-])c1cc(C2=NOC(c3cc(Cl)cc(Cl)c3)(C(F)(F)F)C2)ccc1CBr]

A solution of 5-(3,5-dichlorophenyl)-3-(4-methyl-3-nitrophenyl)-5-(trifluoromethyl)-4,5-dihydroisoxazole (1.9 g), N-bromosuccinimide (0.9 g) and 2,2'-azobisisobutylonitrile (0.1 g) in dichloroethane was heated to reflux for 3 hours. The reaction solution was washed with water, and the organic layer was dried over anhydrous magnesium sulfate. The solvent was distilled off under reduced pressure, and the residue was then purified by silica gel chromatography to yield 3-[4-(bromomethyl)-3-nitrophenyl]-5-(3,5-dichlorophenyl)-5-(trifluoromethyl)-4,5-dihydroisoxazole (1.2 g).

1H-NMR (CDCl3) δ: 3.73 (1H, d), 4.11 (1H, d), 4.84 (2H, s), 7.44-7.68 (4H, m), 7.97-8.00 (1H, m), 8.24-8.24 (1H, m).

SYNTHESIS EXAMPLE 4-4

Synthesis of 1-{4-[5-(3,5-dichlorophenyl)-5-(trifluoromethyl)-4,5-dihydroisoxazol-3-yl]-2-nitrophenyl}methanamine

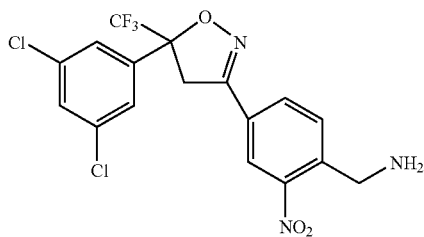 [SMILES: NCc1ccc(C2=NOC(c3cc(Cl)cc(Cl)c3)(C(F)(F)F)C2)cc1[N+](=O)[O-]]

A solution of 3-[4-(bromomethyl)-3-nitrophenyl]-5-(3,5-dichlorophenyl)-5-(trifluoromethyl)-4,5-dihydroisoxazole (1.0 g) in tetrahydrofuran (10 mL) was added dropwise to a solution of 28% ammonia (aqueous solution, 5 mL) and tetrabutyl ammonium iodide (0.05 g) in tetrahydrofuran (10 mL) and methanol (20 mL) under ice cooling, and the mixture was then stirred for 10 hours at room temperature. The reaction solution was diluted with water, and then extracted with ethyl acetate, and the organic layer was dried over anhydrous magnesium sulfate. The solvent was distilled off under reduced pressure, and the residue was then purified by silica gel chromatography to yield 1-{4-[5-(3,5-dichlorophenyl)-5-(trifluoromethyl)-4,5-dihydroisoxazol-3-yl]-2-nitrophenyl}methanamine (0.8 g).

1H-NMR (CDCl3) δ: 3.74 (1H, d), 3.94-4.18 (3H, m), 7.43-7.52 (3H, m), 7.77-7.79 (1H, m), 7.97-8.00 (1H, m), 8.20-8.24 (1H, m).

SYNTHESIS EXAMPLE 4-5

Synthesis of N-{4-[5-(3,5-dichlorophenyl)-5-(trifluoromethyl)-4,5-dihydroisoxazol-3-yl]-2-nitrobenzyl}acetamide (1-60)

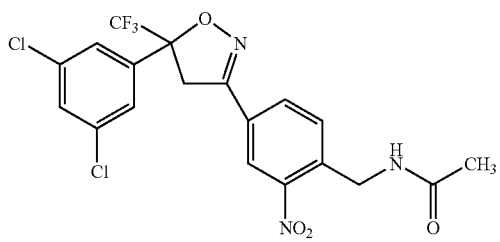 [SMILES: CC(=O)NCc1ccc(C2=NOC(c3cc(Cl)cc(Cl)c3)(C(F)(F)F)C2)cc1[N+](=O)[O-]]

To a solution of 1-{4-[5-(3,5-dichlorophenyl)-5-(trifluoromethyl)-4,5-dihydroisoxazol-3-yl]-2-nitrophenyl}methanamine (0.3 g) and acetic anhydride (0.1 g) in dichloromethane (50 mL), a solution of triethylamine (0.1 g) in dichloromethane (5 mL) was added dropwise under ice cooling, and the mixture was then stirred for one hour at room temperature. The reaction solution was diluted with water, and the organic layer was then dried over anhydrous magnesium sulfate. The solvent was distilled off under reduced pressure, and the residue was then purified by silica gel chromatogaphy to yield N-{4-[5-(3,5-dichlorophenyl)-5-(trifluoromethyl)-4,5-dihydroisoxazol-3-yl]-2-nitrobenzyl}acetamide (0.2 g).

1H-NMR (CDCl3) δ: 2.04 (3H, s), 3.72 (1H, d), 4.11 (1H, d), 4.69 (2H, d), 6.27-6.29 (1H, m), 7.45-7.49 (3H, m), 7.80-7.91 (2H, m), 8.29 (1H, d)

SYNTHESIS EXAMPLE 5

N-{4-[5-(3,5-dichlorophenyl)-5-(trifluoromethyl)-4,5-dihydroisoxazol-3-yl]-2-methylbenzyl}acetamide (No. 1-63)

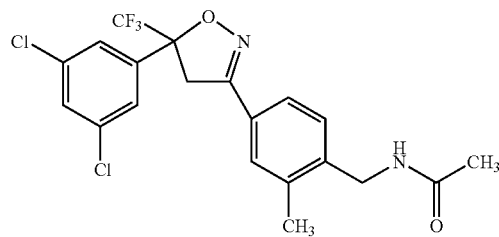 [SMILES: CC(=O)NCc1ccc(C2=NOC(c3cc(Cl)cc(Cl)c3)(C(F)(F)F)C2)cc1C]

SYNTHESIS EXAMPLE 5-1

Synthesis of methyl 4-formyl-2-methylbenzoate

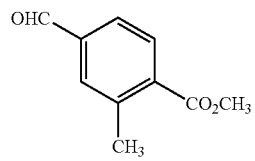

To a solution of 4-bromo-2-methylbenzoic acid (10 g) in tetrahydrofuran (100 mL), a solution of 1.6M n-butyl lithium in hexane (60 mL) was added at −70° C. After the reaction mixture was stirred for one hour at −40° C., a solution of N,N-dimethylformamide (10 mL) in tetrahydrofuran (10 mL) was added to the mixture at −70° C. After stirred for one hour at −70° C. and then warmed to room temperature, the mixture was poured onto ice and diluted with water. The aqueous layer was washed with hexane and acidified with concentrated hydrochloric acid, and the precipitate was extracted with ethyl acetate. The organic layer was dried over anhydrous magnesium sulfate. The solvent was distilled off under reduced pressure to obtain a crude product of 4-formyl-2-methylbenzoic acid (5 g).

This crude product was dissolved in dichloromethane (50 mL), and methanol (15.0 g), 1-ethyl-3-(3-dimethylaminopropyl)carbodiimide hydrochloride (12.0 g), N,N-dimethylaminopyridine (8.0 g) was added to the solution, and the mixture was stirred for 10 hours at room temperature. The reaction mixture was washed with 2N hydrochloric acid, and the organic layer was dried over anhydrous magnesium sulfate. The solvent was distilled off under reduced pressure, and the residue was then purified by silica gel chromatography to obtain methyl 4-formyl-2-methylbenzoate (1.3 g).

1H-NMR (CDCl3) δ: 2.64 (3H, s), 3.90 (3H, s), 7.73-7.76 (2H, m), 7.98-8.02 (1H, m), 10.07 (1H, s).

SYNTHESIS EXAMPLE 5-2

Synthesis of methyl 4-[5-(3,5-dichlorophenyl)-5-(trifluoromethyl)-4,5-dihydroisoxazol-3-yl]-2-methylbenzoate

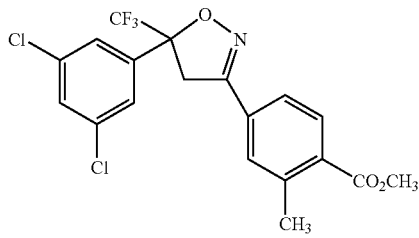 [SMILES: COC(=O)c1ccc(C2=NOC(c3cc(Cl)cc(Cl)c3)(C(F)(F)F)C2)cc1C]

A solution of methyl 4-formyl-2-methylbenzoate (1.3 g) in tetrahydrofuran (50 mL) was added dropwise to a solution of hydroxylamine hydrochloride (1.0 g), sodium acetate (1.2 g) in tetrahydrofuran (50 mL) and water (50 mL) under ice cooling, and after finishing the dropwise addition, the mixture was stirred for one hour at room temperature. The reaction mixture was diluted with water and then extracted with ethyl acetate, and the organic layer was dried over anhydrous magnesium sulfate. The solvent was distilled off under reduced pressure to obtain a crude product of methyl 4-[(hydroxyimino)methyl]-2-methylbenzoate (1.3 g).

This crude product was dissolved in N,N-dimethylformamide (30 mL), and N-chlorosuccinimide (1.0 g) was then added to the solution, and the mixture was stirred for one hour at 55° C. After finishing the stirring, 1,3-dichloro-5-[1-(trifluoromethyl)vinyl]benzene (1.7 g) and triethylamine (0.8 g) was added to the mixture under ice cooling, and the mixture was then stirred for 10 hours at room temperature. The reaction mixture was diluted with water and then extracted with ethyl acetate, and the organic layer was dried over anhydrous magnesium sulfate. The solvent was distilled off under reduced pressure, and the residue was then purified by silica gel chromatography to obtain methyl 4-[5-(3,5-dichlorophenyl)-5-(trifluoromethyl)-4,5-dihydroisoxazol-3-yl]-2-methylbenzoate (1.9 g).

1H-NMR (CDCl3) δ: 2.63 (3H, s), 3.68 (1H, d), 3.91 (3H, s), 4.11 (2H, d), 7.42-7.54 (5H, m), 7.95-7.96 (1H, m).

SYNTHESIS EXAMPLE 5-3

Synthesis of 1-{4-[5-(3,5-dichlorophenyl)-5-(trifluoromethyl)-4,5-dihydroisoxazol-3-yl]-2-methylphenyl}methanamine

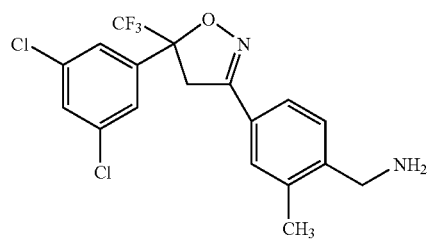 [SMILES: Cc1cc(C2=NOC(c3cc(Cl)cc(Cl)c3)(C(F)(F)F)C2)ccc1CN]

A solution of methyl 4-[5-(3,5-dichlorophenyl)-5-(trifluoromethyl)-4,5-dihydroisoxazol-3-yl]-2-methylbenzoate (1.0 g) in tetrahydrofuran (30 mL) was added dropwise to a solution of lithium aluminum hydride (0.1 g) in tetrahydrofuran (50 mL) under ice cooling, and, after finishing the addition, the mixture was stirred for one hour at room temperature. The reaction solution was poured onto ice, and then 2N hydrochloric acid (30 mL) was added by portions. The mixture was extracted with ethyl acetate, and the organic layer was dried over anhydrous magnesium sulfate. The solvent was distilled off under reduced pressure to obtain a crude product of {4-[5-(3,5-dichlorophenyl)-5-(trifluoromethyl)-4,5-dihydroisoxazol-3-yl]-2-methylphenyl}methanol (0.9 g).

This crude product was dissolved in dichloromethane (50 mL), and triethylamine (0.3 g) was added to the solution. Then a solution of methanesulfonate chloride (0.3 g) in dichloromethane (10 mL) was added dropwise under ice cooling, and the mixture was stirred for one hour at room temperature. The reaction mixture was washed with water, and the organic layer was dried over anhydrous magnesium sulfate. The solvent was distilled off under reduced pressure, and the residue was then purified by silica gel chromatography to obtain a crude product of 4-[5-(3,5-dichlorophenyl)-5-(trifluoromethyl)-4,5-dihydroisoxazol-3-yl]-2-methylbenzyl methanesulfonate (1.0 g).

The solution of this crude product in tetrahydrofuran (10 mL) was added dropwise to an aqueous solution of 28% ammonia (5 mL) and tetrabutyl ammonium iodide (0.05 g) in tetrahydrofuran (10 mL) and methanol (20 mL) under ice cooling, and the mixture was stirred for 10 hours at room temperature. After the reaction mixture was diluted with water and then extracted with ethyl acetate, and the organic layer was dried over anhydrous magnesium sulfate. The solvent was distilled off under reduced pressure, and the residue was then purified by silica gel chromatography to obtain 1-{4-[5-(3,5-dichlorophenyl)-5-(trifluoromethyl)-4,5-dihydroisoxazol-3-yl]-2-methylphenyl}methanamine (0.4 g).

1H-NMR (CDCl3) δ: 2.39 (3H, d), 3.69 (1H, d), 3.89 (2H, s), 4.11 (1H, d), 7.42-7.49 (6H, m).

SYNTHESIS EXAMPLE 5-4

Synthesis of N-{4-[5-(3,5-dichlorophenyl)-5-(trifluoromethyl)-4,5-dihydroisoxazol-3-yl]-2-methylbenzyl}acetamide

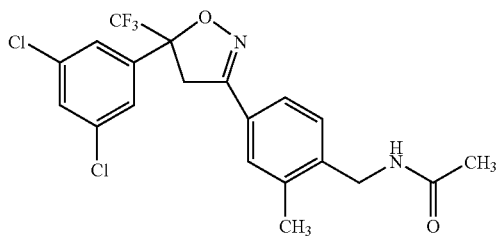 [SMILES: CC(=O)NCc1ccc(C2=NOC(c3cc(Cl)cc(Cl)c3)(C(F)(F)F)C2)cc1C]

To a solution of 1-{4-[5-(3,5-dichlorophenyl)-5-(trifluoromethyl)-4,5-dihydroisoxazol-3-yl]-2-methylphenyl}methanamine (0.2 g) and acetic anhydride (0.1 g) in dichloromethane (50 mL), triethylamine (0.1 g) in dichloromethane (5 mL) was added dropwise under ice cooling, and the mixture was then stirred for one hour at room temperature. The reaction mixture was washed with water, and the organic layer was dried over anhydrous magnesium sulfate. The solvent was distilled off under reduced pressure, and the residue was then purified by silica gel chromatography to yield N-{4-[5-(3,5-dichlorophenyl)-5-(trifluoromethyl)-4,5-dihydroisoxazol-3-yl]-2-methylbenzyl}acetamide (0.2 g).

1H-NMR (CDCl3) δ: 2.04 (3H, s), 3.68 (1H, d), 4.07 (1H, d), 4.45 (2H, d), 5.61-5.64 (1H, m), 7.19-7.27 (3H, m), 7.43-7.50 (3H, m)

SYNTHESIS EXAMPLE 6

N-(cyano{4-[5-(3,5-dichlorophenyl)-5-(trifluoromethyl)-4,5-dihydroisoxazol-3-yl]phenyl}methyl)-N-(pyridin-2-ylmethyl)-acetamide (No. 1-11)

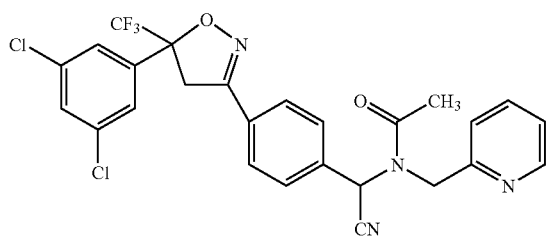 [SMILES: CC(=O)N(Cc1ccccn1)C(C#N)c1ccc(C2=NOC(c3cc(Cl)cc(Cl)c3)(C(F)(F)F)C2)cc1]

SYNTHESIS EXAMPLE 6-1

4-[5-(3,5-dichlorophenyl)-5-(trifluoromethyl)-4,5-dihydroisoxazol-3-yl]benzaldehyde

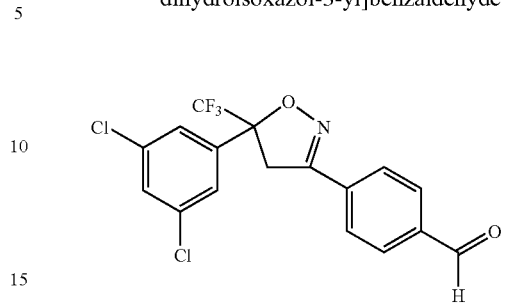

To a solution of {4-[5-(3,5-dichlorophenyl)-5-(trifluoromethyl)-4,5-dihydroisoxazol-3-yl]phenyl}methanol (1 g) in methylene chloride (30 mL), activated manganese oxide (1.8 g) was added, and the mixture was then heated and stirred for 3 hours at 40° C. After filtration of the reaction mixture through Celite, the resultant filtrate was concentrated under reduced pressure to yield 4-[5-(3,5-dichlorophenyl)-5-(trifluoromethyl)-4,5-dihydroisoxazol-3-yl]benzaldehyde (0.8 g).

1H-NMR (CDCl3) δ: 3.79-4.07 (2H, m), 7.43-7.44 (1H, m), 7.51-7.52 (2H, m), 7.83-7.85 (2H, m), 7.94-7.96 (2H, m), 10.06 (1H, s)

SYNTHESIS EXAMPLE 6-2

Synthesis of {4-[5-(3,5-dichlorophenyl)-5-(trifluoromethyl)-4,5-dihydroisoxazol-3-yl]phenyl}[(pyridin-2-ylmethyl)-amino]acetonitrile

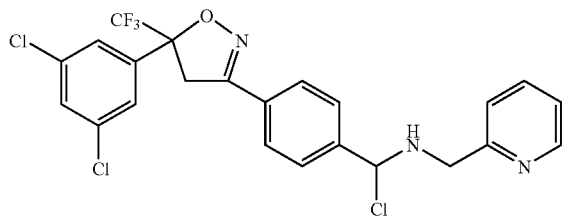 [SMILES: FC(F)(F)C1(c2cc(Cl)cc(Cl)c2)CC(c2ccc(C(Cl)NCc3ccccn3)cc2)=NO1]

To a solution of 4-[5-(3,5-dichlorophenyl)-5-(trifluoromethyl)-4,5-dihydroisoxazol-3-yl]benzaldehyde (0.30 g), 2-aminomethylpyridine (0.09 g) and trimethylsilylcyanide (0.08 g) in tetrahydrofuran (5 mL), lithium perchlorate (0.8 g) was added, and the mixture was then stirred for one hour at room temperature. After the reaction mixture was diluted with t-butylmethylether, the solution was washed with water and saturated brine. The organic layer was dried over anhydrous magnesium sulfate. The solvent was distilled off under reduced pressure, and the residue was then purified by silica gel chromatography to obtain {4-[5-(3,5-dichlorophenyl)-5-(trifluoromethyl)-4,5-dihydroisoxazol-3-yl]phenyl}[(pyridin-2-ylmethyl)amino]acetonitrile (0.15 g)

1H-NMR (CDCl3) δ: 3.65-3.83 (5H, m), 7.05-7.57 (11H, m).

SYNTHESIS EXAMPLE 6-3

N-(cyano{4-[5-(3,5-dichlorophenyl)-5-(trifluoromethyl)-4,5-dihydroisoxazol-3-yl]phenyl}methyl)-N-(pyridin-2-ylmethyl)acetamide

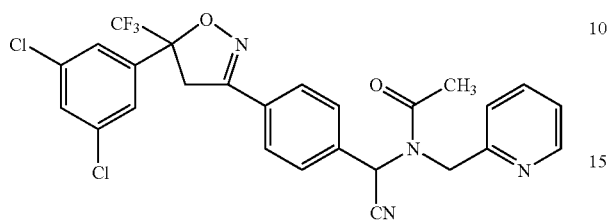

To a solution of {4-[5-(3,5-dichlorophenyl)-5-(trifluoromethyl)-4,5-dihydroisoxazol-3-yl]phenyl}[(pyridin-2-yl)methyl]amino]acetonitrile (0.05 g) and triethylamine (0.05 g) in tetrahydrofuran (5 mL), acetyl chloride (0.03 g) was added dropwise, and the mixture was stirred for one hour at room temperature. After the reaction mixture was diluted with t-butylmethylether, the solution was washed with water and saturated brine. The organic layer was dried over anhydrous magnesium sulfate. The solvent was distilled off under reduced pressure, and the residue was then purified by silica gel chromatography to yield N-(cyano{4-[5-(3,5-dichlorophenyl)-5-(trifluoromethyl)-4,5-dihydroisoxazol-3-yl]phenyl}methyl)-N-(pyridin-2-ylmethyl)acetamide (0.10 g).

1H-NMR (CDCl3) δ: 2.28 (3H, s), 3.86 (2H, dd), 4.54-4.64 (2H, m), 6.99-7.01 (1H, m), 7.13-7.16 (2H, m), 7.43-7.61 (8H, m), 8.48-8.50 (1H, m)

SYNTHESIS EXAMPLE 7

Synthesis of N-{2-bromo-4-[5-(3,5-dichlorophenyl)-5-(trifluoromethyl)-4,5-dihydroisoxazol-3-yl]benzyl}ethanethioamide (1-44)

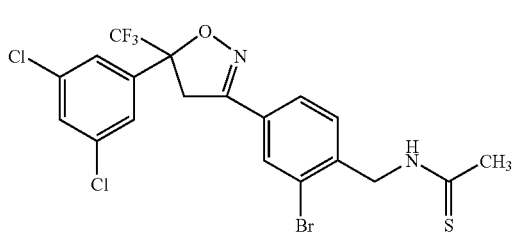 [SMILES: CC(=S)NCc1ccc(C2=NOC(c3cc(Cl)cc(Cl)c3)(C(F)(F)F)C2)cc1Br]

3-[3-bromo-4-(bromomethyl)phenyl]-5-(3,5-dichlorophenyl)-5-(trifluoromethyl)-4,5-dihydroisoxazole (0.3 g) was mixed with thioacetamide (0.04 g), and the mixture was then stirred for one hour at 80° C. The residue was purified by silica gel chromatography to yield N-{2-bromo-4-[5-(3,5-dichlorophenyl)-5-(trifluoromethyl)-4,5-dihydroisoxazol-3-yl]benzyl}ethanethioamide (0.09 g).

1H-NMR (CDCl3) δ: 2.60 (3H, s), 3.66-4.09 (2H, m), 4.97 (2H, d), 7.43-7.60 (6H, m), 7.87 (1H, d)

SYNTHESIS EXAMPLE 8

Synthesis of 1-{2-bromo-4-[5-(3,5-dichlorophenyl)-5-(trifluoromethyl)-4,5-dihydroisoxazol-3-yl]benzyl}-4-methyl-1,4-dihydro-5H-tetrazol-5-one (No. 1-55)

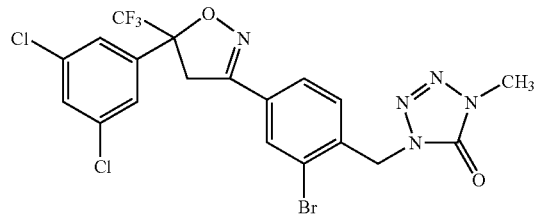 [SMILES: Cn1nnn(Cc2ccc(C3=NOC(c4cc(Cl)cc(Cl)c4)(C(F)(F)F)C3)cc2Br)c1=O]

A solution of 3-[3-bromo-4-(bromomethyl)phenyl]-5-(3,5-dichlorophenyl)-5-(trifluoromethyl)-4,5-dihydroisoxazole (0.3 g), 1-methyl-1,4-dihydro-5H-tetrazol-5-one (0.06 g) and potassium carbonate (0.16 g) in N,N-dimethylformamide (10 mL) was stirred for 3 hours at room temperature. After the reaction mixture was diluted with t-butylmethylether, the solution was washed with water and saturated brine. The organic layer was dried over anhydrous magnesium sulfate. The solvent was distilled off under reduced pressure, and the residue was then purified by silica gel chromatography to yield 1-{2-bromo-4-[5-(3,5-dichlorophenyl)-5-(trifluoromethyl)-4,5-dihydroisoxazol-3-yl]benzyl}-4-methyl-1,4-dihydro-5H-tetrazol-5-one (0.1 g).

1H-NMR (CDCl3) δ: 3.65-4.08 (5H, m), 5.24 (2H, s), 7.28-7.30 (1H, m), 7.42-7.43 (1H, m), 7.49-7.50 (2H, m), 7.60-7.62 (1H, m), 7.89-7.89 (1H, m).

SYNTHESIS EXAMPLE 9

Synthesis of N-{2-cyano-4-[5-(3,5-dichlorophenyl)-5-(trifluoromethyl)-4,5-dihydroisoxazol-3-yl]benzyl}-N-(pyridin-2-ylmethyl)acetamide (1-61)

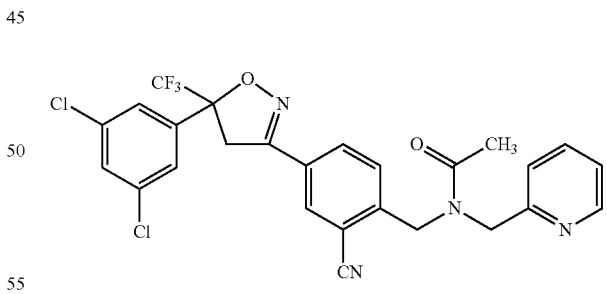

To a solution of N-{2-bromo-4-[5-(3,5-dichlorophenyl)-5-(trifluoromethyl)-4,5-dihydroisoxazol-3-yl]benzyl}-N-(pyrodin-2-ylmethyl)acetamide (0.75 g) in dimethylformamide (20 mL), zinc cyanide (0.11 g) and paradium tetrakistriphenyl phosphine (0.29 g) was added in argon atmosphere, and the mixture was then stirred for 4 hours at 80° C. After the reaction mixture was diluted with t-butylmethylether, the solution was washed with water and saturated brine. The organic layer was dried over anhydrous magnesium sulfate. The solvent was distilled off under reduced pressure, and the residue was then purified by silica gel chromatography to yield N-{2-cyano-4-[5-(3,5-dichlorophenyl)-5-(trifluoromethyl)-4,5-dihydroisoxazol-3-yl]benzyl}-N-(pyridin-2-ylmethyl)acetamide (0.6 g).

1H-NMR (CDCl3) δ: 2.27-2.31 (3H, m), 3.75-4.06 (2H, m), 4.68-4.87 (4H, m), 7.17-7.96 (9H, m), 8.49-8.57 (1H, m).

SYNTHESIS EXAMPLE 10

Synthesis of 3-(4-methylphenyl)-5-(trifluoromethyl)-5-[3-(trifluoromethyl)phenyl]-4,5-dihydroisoxazole

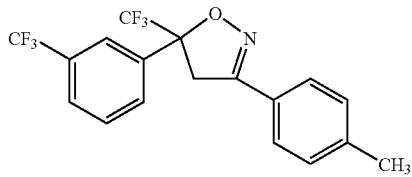 [SMILES: Cc1ccc(C2=NOC(c3cccc(C(F)(F)F)c3)(C(F)(F)F)C2)cc1]

SYNTHESIS EXAMPLE 10-1

4,4,4-trifluoro-3-hydroxy-1-(4-methylphenyl)-3-[3-(trifluoromethyl)phenyl]butan-1-one

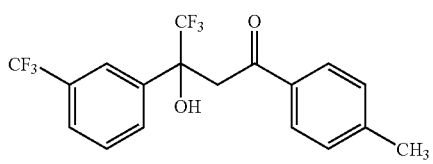 [SMILES: Cc1ccc(C(=O)CC(O)(c2cccc(C(F)(F)F)c2)C(F)(F)F)cc1]

A solution of 2,2,2-trifluoro-1-[3-(trifluoromethyl)-phenyl]ethanone (3.0 g), 4-methylacetophenone (1.1 g) and lithium hydride (0.13 g) in tetrahydrofuran (30 mL) was stirred for 3 hours at 60° C. After the reaction solution was diluted with t-butylmethylether, the solution was washed with water and saturated brine. The organic layer was dried over anhydrous magnesium sulfate. The solvent was distilled off under reduced pressure, and the residue was then purified by silica gel chromatography to yield 4,4,4-trifluoro-3-hydroxy-1-(4-methylphenyl)-3-[3-(trifluoromethyl)phenyl]butan-1-one (3.0 g).

1H-NMR (CDCl3) δ: 2.44 (3H, s), 3.67-3.94 (2H, m), 5.96 (1H, s), 7.39-7.78 (8H, m).

SYNTHESIS EXAMPLE 10-2

4,4,4-trifluoro-3-hydroxy-1-(4-methylphenyl)-3-[3-(trifluoromethyl)phenyl]butan-1-one oxime

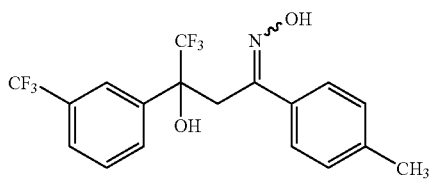 [SMILES: Cc1ccc(C(CC(O)(c2cccc(C(F)(F)F)c2)C(F)(F)F)=NO)cc1]

A solution of 4,4,4-trifluoro-3-hydroxy-1-(4-methylphenyl)-3-[3-(trifluoromethyl)phenyl]butan-1-one (1.0 g), hydroxylamine hydrochloride (0.28 g) and pyridine (0.42 g) in ethanol (10 mL) was heated to reflux for 5 hours. After the reaction solution was diluted with t-butylmethylether, the solution was washed with water and saturated brine. The organic layer was dried over anhydrous magnesium sulfate. The solvent was distilled off under reduced pressure to yield 4,4,4-trifluoro-3-hydroxy-1-(4-methylphenyl)-3-[3-(trifluoromethyl)phenyl]butan-1-one oxime (1.0 g).

1H-NMR (CDCl3) δ: 2.30 (3H, s), 3.39 (1H, t, J=6.8 Hz), 4.02 (1H, d, J=13.6 Hz), 5.25 (1H, s), 6.94-7.69 (8H, m).

SYNTHESIS EXAMPLE 10-3

3-(4-methylphenyl)-5-(trifluoromethyl)-5-[3-(trifluoromethyl)-phenyl]-4,5-dihydroisoxazole

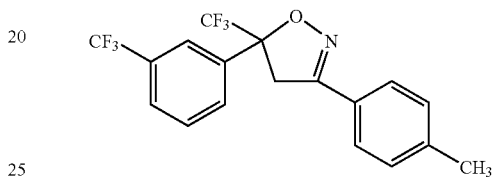

To a solution of 4,4,4-trifluoro-3-hydroxy-1-(4-methylphenyl)-3-[3-(trifluoromethyl)phenyl]butan-1-one oxime (0.45 g) and triphenylphosphine (0.60 g) in tetrahydrofuran (10 mL), diethyl azodicarboxylate (0.44 g) was added, and the mixture was stirred for 24 hours at room temperature. After the reaction solution was diluted with t-butylmethylether, the solution was washed with water and saturated brine and the organic layer was then dried over anhydrous magnesium sulfate. The solvent was distilled off under reduced pressure to yield 3-(4-methylphenyl)-5-(trifluoromethyl)-5-[3-(trifluoromethyl)phenyl]-4,5-dihydroisoxazole (0.11 g).

1H-NMR (CDCl3) δ: 2.38 (3H, s), 3.73 (1H, d), 4.13 (111, d), 7.22-7.25 (2H, m), 7.61-7.82 (6H, m)

SYNTHESIS EXAMPLE 11

Synthesis of methyl 4-(4,4,4-trifluoro-3-hydroxy-3-phenylbutanoyl)benzoate

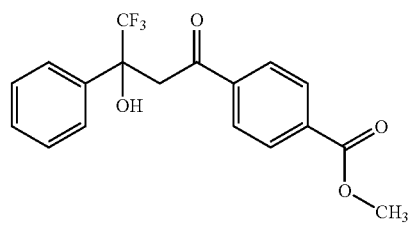 [SMILES: COC(=O)c1ccc(C(=O)CC(O)(c2ccccc2)C(F)(F)F)cc1]

A solution of 2,2,2-trifluoro-1-phenylethanone (2.0 g), methyl 4-acetylbenzoate (1.02 g) and lithium hydride (0.13 g) in hexane (30 mL) was stirred for 3 hours at 40° C. After the reaction solution was diluted with t-butylmethylether, the solution was washed with water and saturated brine. The organic layer was dried over anhydrous magnesium sulfate. The solvent was distilled off under reduced pressure, and the residue was then purified by silica gel chromatography to yield methyl 4-(4,4,4-trifluoro-3-hydroxy-3-phenylbutanoyl)benzoate (1.2 g).

1H-NMR (CDCl3) δ: 3.68 (1H, d), 3.96 (3H, s), 4.06 (1H, d), 5.43 (1H, s), 7.34-7.37 (4H, m), 7.58-7.61 (3H, m), 7.96-8.16 (2H, m)

SYNTHESIS EXAMPLE 12

Synthesis of N-[(4-{5-[3,4-dichloro-5-(trifluoromethyl)phenyl]-5-(trifluoromethyl)-4,5-dihydroisoxazol-3-yl}naphthalen-1-yl)methyl]acetamide (7-128)

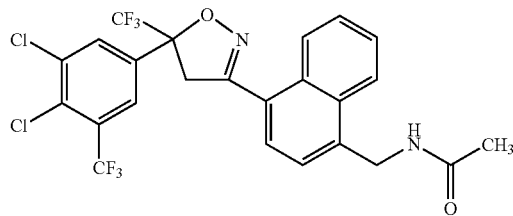 [SMILES: CC(=O)NCc1ccc(C2=NOC(c3cc(Cl)c(Cl)c(C(F)(F)F)c3)(C(F)(F)F)C2)c2ccccc12]

N-chlorosuccinimide (0.06 g) was added to N-({4-[(hydroxyimino)methyl]naphthalen-1-yl}methyl)acetamide (0.1 g) in N,N-dimethylformamide (10 ml), and the reaction mixture was stirred at room temperature for 2 hours. 1,2-dichloro-3-(trifluoromethyl)-5-[1-(trifluoromethyl)ethenyl]benzene (0.75 g) and potassium bicarbonate (0.13 g) was added to the reaction mixture, and the mixture was stirred at room temperature for 8 hours. Water was poured into the reaction mixture, and it was extracted with ethyl acetate. The organic layer was washed with brine, and dried over Magnesium sulfate anhydrous. The solvent was evaporated under the reduced pressure, and the residue was purified with silicagel columnchromatography to get N-[(4-{5-[3,4-dichloro-5-(trifluoromethyl)phenyl]-5-(trifluoromethyl)-4,5-dihydroisoxazol-3-yl}naphthalen-1-yl)methyl]acetamide (0.1 g).

1H-NMR (CDCl3) δ: 2.15 (3H, s), 3.89 (1H, d), 4.30 (1H, d), 4.88 (2H, d), 5.97-6.00 (1H, m), 7.42-7.44 (2H, m), 7.61-7.66 (2H, m), 7.87-7.91 (1H, m), 8.01-8.05 (2H, m), 8.84-8.88 (1H, m)

The compounds of formula (I) and intermediates thereof of the present invention obtained by processes analogous to the above Synthesis Examples and according to the processes described above in detail are shown in tables 1 to 9 together with their physical values. The compounds obtained in the above Synthesis Examples are also shown in the following tables.

TABLE 1

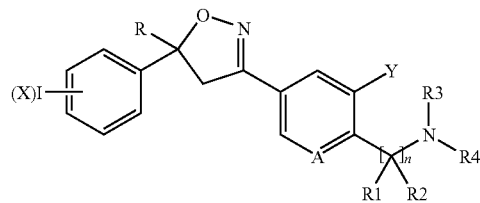

| No. | (X)l | R | Y | R¹ | R² | R⁴ | R³ | A | n |
|---|---|---|---|---|---|---|---|---|---|
| 1-1 | 3,5-diCl | CF3 | H | H | H | MeCO | H | CH | 1 |
| 1-2 | 3,5-diCl | CF3 | H | H | H | MeCO | MeCO | CH | 1 |
| 1-3 | 3,5-diCl | CF3 | H | H | H | MeCO | 2-pyridyl-CO | CH | 1 |
| 1-4 | 3,5-diCl | CF3 | H | H | H | HCO | 2-pyridyl-CH2 | CH | 1 |
| 1-5 | 3,5-diCl | CF3 | H | H | H | MeCO | 2-pyridyl-CH2 | CH | 1 |
| 1-6 | 3,5-diCl | CF3 | H | H | H | EtCO | 2-pyridyl-CH2 | CH | 1 |
| 1-7 | 3,5-diCl | CF3 | H | H | H | Me2NCO | 2-pyridyl-CH2 | CH | 1 |
| 1-8 | 3,5-diCl | CF3 | H | H | H | MeSO2 | 2-pyridyl-CH2 | CH | 1 |
| 1-9 | 3,5-diCl | CF3 | H | H | H | 2-pyridylCO | 2-pyridyl-CH2 | CH | 1 |
| 1-10 | 3,5-diCl | CF3 | H | CN | H | MeCO | H | CH | 1 |
| 1-11 | 3,5-diCl | CF3 | H | CN | H | MeCO | 2-pyridyl-CH2 | CH | 1 |
| 1-12 | 3,5-diCl | CF3 | Br | H | H | HCO | H | CH | 1 |
| 1-13 | 3,5-diCl | CF3 | Br | H | H | MeCO | H | CH | 1 |
| 1-14 | 3,5-diCl | CF3 | Br | H | H | MeCO | MeCO | CH | 1 |
| 1-15 | 3,5-diCl | CF3 | Br | H | H | MeCO | 2-pyridyl-CH2 | CH | 1 |
| 1-16 | 3,5-diCl | CF3 | Br | H | H | MeCO | 3-pyridylCH2 | CH | 1 |
| 1-17 | 3,5-diCl | CF3 | Br | H | H | MeCO | 4-pyridyl-CH2 | CH | 1 |
| 1-18 | 3,5-diCl | CF3 | Br | H | H | MeCO | benzyl | CH | 1 |
| 1-19 | 3,5-diCl | CF3 | Br | H | H | EtCO | H | CH | 1 |
| 1-20 | 3,5-diCl | CF3 | Br | H | H | n-PrCO | H | CH | 1 |
| 1-21 | 3,5-diCl | CF3 | Br | H | H | iso-PrCO | H | CH | 1 |
| 1-22 | 3,5-diCl | CF3 | Br | H | H | tert-BuCO | H | CH | 1 |
| 1-23 | 3,5-diCl | CF3 | Br | H | H | CF3CO | H | CH | 1 |
| 1-24 | 3,5-diCl | CF3 | Br | H | H | PhCO | H | CH | 1 |
| 1-25 | 3,5-diCl | CF3 | Br | H | H | 2-pyridyl-CO | H | CH | 1 |
| 1-26 | 3,5-diCl | CF3 | Br | H | H | 3-pyridyl-CO | H | CH | 1 |
| 1-27 | 3,5-diCl | CF3 | Br | H | H | 4-pyridyl-CO | H | CH | 1 |
| 1-28 | 3,5-diCl | CF3 | Br | H | H | 2-F-Ph-CO | H | CH | 1 |
| 1-29 | 3,5-diCl | CF3 | Br | H | H | 3-F-Ph-CO | H | CH | 1 |
| 1-30 | 3,5-diCl | CF3 | Br | H | H | 4-F-Ph-CO | H | CH | 1 |
| 1-31 | 3,5-diCl | CF3 | Br | H | H | 2-Cl-Ph-CO | H | CH | 1 |
| 1-32 | 3,5-diCl | CF3 | Br | H | H | 3-Cl-Ph-CO | H | CH | 1 |
| 1-33 | 3,5-diCl | CF3 | Br | H | H | 4-Cl-Ph-CO | H | CH | 1 |
| 1-34 | 3,5-diCl | CF3 | Br | H | H | 2-Br-Ph-CO | H | CH | 1 |
| 1-35 | 3,5-diCl | CF3 | Br | H | H | 2-Me-Ph-CO | H | CH | 1 |
| 1-36 | 3,5-diCl | CF3 | Br | H | H | vinyl-CO | H | CH | 1 |
| 1-37 | 3,5-diCl | CF3 | Br | H | H | HCCCO | H | CH | 1 |

TABLE 1-continued

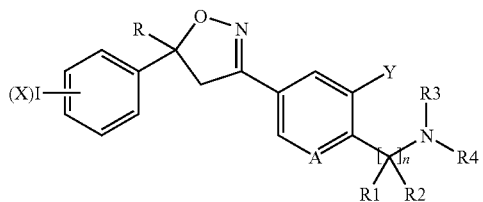

| No. | (X)l | R | Y | R¹ | R² | R⁴ | R³ | A | n |
|---|---|---|---|---|---|---|---|---|---|
| 1-38 | 3,5-diCl | CF3 | Br | H | H | MeSO2 | H | CH | 1 |
| 1-39 | 3,5-diCl | CF3 | Br | H | H | CF3SO2 | H | CH | 1 |
| 1-40 | 3,5-diCl | CF3 | Br | H | H | MeHNCO | H | CH | 1 |
| 1-41 | 3,5-diCl | CF3 | Br | H | H | Me2NCO | H | CH | 1 |
| 1-42 | 3,5-diCl | CF3 | Br | H | H | MeOC(=O) | H | CH | 1 |
| 1-43 | 3,5-diCl | CF3 | Br | H | H | MeSC(=O) | H | CH | 1 |
| 1-44 | 3,5-diCl | CF3 | Br | H | H | MeCS | H | CH | 1 |
| 1-45 | 3,5-diCl | CF3 | Br | H | H | MeON(Me)-CO | H | CH | 1 |
| 1-46 | 3,5-diCl | CF3 | Br | H | H | MeCO | Me | CH | 1 |
| 1-47 | 3,5-diCl | CF3 | Br | H | H | MeCO | Et | CH | 1 |
| 1-48 | 3,5-diCl | CF3 | Br | H | H | MeCO | vinyl | CH | 1 |
| 1-49 | 3,5-diCl | CF3 | Br | H | H | MeCO | propargyl | CH | 1 |
| 1-50 | 3,5-diCl | CF3 | Br | H | H | MeCO | CH2Ph | CH | 1 |
| 1-51 | 3,5-diCl | CF3 | Br | H | H | MeCO | CN | CH | 1 |
| 1-52 | 3,5-diCl | CF3 | Br | H | H | MeCO | CH2CF3 | CH | 1 |
| 1-53 | 3,5-diCl | CF3 | Br | H | H | MeCO | cycloPr | CH | 1 |
| 1-54 | 3,5-diCl | CF3 | Br | H | H | C(O)CH2CH2CH2 | | CH | 1 |
| 1-55 | 3,5-diCl | CF3 | Br | H | H | N-Me-tetrazoinone | | CH | 1 |
| 1-56 | 3,5-diCl | CF3 | Br | H | H | N-nitroimidazolidin-2-imine | | CH | 1 |
| 1-57 | 3,5-diCl | CF3 | F | H | H | MeCO | H | CH | 1 |
| 1-58 | 3,5-diCl | CF3 | Cl | H | H | MeCO | H | CH | 1 |
| 1-59 | 3,5-diCl | CF3 | I | H | H | MeCO | H | CH | 1 |
| 1-60 | 3,5-diCl | CF3 | NO2 | H | H | MeCO | H | CH | 1 |
| 1-61 | 3,5-diCl | CF3 | CN | H | H | MeCO | 2-pyridyl-CH2 | CH | 1 |
| 1-62 | 3,5-diCl | CF3 | CN | H | H | MeCO | H | CH | 1 |
| 1-63 | 3,5-diCl | CF3 | Me | H | H | MeCO | H | CH | 1 |
| 1-64 | 3,5-diCl | CF3 | Me | H | H | MeCO | 2-pyridyl-CH2 | CH | 1 |
| 1-65 | 3,5-diCl | CF3 | MeS | H | H | MeCO | H | CH | 1 |
| 1-66 | 3,5-diCl | CF3 | MeSO | H | H | MeCO | H | CH | 1 |
| 1-67 | 3,5-diCl | CF3 | MeSO2 | H | H | MeCO | H | CH | 1 |
| 1-68 | 3,5-diCl | CF3 | CF3S | H | H | MeCO | H | CH | 1 |
| 1-69 | 3,5-diCl | CF3 | CF3—S(O) | H | H | MeCO | H | CH | 1 |
| 1-70 | 3,5-diCl | CF3 | CF3S—(O)2 | H | H | MeCO | H | CH | 1 |
| 1-71 | 3,5-diCl | CF3 | OCH3 | H | H | MeCO | H | CH | 1 |
| 1-72 | 3,5-diCl | CF3 | OCF3 | H | H | MeCO | H | CH | 1 |
| 1-73 | 3,5-diCl | CF3 | OH | H | H | MeCO | H | CH | 1 |
| 1-74 | 3,5-diCl | CF3 | SH | H | H | MeCO | H | CH | 1 |
| 1-75 | 3,5-diCl | CF3 | NH2 | H | H | MeCO | H | CH | 1 |
| 1-76 | 3,5-diCl | CF3 | NHCO—CH3 | H | H | MeCO | H | CH | 1 |
| 1-77 | 3,5-diCl | CF3 | NHCO2—CH3 | H | H | MeCO | H | CH | 1 |
| 1-78 | 3,5-diCl | CF3 | NHCO2—CH2—CCl3 | H | H | MeCO | H | CH | 1 |
| 1-79 | 3,5-diCl | CF3 | Br | Me | H | MeCO | H | CH | 1 |
| 1-80 | 3,5-diCl | CF3 | Br | Me | Me | MeCO | H | CH | 1 |
| 1-81 | 3,5-diCl | CF3 | H | cyclo-Pr | H | MeCO | H | CH | 1 |
| 1-82 | 3,5-diCl | CF3 | H | CF3 | H | MeCO | H | CH | 1 |
| 1-83 | 3,5-diCl | CF3 | H | CO2Me | H | MeCO | H | CH | 1 |
| 1-84 | 3,5-diCl | CF3 | H | CH=CH2 | H | MeCO | H | CH | 1 |
| 1-85 | 3,5-diCl | CF3 | H | CCH | H | MeCO | H | CH | 1 |
| 1-86 | 3,5-diCl | CF3 | H | CH2CH2 | | MeCO | H | CH | 1 |
| 1-87 | 3,5-diCl | CF3 | H | H | H | MeCO | H | CH | 1 |
| 1-88 | 3,5-diCl | CF3 | H | H | H | MeCO | NH2 | CH | 1 |
| 1-89 | 3,5-diCl | CF3 | H | H | H | MeCO | NHCOMe | CH | 1 |
| 1-90 | 3,5-diCl | CF3 | Br | H | H | MeCO | N=CMe2 | CH | 1 |
| 1-91 | 3,5-diCl | CF3 | H | H | H | MeCO | OH | CH | 1 |
| 1-92 | 3,5-diCl | CF3 | H | H | H | MeCO | MeO | CH | 1 |
| 1-93 | 3,5-diCl | CH3 | Br | H | H | MeCO | H | CH | 1 |
| 1-94 | 3,4-diCl | CF3 | Br | H | H | MeCO | H | CH | 1 |

TABLE 1-continued

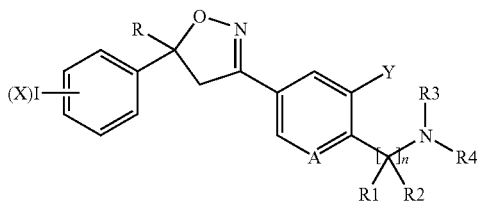

| No. | (X)l | R | Y | R¹ | R² | R⁴ | R³ | A | n |
|---|---|---|---|---|---|---|---|---|---|
| 1-95 | 3,4,5-triCl | CH3 | Br | H | H | MeCO | H | CH | 1 |
| 1-96 | 3,5-diCl-4-Me | CH3 | Br | H | H | MeCO | H | CH | 1 |
| 1-97 | 3-F | CH3 | Br | H | H | MeCO | H | CH | 1 |
| 1-98 | 3-Cl | CF3 | Br | H | H | MeCO | H | CH | 1 |
| 1-99 | 3-CF3 | CF3 | Br | H | H | MeCO | H | CH | 1 |
| 1-100 | 4-CF3 | CF3 | Br | H | H | MeCO | H | CH | 1 |
| 1-101 | 3,5-diCF3 | CF3 | Br | H | H | MeCO | H | CH | 1 |
| 1-102 | 3-NO2 | CF3 | Br | H | H | MeCO | H | CH | 1 |
| 1-103 | 3,5-diCl | CF3 | H | H | H | MeCO | H | N | 1 |
| 1-104 | 3-CH3 | CF3 | Br | H | H | MeCO | H | CH | 1 |
| 1-105 | 3-CH3O | CF3 | Br | H | H | MeCO | H | CH | 1 |
| 1-106 | 3-CN | CF3 | Br | H | H | MeCO | H | CH | 1 |
| 1-107 | 3-CF3O | CF3 | Br | H | H | MeCO | H | CH | 1 |
| 1-108 | 3-CH3S | CF3 | Br | H | H | MeCO | H | CH | 1 |
| 1-109 | 3-CH3—S(O) | CF3 | Br | H | H | MeCO | H | CH | 1 |
| 1-110 | 3-CH3—S(O)2 | CF3 | Br | H | H | MeCO | H | CH | 1 |
| 1-111 | 3-CF3S | CF3 | Br | H | H | MeCO | H | CH | 1 |
| 1-112 | 3-CF3—S(O) | CF3 | Br | H | H | MeCO | H | CH | 1 |
| 1-113 | 3-CF3—S(O)2 | CF3 | Br | H | H | MeCO | H | CH | 1 |
| 1-114 | 3-OH | CF3 | Br | H | H | MeCO | H | CH | 1 |
| 1-115 | 3-SH | CF3 | Br | H | H | MeCO | H | CH | 1 |
| 1-116 | 3-NH2 | CF3 | Br | H | H | MeCO | H | CH | I |
| 1-117 | 3-NH—CO—CH3 | CF3 | Br | H | H | MeCO | H | CH | 1 |
| 1-118 | 3-NH—CO—CF3 | CF3 | Br | H | H | MeCO | H | CH | 1 |
| 1-119 | 3-NH—CO2CH3 | CF3 | Br | H | H | MeCO | H | CH | 1 |
| 1-120 | 3-NH—CO2—CH2—CCl3 | CF3 | Br | H | H | MeCO | H | CH | I |
| 1-121 | 3-NH—SO2CH3 | CF3 | Br | H | H | MeCO | H | CH | I |
| 1-122 | 3-NH—SO2CF3 | CF3 | Br | H | H | MeCO | H | CH | 1 |
| 1-123 | 3,5-diCl | CF3 | NHCOCF3 | H | H | MeCO | H | CH | 1 |
| 1-124 | 3,5-diCl | CF3 | NH—SO2CH3 | H | H | MeCO | H | CH | 1 |
| 1-125 | 3,5-diCl | CF3 | NH—SO2CF3 | H | H | MeCO | H | CH | 1 |
| 1-126 | 3,5-diCl | CF3 | H | H | H | MeCO | H | CH | 2 |
| 1-127 | 3,5-diBr | CF3 | H | H | H | MeCO | H | CH | I |
| 1-128 | 3-F | CF3 | Br | H | H | MeCO | H | CH | 1 |
| 1-129 | 3,4,5-triCl | CF3 | Br | H | H | MeCO | H | CH | 1 |
| 1-130 | 3,5-diCl-4-Me | CF3 | Br | H | H | MeCO | H | CH | 1 |
| 1-131 | 3,4,5-triF | CF3 | Br | H | H | MeCO | H | CH | 1 |
| 1-132 | 3,4,5-triBr | CF3 | Br | H | H | MeCO | H | CH | 1 |
| 1-133 | 3,5-diCl, 4-Br | CF3 | Br | H | H | MeCO | H | CH | 1 |
| 1-134 | 3,5-diCl, 4-Br | CF3 | Br | H | H | EtCO | H | CH | 1 |
| 1-135 | 3,5-diBr, 4-Cl | CF3 | Br | H | H | MeCO | H | CH | 1 |
| 1-136 | 3,5-diBr, 4-Cl | CF3 | Br | H | H | EtCO | H | CH | 1 |

TABLE 1-continued

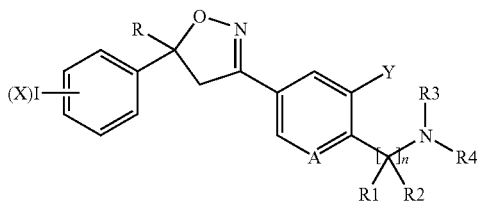

| No. | (X)l | R | Y | R¹ | R² | R⁴ | R³ | A | n |
|---|---|---|---|---|---|---|---|---|---|
| 1-137 | 3,5-diCl, 4-NH2 | CF3 | Br | H | H | MeCO | H | CH | 1 |
| 1-138 | 3,5-diBr, 4-NH2 | CF3 | Br | H | H | MeCO | H | CH | 1 |
| 1-139 | 3,5-diBr 4-NH2 | CF3 | Br | H | H | EtCO | H | CH | 1 |
| 1-140 | 3,4-diCl, 5-CF3 | CF3 | Br | H | H | MeCO | H | CH | 1 |
| 1-141 | 3,5-diCl, 4-CF3 | CF3 | Br | H | H | MeCO | H | CH | 1 |
| 1-142 | 3,5-diCl, 4-CF3 | CF3 | Br | H | H | EtCO | H | CH | 1 |
| 1-143 | 3-Cl, 5-CF3 | CF3 | Br | H | H | MeCO | H | CH | 1 |
| 1-144 | 3-Cl, 4-CF3 | CF3 | Br | H | H | MeCO | H | CH | 1 |
| 1-145 | 3-Br, 5-CF3 | CF3 | Br | H | H | MeCO | H | CH | 1 |
| 1-146 | 3-Br, 4-CF3 | CF3 | Br | H | H | MeCO | H | CH | 1 |
| 1-147 | 3-CF3, 4-F | CF3 | Br | H | H | MeCO | H | CH | 1 |
| 1-148 | 3-Cl, 5-SCF3 | CF3 | Br | H | H | MeCO | H | CH | 1 |

TABLE 2

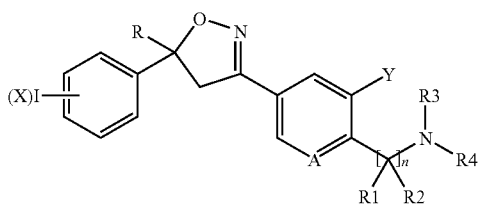

| No. | (X)l | R | Y | R¹ | R² | R⁴ | R³ | A | n |
|---|---|---|---|---|---|---|---|---|---|
| 2-1 | 3,5-diCl | CF3 | H | H | H | H | H | CH | 1 |
| 2-2 | 3,5-diCl | CF3 | CH3 | H | H | H | H | CH | 1 |
| 2-3 | 3,5-diCl | CF3 | F | H | H | H | H | CH | 1 |
| 2-4 | 3,5-diCl | CF3 | Cl | H | H | H | H | CH | 1 |
| 2-5 | 3,5-diCl | CF3 | Br | H | H | H | H | CH | 1 |
| 2-6 | 3,5-diCl | CF3 | I | H | H | H | H | CH | 1 |
| 2-7 | 3,5-diCl | CF3 | NO2 | H | H | H | H | CH | 1 |
| 2-8 | 3,5-diCl | CF3 | CN | H | H | H | H | CH | 1 |
| 2-9 | 3,5-diCl | CF3 | MeS | H | H | H | H | CH | 1 |
| 2-10 | 3,5-diCl | CF3 | MeSO | H | H | H | H | CH | 1 |
| 2-11 | 3,5-diCl | CF3 | MeSO2 | H | H | H | H | CH | 1 |
| 2-12 | 3,5-diCl | CF3 | CF3S | H | H | H | H | CH | 1 |
| 2-13 | 3,5-diCl | CF3 | CF3—S(O) | H | H | H | H | CH | 1 |
| 2-14 | 3,5-diCl | CF3 | CF3—S(O)2 | H | H | H | H | CH | 1 |
| 2-15 | 3,5-diCl | CF3 | OCH3 | H | H | H | H | CH | 1 |
| 2-16 | 3,5-diCl | CF3 | OCF3 | H | H | H | H | CH | 1 |
| 2-17 | 3,5-diCl | CF3 | OH | H | H | H | H | CH | 1 |
| 2-18 | 3,5-diCl | CF3 | SH | H | H | H | H | CH | 1 |
| 2-19 | 3,5-diCl | CF3 | NH2 | H | H | H | H | CH | 1 |
| 2-20 | 3,5-diCl | CF3 | NHCOCH3 | H | H | H | H | CH | 1 |
| 2-21 | 3,5-diCl | CF3 | NHCO2CH3 | H | H | H | H | CH | 1 |
| 2-22 | 3,5-diCl | CF3 | NHCO2CH2CCl3 | H | H | H | H | CH | 1 |
| 2-23 | 3,4-diCl | CF3 | Br | H | H | H | H | CH | 1 |
| 2-24 | 3,4,5-triCl | CF3 | Br | H | H | H | H | CH | 1 |
| 2-25 | 3,5-diCl-4-Me | CF3 | Br | H | H | H | H | CH | 1 |

TABLE 2-continued

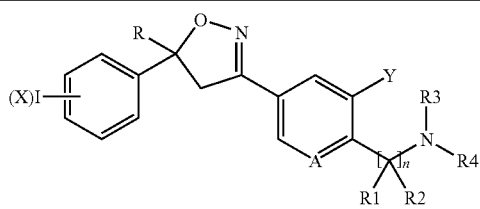

| No. | (X)l | R | Y | R¹ | R² | R⁴ | R³ | A | n |
|---|---|---|---|---|---|---|---|---|---|
| 2-26 | 3-F | CF3 | Br | H | H | H | H | CH | 1 |
| 2-27 | 3-Cl | CF3 | Br | H | H | H | H | CH | 1 |
| 2-28 | 3-CF3 | CF3 | Br | H | H | H | H | CH | 1 |
| 2-29 | 4-CF3 | CF3 | Br | H | H | H | H | CH | 1 |
| 2-30 | 3,5-diCF3 | CF3 | Br | H | H | H | H | CH | 1 |
| 2-31 | 3-NO2 | CF3 | Br | H | H | H | H | CH | 1 |
| 2-32 | 3,5-diCl | CF3 | Br | H | H | H | H | CH | 1 |
| 2-33 | 3-CH3 | CF3 | Br | H | H | H | H | CH | 1 |
| 2-34 | 3-CH3O | CF3 | Br | H | H | H | H | CH | 1 |
| 2-35 | 3-CN | CF3 | Br | H | H | H | H | CH | 1 |
| 2-36 | 3-CF3O | CF3 | Br | H | H | H | H | CH | 1 |
| 2-37 | 3-CH3S | CF3 | Br | H | H | H | H | CH | 1 |
| 2-38 | 3-CH3S(O) | CF3 | Br | H | H | H | H | CH | 1 |
| 2-39 | 3-CH3S(O)2 | CF3 | Br | H | H | H | H | CH | 1 |
| 2-40 | 3-CF3S | CF3 | Br | H | H | H | H | CH | 1 |
| 2-41 | 3-CF3S(O) | CF3 | Br | H | H | H | H | CH | 1 |
| 2-42 | 3-CF3S(O)2 | CF3 | Br | H | H | H | H | CH | 1 |
| 2-43 | 3-OH | CF3 | Br | H | H | H | H | CH | 1 |
| 2-44 | 3-SH | CF3 | Br | H | H | H | H | CH | 1 |
| 2-45 | 3,5-diCl | CF3 | H | H | H | H | 2-pyridyl-CH2 | CH | 1 |
| 2-46 | 3,5-diCl | CF3 | CH3 | H | H | H | 2-pyridyl-CH2 | CH | 1 |
| 2-47 | 3,5-diCl | CF3 | Br | H | H | H | 2-pyridyl-CH2 | CH | 1 |
| 2-48 | 3,5-diCl | CF3 | Br | H | H | H | 3-pyridyl-CH2 | CH | 1 |
| 2-49 | 3,5-diCl | CF3 | Br | H | H | H | 4-pyridyl-CH2 | CH | 1 |
| 2-50 | 3,5-diCl | CF3 | Br | H | H | H | CH3 | CH | 1 |
| 2-51 | 3,5-diCl | CF3 | H | CN | H | H | 2-pyridyl-CH2 | CH | 1 |
| 2-52 | 3,5-diCl | CF3 | Br | H | H | H | N=CMe2 | CH | 1 |
| 2-53 | 3,5-diCl | CF3 | H | H | H | phthalimide | | CH | 1 |
| 2-54 | 3,5-diCl | CF3 | Br | H | H | phthalimide | | CH | 1 |
| 2-55 | 3,5-diCl | CF3 | CN | H | H | phthalimide | | CH | 1 |
| 2-56 | 3,5-diCl | CF3 | Br | CH3 | H | H | H | CH | 1 |
| 2-57 | 3,5-diCl | CF3 | Br | CH3 | CH3 | H | H | CH | 1 |
| 2-58 | 3,5-diCl | CF3 | Br | cyclo-Pr | H | H | H | CH | 1 |
| 2-59 | 3,5-diCl | CF3 | Br | CF3 | H | H | H | CH | 1 |
| 2-60 | 3,5-diCl | CF3 | Br | CO2Me | H | H | H | CH | 1 |
| 2-61 | 3,5-diCl | CF3 | Br | CH=CH2 | H | H | H | CH | 1 |
| 2-62 | 3,5-diCl | CF3 | Br | CCH | H | H | H | CH | 1 |
| 2-63 | 3,5-diCl | CF3 | Br | CH2CH2 | H | H | H | CH | 1 |
| 2-64 | 3,5-diCl | CF3 | Br | H | H | H | Et | CH | 1 |
| 2-65 | 3,5-diCl | CF3 | Br | H | H | H | vinyl | CH | 1 |
| 2-66 | 3,5-diCl | CF3 | Br | H | H | H | propargyl | CH | 1 |
| 2-67 | 3,5-diCl | CF3 | Br | H | H | H | CH2Ph | CH | 1 |
| 2-68 | 3,5-diCl | CF3 | Br | H | H | H | CN | CH | 1 |
| 2-69 | 3,5-diCl | CF3 | Br | H | H | H | CH2CF3 | CH | 1 |
| 2-70 | 3,5-diCl | CF3 | Br | H | H | H | cycloPr | CH | 1 |
| 2-71 | 3,5-diCl | CF3 | H | H | H | H | H | N | 1 |
| 2-72 | 3,5-diCl | CF3 | Br | H | H | H | H | CH | 2 |
| 2-73 | 3-NH2 | CF3 | Br | H | H | H | H | CH | 1 |
| 2-74 | 3-NHCOCH3 | CF3 | Br | H | H | H | H | CH | 1 |
| 2-75 | 3-NHCOCF3 | CF3 | Br | H | H | H | H | CH | 1 |
| 2-76 | 3-NHCO2CH3 | CF3 | Br | H | H | H | H | CH | 1 |
| 2-77 | 3-NHCO2CH2CCl3 | CF3 | Br | H | H | H | H | CH | 1 |
| 2-78 | 3-NHSO2CH3 | CF3 | Br | H | H | H | H | CH | 1 |
| 2-79 | 3-NHSO2CF3 | CF3 | Br | H | H | H | H | CH | 1 |
| 2-80 | 3,5-diCl | CF3 | NHCOCF3 | H | H | H | H | CH | 1 |
| 2-81 | 3,5-diCl | CF3 | NHSO2CH3 | H | H | H | H | CH | 1 |

TABLE 2-continued

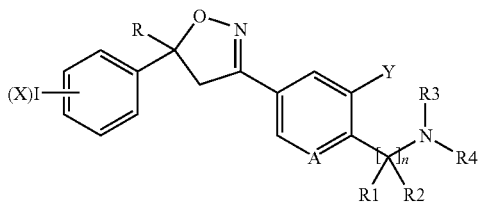

| No. | (X)l | R | Y | R¹ | R² | R⁴ | R³ | A | n |
|---|---|---|---|---|---|---|---|---|---|
| 2-82 | 3,5-diCl | CF3 | NHSO2CF3 | H | H | H | H | CH | 1 |
| 2-83 | 3,5-diBr | CF3 | Br | H | H | H | H | CH | 1 |

TABLE 3

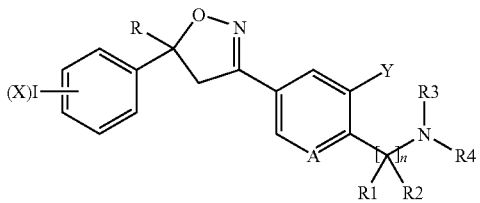

| No. | 1H-NMR |
|---|---|
| 1-1 | 1H-NMR (CDCl3) δ: 2.04 (3H, s), 3.88 (2H, dd), 4.45 (2H, d), 6.06 (1H, s), 7.32 (2H, d), 7.42-7.42 (1H, m), 7.49-7.52 (2H, m), 7.59-7.62 (2H, m) |
| 1-2 | 1H-NMR (CDCl3) δ: 1.86 (3H, s), 2.13 (3H, s), 3.68 (1H, d), 4.08 (1H, d), 4.66-4.67 (2H, m), 7.35 (2H, d), 7.41-7.51 (1H, m), 7.51-7.51 (2H, m), 7.59 (2H, d) |
| 1-4 | 1H-NMR (CDCl3) δ: 3.68-4.07 (2H, m), 4.44-4.50 (4H, m), 7.17-7.25 (4H, m), 7.42-7.43 (1H, m), 7.50-7.53 (2H, m), 7.62-7.65 (3H, m), 8.43-8.45 (1H, m), 8.53-8.59 (1H, m) |
| 1-5 | 1H-NMR (CDCl3) δ: 2.0-2.2 (3H, m), 3.8-4.3 (2H, m), 4.5-4.8 (4H, m), 7.1-7.4 (4H, m), 7.5-7.8 (5H, m), 8.4-8.7 (1H, m) |
| 1-6 | 1H-NMR (CDCl3) δ: 1.14-1.28 (3H, m), 2.42-2.48 (2H, m), 3.74-4.05 (2H, m), 4.61-4.66 (4H, m), 7.10-7.71 (10H, m), 8.50-8.58 (1H, m) |
| 1-7 | 1H-NMR (CDCl3) & 2.89 (6H, s), 3.88 (2H, dd), 4.42-4.45 (4H, m), 7.18-7.20 (1H, m), 7.25-7.27 (1H, m), 7.31-7.33 (2H, m), 7.41-7.42 (1H, m), 7.51-7.52 (2H, m), 7.62-7.67 (3H, m), 8.54-8.56 (1H, m) |
| 1-8 | 1H-NMR (CDCl3) δ: 2.98 (3H, s), 3.88 (2H, dd), 4.45-4.47 (4H, m), 7.18-7.24 (2H, m), 7.39-7.42 (3H, m), 7.52-7.52 (2H, m), 7.62-7.66 (3H, m), 8.57-8.58 (1H, m) |
| 1-9 | 1H-NMR (CDCl3) δ: 2.17 (3H, s), 3.88 (2H, dd), 4.79-4.88 (4H, m), 7.18-7.20 (1H, m), 7.32-7.52 (7H, m), 7.58-7.78 (5H, m), 8.52-8.55 (2H, m) |
| 1-11 | 1H-NMR (CDCl3) δ: 2.28 (3H, s), 3.86 (2H, dd), 4.54-4.64 (2H, m), 6.99-7.01 (1H, m), 7.13-7.16 (2H, m), 7.43-7.61 (8H, m), 8.48-8.50 (1H, m) |
| 1-12 | 1H-NMR (CDCl3) δ: 3.63-4.08 (2H, m), 4.55 (2H, d), 6.04 (1H, s), 7.37-7.60 (5H, m), 7.89 (1H, d), 8.29 (1H, s). |
| 1-13 | 1H-NMR (CDCl3) δ: 2.04 (3H, br s), 3.83 (2H, dd), 4.46-4.48 (2H, m), 6.09 (1H, br s), 7.40-7.54 (5H, m), 7.82 (1H, s) |
| 1-15 | 1H-NMR (CDCl3) δ: 2.10-2.22 (3H, m), 3.63-4.13 (2H, m), 4.63-4.74 (4H, m), 7.14-7.90 (9H, m), 8.51-8.59 (1H, m) |
| 1-16 | 1H-NMR (CDCl3) δ: 2.15-2.17 (3H, m), 3.65-4.13 (2H, m), 4.55-4.69 (4H, m), 7.16-7.91 (8H, m), 8.45-8.56 (2H, m) |
| 1-17 | 1H-NMR (CDCl3) δ: 2.08-2.19 (3H, m), 3.82-4.03 (2H, m), 4.56-4.71 (4H, m), 7.10-7.91 (8H, m), 8.56-8.62 (2H, m) |
| 1-19 | 1H-NMR (CDCl3) δ: 1.17 (3H, t), 2.23 (2H, q), 3.63- 4.07 (2H, m), 4.52 (2H, d), 5.94 (1H, s), 7.42-7.58 (5H, m), 7.86 (1H, d). |
| 1-20 | 1H-NMR (CDCl3) δ: 0.93 (3H, t), 1.68 (2H, m), 2.21 (2H, t), 3.63-4.08 (2H, m), 4.53 (2H, d), 5.92 (1H, s), 7.42-7.58 (5H, m), 7.87 (1H, d). |
| 1-21 | 1H-NMR (CDCl3) & 1.17 (6H, d), 2.39 (1H, m), 3.63-4.07 (2H, m), 4.52 (2H, d), 5.96 (1H, s), 7.50 (5H, m), 7.87 (1H, d). |
| 1-22 | 1H-NMR (CDCl3) δ: 1.20 (9H, s), 3.63-4.07 (2H, m), 4.50 (2H, d), 6.18 (1H, s), 7.41-7.57 (5H, m), 7.87 (1H, d). |
| 1-23 | 1H-NMR (CDCl3) δ: 3.64-4.08 (2H, m), 4.47 (2H, d), 6.79 (1H, s), 7.42-7.63 (5H, m), 7.86 (1H, d). |
| 1-24 | 1H-NMR (CDCl3) δ: 3.63-4.07 (2H, m), 4.73 (2H, d), 6.67 (1H, s), 7.42-7.60 (8H, m), 7.78 (2H, m), 7.89 (1H, d). |
| 1-25 | 1H-NMR (CDCl3) δ: 3.62-4.09 (2H, m), 4.79 (1H, d), 7.51 (7H, m), 7.86 (2H, t), 8.21 (1H, d), 8.57 (2H, d). |
| 1-26 | 1H-NMR (CDCl3) δ: 3.63-4.09 (2H, m), 4.75 (2H, d), 6.71 (1H, s), 7.38-7.61 (6H, m), 7.90 (1H, d), 8.12 (1H, m), 8.75 (1H, m), 8.99 (1H, d). |
| 1-27 | 1H-NMR (CDCl3) δ: 3.62-4.06 (2H, m), 4.73 (2H, d), 6.76 (1H, s), 7.41-7.62 (7H, m), 7.90 (1H, d), 8.75 (2H, m). |
| 1-28 | 1H-NMR (CDCl3) δ: 3.63-4.07 (2H, m), 4.75 (2H, d), 7.10-7.65 (9H, m), 7.88 (1H, d), 8.11 (1H, d). |
| 1-31 | 1H-NMR (CDCl3) δ: 3.64-4.09 (2H, m), 4.75 (2H, d), 6.80 (1H, s), 7.26-7.50 (6H, m), 7.60-7.73 (3H, m), 7.90 (1H, s). |
| 1-32 | 1H-NMR (CDCl3) δ: 3.63-4.07 (2H, m), 4.72 (2H, d), 6.62 (1H, s), 7.36-7.66 (8H, m), 7.77 (1H, t), 7.90 (1H, d). |
| 1-33 | 1H-NMR (CDCl3) δ: 3.63-4.07 (2H, m), 4.72 (2H, d), 6.62 (1H, s), 7.40-7.60 (7H, m), 7.72 (2H, m), 7.90 (1H, d). |
| 1-34 | 1H-NMR (CDCl3) δ: 3.64-4.09 (2H, m), 4.75 (2H, d), 6.55 (1H, s), 7.26-7.65 (9H, m), 7.90 (1H, d). |
| 1-35 | 1H-NMR (CDCl3) δ: 2.43 (3H, s), 3.63-4.09 (2H, m), 4.71 (2H, d), 6.28 (1H, s), 7.18-7.62 (9H, m), 7.90 (1H, s). |
| 1-36 | 1H-NMR (CDCl3) δ: 3.62-4.07 (2H, m), 4.61 (2H, d), 5.68-6.36 (4H, m), 7.42-7.58 (5H, m), 7.87 (1H, d). |
| 1-37 | 1H-NMR (CDCl3) δ: 2.84 (1H, s), 3.66-4.07 (2H, m), 4.58 (2H, d), 6.34 (1H, s), 7.52 (5H, m), 7.89 (1H, d). |
| 1-38 | 1H-NMR (CDCl3) δ: 2.90 (3H, s), 3.64-4.09 (2H, m), 4.44 (2H, d), 4.85 (1H, t), 7.43-7.64 (5H, m), 7.91 (1H, d). |

TABLE 3-continued

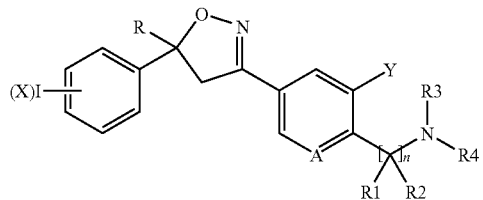

| No. | 1H-NMR |
|---|---|
| 1-40 | 1H-NMR (CDCl3) δ: 2.79 (3H, d), 3.62-4.07 (2H, m), 4.30 (1H, m), 4.46 (2H, d), 4.85 (1H, t), 7.42-7.57 (5H, m), 7.85 (1H, d). |
| 1-41 | 1H-NMR (CDCl3) δ: 2.92 (6H, s), 3.62-4.06 (2H, m), 4.49 (2H, d), 5.00 (1H, t), 7.42-7.61 (5H, m), 7.85 (1H, d). |
| 1-42 | 1H-NMR (CDCl3) δ: 3.63-4.07 (5H, m), 4.44 (2H, d), 5.23 (1H, s), 7.42-7.60 (5H, m), 7.86 (1H, d). |
| 1-43 | 1H-NMR (CDCl3) δ: 2.37 (3H, s), 3.66-4.07 (2H, m), 4.56 (2H, d), 5.84 (1H, s), 7.42-7.60 (5H, m), 7.86 (1H, d). |
| 1-44 | 1H-NMR (CDCl3) δ: 2.60 (3H, s), 3.66-4.09 (2H, m), 4.97 (2H, d), 7.43-7.60 (6H, m), 7.87 (1H, d). |
| 1-46 | 1H-NMR (CDCl3) δ: 2.16-2.26 (3H, m), 3.02 (3H, s), 3.63-4.09 (2H, m), 4.57-4.72 (2H, m), 7.16-7.25 (1H, m), 7.47-7.60 (4H, m), 7.84-7.93 (1H, m). |
| 1-55 | 1H-NMR (CDCl3) δ: 3.65-4.08 (5H, m), 5.24 (2H, s), 7.28-7.30 (1H, m), 7.42-7.43 (1H, m), 7.49-7.50 (2H, m), 7.60-7.62 (1H, m), 7.89-7.89 (1H, m). |
| 1-56 | 1H-NMR (CDCl3) δ: 3.55-4.08 (6H, m), 4.71 (2H, s), 7.53 (5H, m), 7.89 (1H, d), 8.19 (1H, s). |
| 1-57 | 1H-NMR (CDCl3) δ: 2.03 (3H, s), 3.66 (1H, d), 4.07 (1H, d), 4.50 (2H, d), 5.82-5.85 (1H, m), 7.35-7.46 (6H, m). |
| 1-58 | 1H-NMR (CDCl3) δ: 2.03 (3H, s), 3.66 (1H, d), 4.07 (1H, d), 4.53 (2H, d), 5.91-5.94 (1H, m), 7.49-7.63 (6H, m). |
| 1-59 | 1H-NMR (CDCl3) δ: 2.04 (3H, s), 3.65 (1H, d), 4.04 (1H, d), 4.47 (2H, d), 5.92-5.95 (1H, m), 7.48-7.57 (5H, m), 8.11-8.11 (1H, m). |
| 1-60 | 1H-NMR (CDCl3) δ: 2.04 (3H, s), 3.72 (1H, d), 4.11 (1H, d), 4.69 (2H, d), 6.27-6.29 (1H, m), 7.45-7.49 (3H, m), 7.80-7.91 (2H, m), 8.29 (1H, d). |
| 1-61 | 1H-NMR (CDCl3) δ: 2.27-2.31 (3H, m), 3.75-4.06 (2H, m), 4.68-4.87 (4H, m), 7.17-7.96 (9H, m), 8.49-8.57 (1H, m). |
| 1-62 | 1H-NMR (CDCl3) δ: 2.04 (3H, s), 3.66 (1H, d), 4.07 (1H, d), 4.48 (2H, d), 6.53 (1H, br s), 7.27-7.83 (6H, m). |
| 1-63 | 1H-NMR (CDCl3) δ: 2.04 (3H, s), 3.68 (1H, d), 4.07 (1H, d), 4.45 (2H, d), 5.61-5.64 (1H, m), 7.19-7.27 (3H, m), 7.43-7.50 (3H, m). |
| 1-64 | 1H-NMR (CDCl3) δ: 2.24 (3H, s), 3.91 (2H, d), 4.17 (1H, d), 4.5-4.6 (4H, m), 7.1-7.7 (9H, m), 8.4-8.6 (1H, m) |
| 1-79 | 1H-NMR (CDCl3) δ: 1.47 (3H, d), 2.03 (3H, s), 3.62-4.06 (2H, m), 5.30 (1H, m), 5.80 (1H, m), 7.50 (1H, m). |
| 1-90 | 1H-NMR (CDCl3) δ: 1.90-2.08 (9H, m), 3.65-3.70 (1H, m), 4.02-4.05 (1H, m), 4.79-4.88 (2H, m), 7.42-7.60 (5H, m), 7.81-7.88 (1H, m) |
| 1-93 | 1H-NMR (CDCl3) δ: 1.74 (3H, s), 1.78 (3H, s), 3.43 (2H, d), 4.50-4.53 (2H, m), 6.04-6.06 (1H, m), 7.35-7.36 (3H, m), 7.47-7.49 (1H, m), 7.69-7.72 (1H, m), 8.04-8.04 (1H, m) |
| 1-94 | 1H-NMR (CDCl3) δ: 2.04 (3H, s), 3.62-4.07 (2H, m), 4.53 (2H, d), 5.97 (1H, s), 7.50 (4H, m), 7.71 (1H, d), 7.86 (1H, d). |
| 1-97 | 1H-NMR (CDCl3) δ: 2.04 (3H, s), 3.62-4.07 (2H, m), 4.52 (2H, d), 5.94 (1H, s), 6.88 (1H, m), 7.15 (2H, d), 7.52 (2H, m), 7.87 (1H, d). |
| 1-98 | 1H-NMR (CDCl3) δ: 2.03 (3H, s), 3.65-4.07 (2H, m), 4.52 (2H, d), 5.34 (1H, s), 7.38-7.61 (6H, m), 7.87 (1H, d). |
| 1-99 | 1H-NMR (CDCl3) δ: 2.05 (3H, s), 3.68-4.13 (2H, m), 4.54 (2H, d), 5.92 (1H, s), 7.45-7.88 (7H, m). |
| 1-100 | 1H-NMR (CDCl3) δ: 2.03 (3H, s), 3.67-4.12 (2H, m), 4.52 (2H, d), 5.95 (1H, s), 7.45-7.88 (7H, m). |
| 1-101 | 1H-NMR (CDCl3) δ: 2.07 (3H, s), 3.68-4.19 (2H, m), 4.52 (2H, d), 5.96 (1H, s), 7.53 (2H, m), 7.88 (1H, d), 7.97 (1H, s), 8.07 (2H, s). |
| 1-102 | 1H-NMR (CDCl3) δ: 2.06 (3H, s), 3.71-4.17 (2H, m), 4.52 (2H, d), 5.96 (1H, s), 7.58 (3H, m), 7.94 (2H, m), 8.31 (1H, m), 8.47 (1H, s). |
| 1-106 | 1H-NMR (CDCl3) δ: 2.04 (3H, s), 3.65-4.12 (2H, m), 4.52 (2H, d), 5.95 (1H, s), 7.46-7.91 (7H, m). |
| 1-126 | 1H-NMR (CDCl3) δ: 1.95 (3H, s), 2.86 (2H, t), 3.52 (2H, q), 3.65-4.11 (2H, m), 5.43 (1H, s), 7.51 (7H, m) |
| 1-128 | 1H-NMR (CDCl3) δ: 2.04 (3H, s), 3.62-4.07 (2H, m), 4.52 (2H, d), 5.94 (1H, s), 6.88 (1H, m), 7.15 (2H, d), 7.52 (2H, m), 7.87 (1H, d). |
| 1-129 | 1H-NMR (CDCl3) δ: 2.04 (3H, s), 3.66 (1H, d), 4.05 (1H, d), 4.51 (2H, d), 6.03-6.07 (1H, m), 7.43-7.46 (1H, m), 7.54-7.57 (1H, m), 7.62-7.65 (2H, m), 7.85-7.85 (1H, m) |
| 1-131 | 1H-NMR (CDCl3) δ: 2.04 (3H, s), 3.63 (1H, d), 4.04 (1H, d), 4.52 (2H, d), 5.94-5.98 (1H, m), 7.26-7.28 (2H, m), 7.45-7.48 (1H, m), 7.54-7.57 (1H, m), 7.86-7.86 (1H, m) |
| 1-133 | 1H-NMR (CDCl3) δ: 2.04 (3H, s), 3.65 (1H, d), 4.04 (1H, d), 4.52 (2H, d), 5.94-5.98 (1H, m), 7.45-7.48 (1H, m), 7.55-7.58 (1H, m), 7.60-7.63 (2H, m), 7.86-7.87 (1H, m) |
| 1-135 | 1H-NMR (CDCl3) δ: 2.04 (3H, s), 3.62-4.07 (2H, m), 4.52 (2H, d), 5.9 (1H, m), 7.65 (5H, m) |
| 1-139 | 1H-NMR (CDCl3) δ: 1.17 (3H, t), 2.26 (2H, q), 3.63 (1H, d), 3.97 (1H, d), 4.52 (2H, d), 4.73 (2H, br s), 5.94-5.97 (1H, m), 7.43-7.46 (1H, m), 7.54-7.59 (3H, m), 7.86-7.86 (1H, m). |
| 1-140 | 1H-NMR (CDCl3) δ: 2.04 (3H, s), 3.67 (1H, d), 4.09 (1H, d), 4.52 (2H, d), 5.94-5.97 (1H, m), 7.46-7.49 (1H, m), 7.56-7.59 (1H, m), 7.81-7.85 (1H, m), 7.87-7.87 (1H, m), 7.91-7.95 (1H, m) |
| 1-141 | 1H-NMR (CDCl3) δ: 2.04 (3H, s), 3.66 (1H, d), 4.08 (1H, d), 4.51 (2H, d), 6.01-6.02 (1H, m), 7.45-7.48 (1H, m), 7.55-7.57 (1H, m), 7.66-7.69 (2H, m), 7.86-7.86 (1H, m) |
| 1-142 | 1H-NMR (CDCl3) δ: 1.17 (3H, t), 2.26 (2H, q), 3.66 (1H, d), 4.08 (1H, d), 4.52 (2H, d), 5.98-6.01 (1H, m), 7.45-7.47 (1H, m), 7.54-7.57 (1H, m), 7.66-7.69 (2H, m), 7.86-7.86 (1H, m) |
| 1-143 | 1H-NMR (CDCl3) δ: 2.04 (3H, s), 3.69 (1H, d), 4.09 (1H, d), 4.52 (2H, d), 6.00-6.03 (1H, m), 7.45-7.48 (1H, m), 7.56-7.59 (1H, m), 7.68-7.71 (1H, m), 7.73-7.77 (1H, m), 7.79-7.83 (1H, m), 7.87-7.87 (1H, m). |
| 1-144 | 1H-NMR (CDCl3) δ: 2.05 (3H, s), 3.68 (1H, d), 4.09 (1H, d), 4.51 (2H, d), 6.00-6.01 (1H, m), 7.45-7.47 (1H, m), 7.55-7.63 (2H, m), 7.78-7.79 (2H, m), 7.86-7.87 (1H, m) |
| 2-48 | 1H-NMR (CDCl3) δ: 3.68 (1H, d), 3.82 (2H, s), 3.91 (2H, s), 4.07 (1H, d), 7.26-7.29 (1H, m), 7.42-7.43 (1H, m), 7.48-7.50 (3H, m), 7.59-7.62 (1H, m), 7.69-7.72 (1H, m), 7.84-7.85 (1H, m), 8.52-8.57 (2H, m). |
| 2-49 | 1H-NMR (CDCl3) δ: 3.68 (1H, d), 3.83 (2H, s), 3.91 (2H, s), 4.07 (1H, d), 7.29-7.31 (1H, m), 7.43-7.43 (1H, m), 7.48-7.50 (4H, m), 7.60-7.63 (1H, m), 7.85-7.85 (1H, m), 8.55-8.56 (2H, m). |
| 2-50 | 1H-NMR (CDCl3) δ: 2.46 (3H, s), 3.70 (1H, d), 3.84 (2H, s), 4.08 (1H, d), 7.41-7.60 (5H, m), 7.84 (1H, s). |
| 2-51 | 1H-NMR (CDCl3) δ: 3.65-3.83 (5H, m), 7.05-7.57 (11H, m). |

TABLE 3-continued

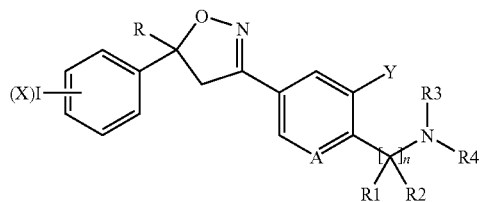

| No. | 1H-NMR |
|---|---|
| 2-52 | 1H-NMR (CDCl3) δ: 1.76 (3H, s), 1.90 (3H, s), 3.66 (1H, d), 4.05 (1H, d), 4.40 (2H, s), 7.45-7.56 (6H, m), 7.83 (1H, s). |
| 2-53 | 1H-NMR (CDCl3) δ: 3.66 (1H, d), 4.04 (1H, d), 4.87 (2H, s), 7.40-7.89 (11H, m). |
| 2-54 | 1H-NMR (CDCl3) δ: 3.65 (1H, d), 4.03 (1H, d), 4.97 (2H, s), 7.20-7.22 (1H, m), 7.43-7.54 (3H, m), 7.74-7.91 (6H, m). |
| 2-55 | 1H-NMR (CDCl3) δ: 3.76 (1H, d), 4.10 (1H, d), 5.10 (2H, s), 7.40-8.02 (11H, m). |

TABLE 4

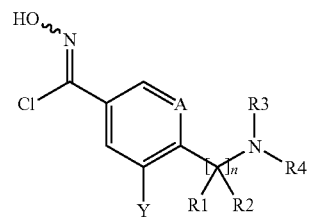
(II)

| No. | Y | R¹ | R² | R⁴ | R³ | A | n |
|---|---|---|---|---|---|---|---|
| 3-1 | H | H | H | MeCO | H | CH | 1 |
| 3-2 | Me | H | H | MeCO | H | CH | 1 |
| 3-3 | F | H | H | MeCO | H | CH | 1 |
| 3-4 | Cl | H | H | MeCO | H | CH | 1 |
| 3-5 | Br | H | H | MeCO | H | CH | 1 |
| 3-6 | I | H | H | MeCO | H | CH | 1 |
| 3-7 | NO2 | H | H | MeCO | H | CH | 1 |
| 3-8 | CN | H | H | MeCO | H | CH | 1 |
| 3-9 | MeS | H | H | MeCO | H | CH | 1 |
| 3-10 | MeSO | H | H | MeCO | H | CH | 1 |
| 3-11 | MeSO2 | H | H | MeCO | H | CH | 1 |
| 3-12 | CF3S | H | H | MeCO | H | CH | 1 |
| 3-13 | CF3S(O) | H | H | MeCO | H | CH | 1 |
| 3-14 | CF3S(O)2 | H | H | MeCO | H | CH | 1 |
| 3-15 | OCH3 | H | H | MeCO | H | CH | 1 |
| 3-16 | OCF3 | H | H | MeCO | H | CH | 1 |
| 3-17 | OH | H | H | MeCO | H | CH | 1 |
| 3-18 | SH | H | H | MeCO | H | CH | 1 |
| 3-19 | NH2 | H | H | MeCO | H | CH | 1 |
| 3-20 | NHCOMe | H | H | MeCO | H | CH | 1 |
| 3-21 | NHCO2Me | H | H | MeCO | H | CH | 1 |
| 3-22 | NHCO2CH2CCl3 | H | H | MeCO | H | CH | 1 |
| 3-23 | H | H | H | MeCO | H | CH | 2 |
| 3-24 | Br | H | H | MeCO | H | CH | 2 |
| 3-25 | Br | H | H | H | 2-pyridylCH2 | CH | 1 |
| 3-26 | Br | H | H | MeCO | 3-pyridylCH2 | CH | 1 |
| 3-27 | Br | H | H | MeCO | 4-pyridylCH2 | CH | 1 |
| 3-28 | Br | H | H | MeCO | CH3 | CH | 1 |
| 3-29 | Br | H | H | MeCO | phthalimide | CH | 1 |
| 3-30 | Br | H | H | MeCO | vinyl | CH | 1 |
| 3-31 | Br | H | H | MeCO | propargyl | CH | 1 |
| 3-32 | Br | H | H | MeCO | CH2Ph | CH | 1 |
| 3-33 | Br | H | H | MeCO | CN | CH | 1 |
| 3-34 | Br | H | H | MeCO | CH2CF3 | CH | 1 |
| 3-35 | Br | H | H | MeCO | cycloPr | CH | 1 |

TABLE 5

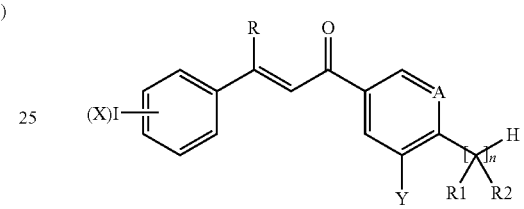
(XXII)

| No. | (X)l | R | Y | R¹ | R² | A | n |
|---|---|---|---|---|---|---|---|
| 4-1 | 3,5-diCl | CF3 | H | H | H | CH | 1 |
| 4-2 | 3,5-diCl | CF3 | Me | H | H | CH | 1 |
| 4-3 | 3,5-diCl | CF3 | F | H | H | CH | 1 |
| 4-4 | 3,5-diCl | CF3 | Cl | H | H | CH | 1 |
| 4-5 | 3,5-diCl | CF3 | Br | H | H | CH | 1 |
| 4-6 | 3,5-diCl | CF3 | I | H | H | CH | 1 |
| 4-7 | 3,5-diCl | CF3 | NO2 | H | H | CH | 1 |
| 4-8 | 3,5-diCl | CF3 | CN | H | H | CH | 1 |
| 4-9 | 3,5-diCl | CF3 | MeS | H | H | CH | 1 |
| 4-10 | 3,5-diCl | CF3 | MeSO | H | H | CH | 1 |
| 4-11 | 3,5-diCl | CF3 | MeSO2 | H | H | CH | 1 |
| 4-12 | 3,5-diCl | CF3 | CF3S | H | H | CH | 1 |
| 4-13 | 3,5-diCl | CF3 | CF3S(O) | H | H | CH | 1 |
| 4-14 | 3,5-diCl | CF3 | CF3S(O)2 | H | H | CH | 1 |
| 4-15 | 3,5-diCl | CF3 | OMe | H | H | CH | 1 |
| 4-16 | 3,5-diCl | CF3 | OCF3 | H | H | CH | 1 |
| 4-17 | 3,5-diCl | CF3 | OH | H | H | CH | 1 |
| 4-18 | 3,5-diCl | CF3 | SH | H | H | CH | 1 |
| 4-19 | 3,5-diCl | CF3 | NH2 | H | H | CH | 1 |
| 4-20 | 3,5-diCl | CF3 | NHCOMe | H | H | CH | 1 |
| 4-21 | 3,5-diCl | CF3 | NHCO2Me | H | H | CH | 1 |
| 4-22 | 3,5-diCl | CF3 | NHCO2CH2CCl3 | H | H | CH | 1 |
| 4-23 | 3,5-diBr | CF3 | Br | H | H | CH | 1 |
| 4-24 | 3,4-diCl | CF3 | Br | H | H | CH | 1 |
| 4-25 | 3,4,5-triCl | CF3 | Br | H | H | CH | 1 |
| 4-26 | 3,5-diCl-4-Me | CF3 | Br | H | H | CH | 1 |
| 4-27 | 3-F | CF3 | Br | H | H | CH | 1 |
| 4-28 | 3-Cl | CF3 | Br | H | H | CH | 1 |
| 4-29 | 3-CF3 | CF3 | Br | H | H | CH | 1 |
| 4-55 | 3-CF3 | CF3 | H | H | H | CH | 1 |
| 4-30 | 4-CF3 | CF3 | Br | H | H | CH | 1 |
| 4-31 | 3,5-diCF3 | CF3 | Br | H | H | CH | 1 |
| 4-32 | 3-NO2 | CF3 | Br | H | H | CH | 1 |
| 4-33 | 3,5-diCl | CF3 | Br | H | H | CH | 1 |
| 4-34 | 3-CH3 | CF3 | Br | H | H | CH | 1 |
| 4-35 | 3-CH3O | CF3 | Br | H | H | CH | 1 |
| 4-36 | 3-CN | CF3 | Br | H | H | CH | 1 |
| 4-37 | 3-CF3O | CF3 | Br | H | H | CH | 1 |
| 4-38 | 3-CH3S | CF3 | Br | H | H | CH | 1 |
| 4-39 | 3-CH3S(O) | CF3 | Br | H | H | CH | 1 |
| 4-40 | 3-CH3S(O)2 | CF3 | Br | H | H | CH | 1 |
| 4-41 | 3-CF3S | CF3 | Br | H | H | CH | 1 |
| 4-42 | 3-CF3S(O) | CF3 | Br | H | H | CH | 1 |
| 4-43 | 3-CF3S(O)2 | CF3 | Br | H | H | CH | 1 |

TABLE 5-continued

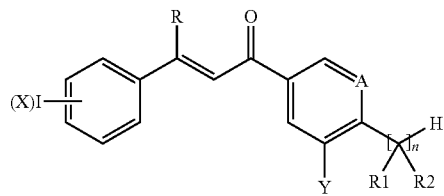

(XXII)

| No. | (X)l | R | Y | R¹ | R² | A | n |
|---|---|---|---|---|---|---|---|
| 4-44 | 3-OH | CF3 | Br | H | H | CH | 1 |
| 4-45 | 3-SH | CF3 | Br | H | H | CH | 1 |
| 4-46 | 3-NH2 | CF3 | Br | H | H | CH | 1 |
| 4-47 | 3-NHCOCH3 | CF3 | Br | H | H | CH | 1 |
| 4-48 | 3-NHCOCF3 | CF3 | Br | H | H | CH | 1 |
| 4-49 | 3-NHCO2CH3 | CF3 | Br | H | H | CH | 1 |
| 4-50 | 3-NHCO2CH2CCl3 | CF3 | Br | H | H | CH | 1 |
| 4-51 | 3-NHSO2CH3 | CF3 | Br | H | H | CH | 1 |
| 4-52 | 3-NHSO2CF3 | CF3 | Br | H | H | CH | 1 |
| 4-53 | 3,5-diCl | CF3 | Br | Me | H | CH | 1 |
| 4-54 | 3,5-diCl | CF3 | Br | H | H | N | 1 |

TABLE 6

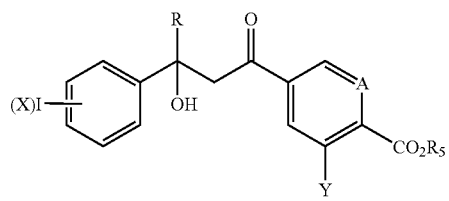

(XXVIII)

| No. | (X)l | R | Y | R⁵ | A |
|---|---|---|---|---|---|
| 5-1 | H | CF3 | H | Me | CH |
| 5-2 | 3,5-diCl | CF3 | H | Me | CH |
| 5-3 | 3,5-diCl | CF3 | Me | Me | CH |
| 5-4 | 3,5-diCl | CF3 | F | Me | CH |
| 5-5 | 3,5-diCl | CF3 | Cl | Me | CH |
| 5-6 | 3,5-diCl | CF3 | Br | Me | CH |
| 5-7 | 3,5-diCl | CF3 | I | Me | CH |
| 5-8 | 3,5-diCl | CF3 | NO2 | Me | CH |
| 5-9 | 3,5-diCl | CF3 | CN | Me | CH |
| 5-10 | 3,5-diCl | CF3 | MeS | Me | CH |
| 5-11 | 3,5-diCl | CF3 | MeSO | Me | CH |
| 5-12 | 3,5-diCl | CF3 | MeSO2 | Me | CH |
| 5-13 | 3,5-diCl | CF3 | CF3S | Me | CH |
| 5-14 | 3,5-diCl | CF3 | CF3S(O) | Me | CH |
| 5-15 | 3,5-diCl | CF3 | CF3S(O)2 | Me | CH |
| 5-16 | 3,5-diCl | CF3 | OMe | Me | CH |
| 5-17 | 3,5-diCl | CF3 | OCF3 | Me | CH |
| 5-18 | 3,5-diCl | CF3 | OH | Me | CH |
| 5-19 | 3,5-diCl | CF3 | SH | Me | CH |
| 5-20 | 3,5-diCl | CF3 | NH2 | Me | CH |
| 5-21 | 3,5-diCl | CF3 | NHCOMe | Me | CH |
| 5-22 | 3,5-diCl | CF3 | NHCO2Me | Me | CH |
| 5-23 | 3,5-diCl | CF3 | NHCO2CH2CCl3 | Me | CH |
| 5-24 | 3,5-diBr | CF3 | Br | Me | CH |
| 5-25 | 3,4-diCl | CF3 | Br | Me | CH |
| 5-26 | 3,4,5-triCl | CF3 | Br | Me | CH |
| 5-27 | 3,5-diCl-4-Me | CF3 | Br | Me | CH |
| 5-28 | 3-F | CF3 | Br | Me | CH |
| 5-29 | 3-Cl | CF3 | Br | Me | CH |
| 5-30 | 3-CF3 | CF3 | Br | Me | CH |
| 5-31 | 4-CF3 | CF3 | Br | Me | CH |
| 5-32 | 3,5-diCF3 | CF3 | Br | Me | CH |
| 5-33 | 3-NO2 | CF3 | Br | Me | CH |
| 5-34 | 3,5-diCl | CF3 | Br | Me | CH |
| 5-35 | 3-CH3 | CF3 | Br | Me | CH |
| 5-36 | 3-CH3O | CF3 | Br | Me | CH |
| 5-37 | 3-CN | CF3 | Br | Me | CH |

TABLE 6-continued

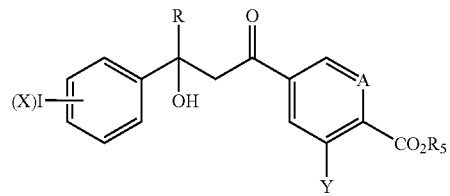

(XXVIII)

| No. | (X)l | R | Y | R⁵ | A |
|---|---|---|---|---|---|
| 5-38 | 3-CF3O | CF3 | Br | Me | CH |
| 5-39 | 3-CH3S | CF3 | Br | Me | CH |
| 5-40 | 3-CH3S(O) | CF3 | Br | Me | CH |
| 5-41 | 3-CH3S(O)2 | CF3 | Br | Me | CH |
| 5-42 | 3-CF3S | CF3 | Br | Me | CH |
| 5-43 | 3-CF3S(O) | CF3 | Br | Me | CH |
| 5-44 | 3-CF3S(O)2 | CF3 | Br | Me | CH |
| 5-45 | 3-OH | CF3 | Br | Me | CH |
| 5-46 | 3-SH | CF3 | Br | Me | CH |
| 5-47 | 3-NH2 | CF3 | Br | Me | CH |
| 5-48 | 3-NHCOCH3 | CF3 | Br | Me | CH |
| 5-49 | 3-NHCOCF3 | CF3 | Br | Me | CH |
| 5-50 | 3-NHCO2CH3 | CF3 | Br | Me | CH |
| 5-51 | 3-NHCO2CH2CCl3 | CF3 | Br | Me | CH |
| 5-52 | 3-NHSO2CH3 | CF3 | Br | Me | CH |
| 5-53 | 3-NHSO2CF3 | CF3 | Br | Me | CH |
| 5-54 | 3,5-diCl | CF3 | Br | Me | N |
| 5-55 | 3,5-diCl | CF3 | Br | Et | CH |
| 5-56 | 3,5-diCl | CF3 | Br | t-Bu | CH |

TABLE 7

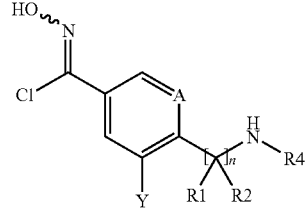

(XXX)

| No. | Y | R¹ | R² | R⁴ | A | n |
|---|---|---|---|---|---|---|
| 6-1 | H | H | H | MeCO | CH | 1 |
| 6-2 | Me | H | H | MeCO | CH | 1 |
| 6-3 | F | H | H | MeCO | CH | 1 |
| 6-4 | Cl | H | H | MeCO | CH | 1 |
| 6-5 | Br | H | H | MeCO | CH | 1 |
| 6-6 | I | H | H | MeCO | CH | 1 |
| 6-7 | NO2 | H | H | MeCO | CH | 1 |
| 6-8 | CN | H | H | MeCO | CH | 1 |
| 6-9 | MeS | H | H | MeCO | CH | 1 |
| 6-10 | MeSO | H | H | MeCO | CH | 1 |
| 6-11 | MeSO2 | H | H | MeCO | CH | 1 |
| 6-12 | CF3S | H | H | MeCO | CH | 1 |
| 6-13 | CF3S(O) | H | H | MeCO | CH | 1 |
| 6-14 | CF3S(O)2 | H | H | MeCO | CH | 1 |
| 6-15 | OCH3 | H | H | MeCO | CH | 1 |
| 6-16 | OCF3 | H | H | MeCO | CH | 1 |
| 6-17 | OH | H | H | MeCO | CH | 1 |
| 6-18 | SH | H | H | MeCO | CH | 1 |
| 6-19 | NH2 | H | H | MeCO | CH | 1 |
| 6-20 | NHCOMe | H | H | MeCO | CH | 1 |
| 6-21 | NHCO2Me | H | H | MeCO | CH | 1 |
| 6-22 | NHCO2CH2CCl3 | H | H | MeCO | CH | 1 |
| 6-23 | Br | H | H | MeCO | CH | 2 |
| 6-24 | Br | H | H | EtCO | CH | 1 |
| 6-25 | Br | H | H | n-PrCO | CH | 1 |
| 6-26 | Br | H | H | iso-PrCO | CH | 1 |
| 6-27 | Br | H | H | tert-BuCO | CH | 1 |
| 6-28 | Br | H | H | CF3CO | CH | 1 |

TABLE 7-continued

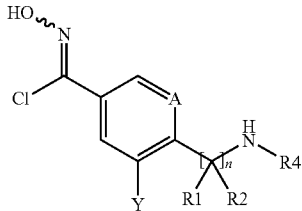

(XXX)

| No. | Y | R¹ | R² | R⁴ | A | n |
|---|---|---|---|---|---|---|
| 6-29 | Br | H | H | PhCO | CH | 1 |
| 6-30 | Br | H | H | 2-pyridylCO | CH | 1 |
| 6-31 | Br | H | H | 3-pyridylCO | CH | 1 |
| 6-32 | Br | H | H | 4-pyridylCO | CH | 1 |
| 6-33 | Br | H | H | 2-F-PhCO | CH | 1 |
| 6-34 | Br | H | H | 3-F-PhCO | CH | 1 |
| 6-35 | Br | H | H | 4-F-PhCO | CH | 1 |
| 6-36 | Br | H | H | 2-Cl-PhCO | CH | 1 |
| 6-37 | Br | H | H | 3-Cl-PhCO | CH | 1 |
| 6-38 | Br | H | H | 4-Cl-PhCO | CH | 1 |
| 6-39 | Br | H | H | 2-Br-PhCO | CH | 1 |
| 6-40 | Br | H | H | 2-Me-PhCO | CH | 1 |
| 6-41 | Br | H | H | vinylCO | CH | 1 |

TABLE 7-continued

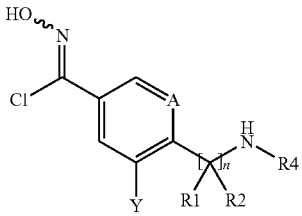

(XXX)

| No. | Y | R¹ | R² | R⁴ | A | n |
|---|---|---|---|---|---|---|
| 6-42 | Br | H | H | HCCCO | CH | 1 |
| 6-43 | Br | H | H | MeSO2 | CH | 1 |
| 6-44 | Br | H | H | CF3SO2 | CH | 1 |
| 6-45 | Br | H | H | MeHNCO | CH | 1 |
| 6-46 | Br | H | H | Me2NCO | CH | 1 |
| 6-47 | Br | H | H | MeOC(=O) | CH | 1 |
| 6-48 | Br | H | H | MeSC(=O) | CH | 1 |
| 6-49 | Br | H | H | MeCS | CH | 1 |
| 6-50 | Br | H | H | MeON(Me)CO | CH | 1 |
| 6-51 | Br | Me | H | MeCO | CH | 1 |
| 6-52 | Br | Me | H | MeCO | N | 1 |

TABLE 8

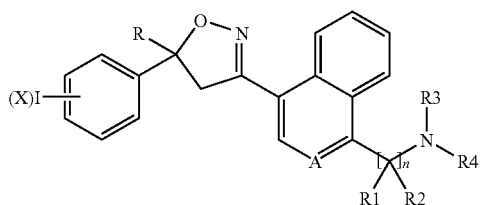

| No. | (X)l | R | R¹ | R² | R⁴ | R³ | A | n |
|---|---|---|---|---|---|---|---|---|
| 7-1 | 3,5-diCl | CF3 | H | H | MeCO | H | CH | 1 |
| 7-2 | 3,5-diCl | CF3 | H | H | MeCO | MeCO | CH | 1 |
| 7-3 | 3,5-diCl | CF3 | H | H | MeCO | 2-pyridylCO | CH | 1 |
| 7-4 | 3,5-diCl | CF3 | H | H | HCO | 2-pyridylCH2 | CH | 1 |
| 7-5 | 3,5-diCl | CF3 | H | H | MeCO | 2-pyridylCH2 | CH | 1 |
| 7-6 | 3,5-diCl | CF3 | H | H | EtCO | 2-pyridylCH2 | CH | 1 |
| 7-7 | 3,5-diCl | CF3 | H | H | Me2NCO | 2-pyridylCH2 | CH | 1 |
| 7-8 | 3,5-diCl | CF3 | H | H | MeSO2 | 2-pyridylCH2 | CH | 1 |
| 7-9 | 3,5-diCl | CF3 | H | H | 2-pyridylCO | 2-pyridylCH2 | CH | 1 |
| 7-10 | 3,5-diCl | CF3 | CN | H | MeCO | H | CH | 1 |
| 7-11 | 3,5-diCl | CF3 | CN | H | MeCO | 2-pyridylCH2 | CH | 1 |
| 7-12 | 3,5-diCl | CF3 | H | H | HCO | H | CH | 1 |
| 7-13 | 3,5-diCl | CF3 | H | H | MeCO | 3-pyridylCH2 | CH | 1 |
| 7-14 | 3,5-diCl | CF3 | H | H | MeCO | 4-pyridylCH2 | CH | 1 |
| 7-15 | 3,5-diCl | CF3 | H | H | MeCO | benzyl | CH | 1 |
| 7-16 | 3,5-diCl | CF3 | H | H | EtCO | H | CH | 1 |
| 7-17 | 3,5-diCl | CF3 | H | H | n-PrCO | H | CH | 1 |
| 7-18 | 3,5-diCl | CF3 | H | H | iso-PrCO | H | CH | 1 |
| 7-19 | 3,5-diCl | CF3 | H | H | cyclo-PrCO | H | CH | 1 |
| 7-20 | 3,5-diCl | CF3 | H | H | tert-BuCO | H | CH | 1 |
| 7-21 | 3,5-diCl | CF3 | H | H | CF3CO | H | CH | 1 |
| 7-22 | 3,5-diCl | CF3 | H | H | CF3CH2CO | H | CH | 1 |
| 7-23 | 3,5-diCl | CF3 | H | H | PhCO | H | CH | 1 |
| 7-24 | 3,5-diCl | CF3 | H | H | 2-pyridylCO | H | CH | 1 |
| 7-25 | 3,5-diCl | CF3 | H | H | 3-pyridylCO | H | CH | 1 |
| 7-26 | 3,5-diCl | CF3 | H | H | 4-pyridylCO | H | CH | 1 |

TABLE 8-continued

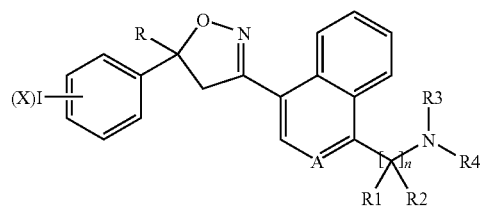

| No. | (X)l | R | R¹ | R² | R⁴ | R³ | A | n |
|---|---|---|---|---|---|---|---|---|
| 7-27 | 3,5-diCl | CF3 | H | H | 2-F-PhCO | H | CH | 1 |
| 7-28 | 3,5-diCl | CF3 | H | H | 3-F-PhCO | H | CH | 1 |
| 7-29 | 3,5-diCl | CF3 | H | H | 4-F-PhCO | H | CH | 1 |
| 7-30 | 3,5-diCl | CF3 | H | H | 2-Cl-PhCO | H | CH | 1 |
| 7-31 | 3,5-diCl | CF3 | H | H | 3-Cl-PhCO | H | CH | 1 |
| 7-32 | 3,5-diCl | CF3 | H | H | 4-Cl-PhCO | H | CH | 1 |
| 7-33 | 3,5-diCl | CF3 | H | H | 2-Br-PhCO | H | CH | 1 |
| 7-34 | 3,5-diCl | CF3 | H | H | 2-Me-PhCO | H | CH | 1 |
| 7-35 | 3,5-diCl | CF3 | H | H | vinylCO | H | CH | 1 |
| 7-36 | 3,5-diCl | CF3 | H | H | HCCCO | H | CH | 1 |
| 7-37 | 3,5-diCl | CF3 | H | H | MeSO2 | H | CH | 1 |
| 7-38 | 3,5-diCl | CF3 | H | H | CF3SO2 | H | CH | 1 |
| 7-39 | 3,5-diCl | CF3 | H | H | MeHNCO | H | CH | 1 |
| 7-40 | 3,5-diCl | CF3 | H | H | Me2NCO | H | CH | 1 |
| 7-41 | 3,5-diCl | CF3 | H | H | MeOC(=O) | H | CH | 1 |
| 7-42 | 3,5-diCl | CF3 | H | H | MeSC(=O) | H | CH | 1 |
| 7-43 | 3,5-diCl | CF3 | H | H | MeCS | H | CH | 1 |
| 7-44 | 3,5-diCl | CF3 | H | H | MeON(Me)CO | H | CH | 1 |
| 7-45 | 3,5-diCl | CF3 | H | H | MeCO | Me | CH | 1 |
| 7-46 | 3,5-diCl | CF3 | H | H | MeCO | Et | CH | 1 |
| 7-47 | 3,5-diCl | CF3 | H | H | MeCO | vinyl | CH | 1 |
| 7-48 | 3,5-diCl | CF3 | H | H | MeCO | propargyl | CH | 1 |
| 7-49 | 3,5-diCl | CF3 | H | H | MeCO | CH2Ph | CH | 1 |
| 7-50 | 3,5-diCl | CF3 | H | H | MeCO | CN | CH | 1 |
| 7-51 | 3,5-diCl | CF3 | H | H | MeCO | CH2CF3 | CH | 1 |
| 7-52 | 3,5-diCl | CF3 | H | H | MeCO | cycloPr | CH | 1 |
| 7-53 | 3,5-diCl | CF3 | H | H | C(O)CH2CH2CH2 | | CH | 1 |
| 7-54 | 3,5-diCl | CF3 | H | H | N-Me-tetrazoinone | | CH | 1 |
| 7-55 | 3,5-diCl | CF3 | H | H | N-nitroimidazolidin-2-imine | | CH | 1 |
| 7-56 | 3,5-diCl | CF3 | Me | H | MeCO | H | CH | 1 |
| 7-57 | 3,5-diCl | CF3 | Me | Me | MeCO | H | CH | 1 |
| 7-58 | 3,5-diCl | CF3 | cyclo-Pr | H | MeCO | H | CH | 1 |
| 7-59 | 3,5-diCl | CF3 | CF3 | H | MeCO | H | CH | 1 |
| 7-60 | 3,5-diCl | CF3 | CO2Me | H | MeCO | H | CH | 1 |
| 7-61 | 3,5-diCl | CF3 | CH=CH2 | H | MeCO | H | CH | 1 |
| 7-62 | 3,5-diCl | CF3 | CCH | H | MeCO | H | CH | 1 |
| 7-63 | 3,5-diCl | CF3 | CH2CH2 | | MeCO | H | CH | 1 |
| 7-64 | 3,5-diCl | CF3 | H | H | MeCO | NH2 | CH | 1 |
| 7-65 | 3,5-diCl | CF3 | H | H | MeCO | NHCOMe | CH | 1 |
| 7-66 | 3,5-diCl | CF3 | H | H | MeCO | N=CMe2 | CH | 1 |
| 7-67 | 3,5-diCl | CF3 | H | H | MeCO | OH | CH | 1 |
| 7-68 | 3,5-diCl | CF3 | H | H | MeCO | MeO | CH | 1 |
| 7-69 | 3,4-diCl | CF3 | H | H | MeCO | H | CH | 1 |
| 7-70 | 3,4,5-triCl | CH3 | H | H | MeCO | H | CH | 1 |
| 7-71 | 3,4,5-triCl | CH3 | H | H | cyclo-PrCO | H | CH | 1 |
| 7-72 | 3,4,5-triCl | CH3 | H | H | CF3CH2CO | H | CH | 1 |
| 7-73 | 3,5-diCl-4-Me | CH3 | H | H | MeCO | H | CH | 1 |
| 7-74 | 3-F | CH3 | H | H | MeCO | H | CH | 1 |
| 7-75 | 3-Cl | CF3 | H | H | MeCO | H | CH | 1 |
| 7-76 | 3-CF3 | CF3 | H | H | MeCO | H | CH | 1 |
| 7-77 | 4-CF3 | CF3 | H | H | MeCO | H | CH | 1 |
| 7-78 | 3,5-diCF3 | CF3 | H | H | MeCO | H | CH | 1 |
| 7-79 | 3-NO2 | CF3 | H | H | MeCO | H | CH | 1 |
| 7-80 | 3,5-diCl | CF3 | H | H | MeCO | H | N | 1 |
| 7-81 | 3-CH3 | CF3 | H | H | MeCO | H | CH | 1 |
| 7-82 | 3-CH3O | CF3 | H | H | MeCO | H | CH | 1 |
| 7-83 | 3-CN | CF3 | H | H | MeCO | H | CH | 1 |
| 7-84 | 3-CF3O | CF3 | H | H | MeCO | H | CH | 1 |
| 7-85 | 3-CH3S | CF3 | H | H | MeCO | H | CH | 1 |
| 7-86 | 3-CH3S(O) | CF3 | H | H | MeCO | H | CH | 1 |
| 7-87 | 3-CH3S(O)2 | CF3 | H | H | MeCO | H | CH | 1 |
| 7-88 | 3-CF3S | CF3 | H | H | MeCO | H | CH | 1 |
| 7-89 | 3-CF3S(O) | CF3 | H | H | MeCO | H | CH | 1 |
| 7-90 | 3-CF3S(O)2 | CF3 | H | H | MeCO | H | CH | 1 |
| 7-91 | 3-OH | CF3 | H | H | MeCO | H | CH | 1 |
| 7-92 | 3-SH | CF3 | H | H | MeCO | H | CH | 1 |
| 7-93 | 3-NH2 | CF3 | H | H | MeCO | H | CH | 1 |

TABLE 8-continued

| No. | (X)l | R | R¹ | R² | R⁴ | R³ | A | n |
|---|---|---|---|---|---|---|---|---|
| 7-94 | 3-NHCOCH3 | CF3 | H | H | MeCO | H | CH | 1 |
| 7-95 | 3-NHCOCF3 | CF3 | H | H | MeCO | H | CH | 1 |
| 7-96 | 3-NHCO2CH3 | CF3 | H | H | MeCO | H | CH | 1 |
| 7-97 | 3-NHCO2CH2CCl3 | CF3 | H | H | MeCO | H | CH | 1 |
| 7-98 | 3-NHSO2CH3 | CF3 | H | H | MeCO | H | CH | 1 |
| 7-99 | 3-NHSO2CF3 | CF3 | H | H | MeCO | H | CH | 1 |
| 7-100 | 3,5-diCl | CF3 | H | H | MeCO | H | CH | 2 |
| 7-101 | 3,5-diBr | CF3 | H | H | MeCO | H | CH | 1 |
| 7-102 | 3,5-diBr | CF3 | H | H | EtCO | H | CH | 1 |
| 7-103 | 3,4,5-triCl | CF3 | H | H | MeCO | H | CH | 1 |
| 7-104 | 3,4,5-triCl | CF3 | H | H | EtCO | H | CH | 1 |
| 7-105 | 3,4,5-triCl | CF3 | H | H | CF3CH2CO | H | CH | 1 |
| 7-106 | 3,4,5-triF | CF3 | H | H | MeCO | H | CH | 1 |
| 7-107 | 3,4,5-triF | CF3 | H | H | EtCO | H | CH | 1 |
| 7-108 | 3,4,5-triBr | CF3 | H | H | MeCO | H | CH | 1 |
| 7-109 | 3,4,5-triBr | CF3 | H | H | EtCO | H | CH | 1 |
| 7-110 | 3,5-diCl, 4-Br | CF3 | H | H | MeCO | H | CH | 1 |
| 7-111 | 3,5-diCl, 4-Br | CF3 | H | H | EtCO | H | CH | 1 |
| 7-112 | 3,5-diBr, 4-Cl | CF3 | H | H | MeCO | H | CH | 1 |
| 7-113 | 3,5-diBr, 4-Cl | CF3 | H | H | EtCO | H | CH | 1 |
| 7-114 | 3,5-diCl, 4-I | CF3 | H | H | MeCO | H | CH | 1 |
| 7-115 | 3,5-diCl, 4-I | CF3 | H | H | EtCO | H | CH | 1 |
| 7-116 | 3,5-diI | CF3 | H | H | MeCO | H | CH | 1 |
| 7-117 | 3,5-diI | CF3 | H | H | EtCO | H | CH | 1 |
| 7-118 | 3,5-diCl, 4-NH2 | CF3 | H | H | MeCO | H | CH | 1 |
| 7-119 | 3,5-diCl, 4-NH2 | CF3 | H | H | EtCO | H | CH | 1 |
| 7-120 | 3,5-diBr, 4-NH2 | CF3 | H | H | MeCO | H | CH | 1 |
| 7-121 | 3,5-diBr, 4-NH2 | CF3 | H | H | EtCO | H | CH | 1 |
| 7-122 | 3,5-diI, 4-NH2 | CF3 | H | H | MeCO | H | CH | 1 |
| 7-123 | 3,5-diI, 4-NH2 | CF3 | H | H | EtCO | H | CH | 1 |
| 7-124 | 3,5-diCl, 4-NHAc | CF3 | H | H | MeCO | H | CH | 1 |
| 7-125 | 3,5-diCl, 4-NHAc | CF3 | H | H | EtCO | H | CH | 1 |
| 7-126 | 3,5-diCl, 4-NHCOCF3 | CF3 | H | H | MeCO | H | CH | 1 |
| 7-127 | 3,5-diCl, 4-NHCOCF3 | CF3 | H | H | EtCO | H | CH | 1 |
| 7-128 | 3,4-diCl, 5-CF3 | CF3 | H | H | MeCO | H | CH | 1 |
| 7-129 | 3,4-diCl, 5-CF3 | CF3 | H | H | EtCO | H | CH | 1 |
| 7-130 | 3,5-diCl, 4-CF3 | CF3 | H | H | MeCO | H | CH | 1 |
| 7-131 | 3,5-diCl, 4-CF3 | CF3 | H | H | EtCO | H | CH | 1 |
| 7-132 | 3-Cl, 5-CF3 | CF3 | H | H | MeCO | H | CH | 1 |
| 7-133 | 3-Cl, 5-CF3 | CF3 | H | H | EtCO | H | CH | 1 |
| 7-134 | 3-Cl, 4-CF3 | CF3 | H | H | MeCO | H | CH | 1 |
| 7-135 | 3-Cl, 4-CF3 | CF3 | H | H | EtCO | H | CH | 1 |
| 7-136 | 3-Br, 5-CF3 | CF3 | H | H | MeCO | H | CH | 1 |
| 7-137 | 3-Br, 5-CF3 | CF3 | H | H | EtCO | H | CH | 1 |
| 7-138 | 3-Br, 4-CF3 | CF3 | H | H | MeCO | H | CH | 1 |
| 7-139 | 3-Br, 4-CF3 | CF3 | H | H | EtCO | H | CH | 1 |
| 7-140 | 3-I, 5-CF3 | CF3 | H | H | MeCO | H | CH | 1 |
| 7-141 | 3-I, 5-CF3 | CF3 | H | H | EtCO | H | CH | 1 |
| 7-142 | 3-CF3, 4-F | CF3 | H | H | MeCO | H | CH | 1 |
| 7-143 | 3-CF3, 4-F | CF3 | H | H | EtCO | H | CH | 1 |
| 7-144 | 3-Cl, 5-SCF3 | CF3 | H | H | MeCO | H | CH | 1 |
| 7-145 | 3-Cl, 5-SCF3 | CF3 | H | H | EtCO | H | CH | 1 |
| 7-146 | 4-NH2 | CF3 | H | H | MeCO | H | CH | 1 |
| 7-147 | 4-NH2 | CF3 | H | H | EtCO | H | CH | 1 |
| 7-148 | 4-NH2 | CF3 | H | H | CF3CH2CO | H | CH | 1 |
| 7-149 | 3-Cl, 4-SCF3 | CF3 | H | H | MeCO | H | CH | 1 |
| 7-150 | 3-Cl, 4-SCF3 | CF3 | H | H | EtCO | H | CH | 1 |

TABLE 9

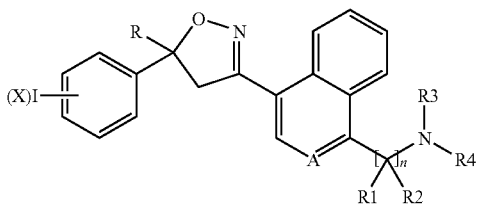

| No. | 1H-NMR |
|---|---|
| 7-1 | 1H-NMR (CDCl3) δ: 2.02 (3H, s), 3.87 (1H, d), 4.23 (1H, d), 4.83 (2H, d), 6.02-6.05 (1H, m), 7.38-7.43 (3H, m), 7.55-7.65 (4H, m), 8.00-8.02 (1H, m), 8.84-8.86 (1H, m) |
| 7-70 | 1H-NMR (CDCl3) δ: 2.03 (3H, s), 3.87 (1H, d), 4.26 (1H, d), 4.90 (2H), 5.80-5.83 (1H, m), 7.43-7.46 (2H, m), 7.61-7.69 (4H, m), 8.05-8.07 (1H, m), 8.86-8.88 (1H, m) |
| 7-128 | 1H-NMR (CDCl3) δ: 2.15 (3H, s), 3.89 (1H, d), 4.30 (1H, d), 4.88 (2H, d), 5.97-6.00 (1H, m), 7.42-7.44 (2H, m), 7.61-7.66 (2H, m), 7.87-7.91 (1H, m), 8.01-8.05 (2H, m), 8.84-8.88 (1H, m) |

BIOLOGICAL TEST EXAMPLE 1

Test Against Larva of Spodoptera litura

Solvent: Dimethylformamide 3 parts by weight
Emulsifier: Polyoxyethylene alkyl phenyl ether 1 part by weight To prepare an appropriate formulation of an active compound, 1 part by weight of the active compound was mixed with the aforementioned amount of the solvent containing the aforementioned amount of the emulsifier, and the mixture was diluted to a prescribed concentration with water.

Leaves of sweet potato were soaked in the test agent diluted to a prescribed concentration with water, air-dried, and placed in a dish of 9 cm in diameter. Into this dish, 10 larvae of Spodoptera litura at the third instar were released and kept in a room at constant temperature of 25° C. After 2 and 4 days, more leaves of sweet potato were added, and the number of dead larvae after 7 days was counted to calculate the death rate. In this test, the test results are presented as an average of the results of two dishes per section.

The compounds according to the invention Nos. 1-1, 1-2, 1-4, 1-6, 1-11, 1-12, 1-13, 1-15, 1-16, 1-17, 1-19, 1-20, 1-21, 1-23, 1-24, 1-25, 1-26, 1-27, 1-28, 1-31, 1-32, 1-34, 1-35, 1-36, 1-38, 1-40, 1-41, 1-43, 1-44, 1-46, 1-56, 1-57, 1-58, 1-59, 1-60, 1-61, 1-62, 1-63, 1-90, 1-94, 1-97, 1-98, 1-99, 1-100 and 1-101 showed 100% of death rate at a concentration of 100 ppm of the active compound.

BIOLOGICAL TEST EXAMPLE 2

Test Against Tetranychus urticae (Spraying Test)

| Solvent: | Dimethylformamide 3 parts by weight |
|---|---|
| Emulsifier: | Polyoxyethylene alkyl phenyl ether 1 part by weight |

To prepare an appropriate formulation of an active compound, 1 part by weight of the active compound was mixed with the aforementioned amount of the solvent containing the aforementioned amount of the emulsifier, and the mixture was diluted to a prescribed concentration with water.

50 to 100 adult mites of Tetranychus urticae were inoculated to leaves of kidney bean at two-leaf stage planted in a pot of 6 cm in diameter. One day after, an ample amount of the diluted aqueous solution of the prescribed concentration of an active compound was sprayed with a spray gun. After the spraying, the pot was kept in a greenhouse for 7 days, and the acaricidal rate was calculated using the following evaluation citeriae:

| Acaricidal rate | |
|---|---|
| 100 | all mites inoculated are dead |
| 98 | 1 to 4 mites survived/propagated |
| 90 | 5 to 20 mites survived/propagated |
| 60 | Many mites survived/propagated, but less than the untreated control, some dead bodies are observed |
| 0 | No difference from the untreated control was observed |

The compounds according to the invention Nos. 1-1, 1-2, 1-6, 1-11, 1-12, 1-13, 1-15, 1-16, 1-17, 1-19, 1-20, 1-21, 1-24, 1-26, 1-27, 1-28, 1-31, 1-33, 1-34, 1-35, 1-36, 1-38, 1-40, 1-41, 1-44, 1-46, 1-57, 1-58, 1-59, 1-61, 1-62, 1-63, 1-90, 1-93, 1-94, 1-99, 1-101 and 1-102 showed more than an acaricidal rate of 98 at a concentration of 100 ppm of the active compound.

BIOLOGICAL TEST EXAMPLE 3

Test Against Aulacophora femoralis

| Solvent: | Dimethylformamide 3 parts by weight |
|---|---|
| Emulsifier: | Polyoxyethylene alkyl phenyl ether 1 part by weight |

To prepare an appropriate formulation of an active compound, 1 part by weight of the active compound was mixed with the aforementioned amount of the solvent containing the aforementioned amount of the emulsifier, and the mixture was diluted to a prescribed concentration with water.

Leaves of cucumbers were soaked in a diluted aqueous solution of the prescribed concentration of an active compound prepared in the same manner as in the aforementioned tests, air-dried, and placed a plastic cup containing sterilized black soil. Into this cup, 5 larvae of Aulacophora femoralis at second instar were then released. After 7 days, the number of dead larvae was counted to calculate the death rate.

The compounds according to the invention Nos. 1-1, 1-2, 1-6, 1-11, 1-12, 1-13, 1-15, 1-16, 1-17, 1-19, 1-20, 1-21, 1-23, 1-24, 1-26, 1-27, 1-28, 1-31, 1-32, 1-33, 1-34, 1-35, 1-36, 1-38, 1-40, 1-41, 1-44, 1-46, 1-57, 1-58, 1-59, 1-60, 1-61, 1-62, 1-63, 1-93, 1-94, 1-97, 1-98, 1-99, 1-100, 1-101 1-102 and 1-106 showed 100% of death rate at a concentration of 100 ppm of the active compound.

BIOLOGICAL TEST EXAMPLE 4

Test Against Organic Phosphorus Agent- and Carbamate Agent-Resistant *Myzus persicae*

| Solvent: | Dimethylformamide 3 parts by weight |
| --- | --- |
| Emulsifier: | Polyoxyethylene alkyl phenyl ether 1 part by weight |

To prepare an appropriate formulation of an active compound, 1 part by weight of the active compound was mixed with the aforementioned amount of the solvent containing the aforementioned amount of the emulsifier, and the mixture was diluted to a prescribed concentration with water.

About 30 to 50 adults of organic phosphorus agent- and carbamate agent-resistant *Myzus persicae* per seedling were inoculated to leaves of eggplants at two leaf stage cultured in a pot of 6 cm in diameter. One day after the inoculation, an ample amount of the diluted aqueous solution of the prescribed concentration of an active compound prepared in the same manner as in the aforementioned tests was sprayed with a spray gun. After the spraying, the pot was kept in a greenhouse at 28° C. for 7 days, the death rate was calculated. The test was duplicated.

As specific examples, the compounds of the aforementioned compound Nos. 1-31 and 1-61 showed 100% of death rate at a concentration of 500 ppm of the active compound.

BIOLOGICAL TEST EXAMPLE 5-1

Test Against *Ctenocephalides felis*

| Solvent: | Dimethylformamide |
| --- | --- |

In order to prepare an appropriate formulation of an active compound, 10 mg of the active compound is dissolved in 0.5 mL of the aforementioned solvent, and the mixture is diluted to a prescribed concentration with blood from domestic animals.

About 10 to 15 adults of *Ctenocephalides felis* were kept in a flea-specific container. Another container containing the blood solution containing the compound prepared as described above was covered with a laboratory film [PARAFILM™]. The blood containing container was turned upside down and placed on the flea-specific container. This system enables *Ctenocephalides felis* to suck the blood in the container. The blood solution was kept at 37° C. and the flea-specific container was kept at room temperature. After a certain period of time, the death rate of *Ctenocephalides felis* was calculated. For this test, the death rate of 100% means death of all *Ctenocephalides felis*, while the death rate of 0% means that all the fleas survived.

In this biological test, the compound 1-64 showed more than 80% of death rate at a concentration of 100 ppm of the active ingredient.

BIOLOGICAL TEST EXAMPLE-5-2

Test Against *Ctenocephalides felis*

| Solvent: | Dimethyl Sulfoxide |
| --- | --- |

To produce a suitable preparation of active compound, 10 mg of active compound are dissolved in 0.5 ml solvent, and the concentrate is diluted with cattle blood to the desired concentration.

Approximately 10 to 15 adult unfed (Ctenocepahlides *felis*) are placed in flea chambers. The blood chamber, are sealed with parafilm on the bottom are filled with cattle blood supplied with compound solution and placed on top of the flea chamber, so that the fleas are able to suck the blood. The blood chamber is heated to 37° C. whereas the flea chamber is kept at room temperature.

After the specified period of time, mortality in % is determined. 100% means that all the fleas have been killed; 0% means that none of the fleas have been killed.

In this test for example, the following compounds from the preparation examples showed good activity of ≧80% at application rate of 100 ppm:

Example number 1-1, 1-5, 1-6, 1-12, 1-13, 1-15, 1-16, 1-19, 1-20, 1-21, 1-23, 1-24, 1-25, 1-26, 1-27, 1-28, 1-31, 1-33, 1-34, 1-35, 1-36, 1-38, 1-40, 1-41, 1-42, 1-44, 1-46, 1-57, 1-58, 1-59, 1-60, 1-61, 1-63, 1-64, 1-93, 1-94, 1-98, 1-101, 7-1, 1-128, 1-129, 1-131, 1-140, 2-2

BIOLOGICAL TEST EXAMPLE 6-1

Test Against *Boophilus microplus* (Injection)

| Solvent: | Dimethylformamide |
| --- | --- |

In order to prepare an appropriate formulation of an active compound, 10 mg of the active compound was dissolved in 0.5 mL of the aforementioned solvent, and the mixture was diluted to a prescribed concentration with water.

A solution of a compound formulated as above was injected into 5 fully fed adult female *Boophilus microplus* in their abdomen. These *Boophilus microplus* were transferred to a replica dish and kept in an incubating cabinet for a certain period of time.

After a certain period of time, the death rate of *Boophilus microplus* was calculated. In this test, the death rate of 100% means death of all *Boophilus microplus*, while the death rate of 0% means that all the mites survive.

In the above biological test, the compound 1-64 showed more than 80% of death rate at a dose of 20 ug/animal of the active ingredient.

BIOLOGICAL TEST EXAMPLE 6-2

Test Against *Boophilus microplus* (Injection)

---
Solvent: Dimethyl Sulfoxide
---

To produce a suitable preparation of active compound, 10 mg of active compound are dissolved in 0.5 ml solvent, and the concentrate is diluted with water to the desired concentration.

Five adult engorged female ticks (*Boophilus microplus*) are injected with compound solution into the abdomen. Ticks are transferred into replica plates and incubated in a climate chamber for a period of time.

After the specified period of time, mortality in % is determined. 100% means that all eggs are infertile; 0% means that all eggs are fertile.

In this test for example, the following compounds from the preparation examples showed good activity of ≧80% at application rate of 20 μg/animal:

Example number 1-1, 1-5, 1-6, 1-12, 1-13, 1-15, 1-16, 1-19, 1-20, 1-21, 1-22, 1-23, 1-24, 1-25, 1-26, 1-27, 1-28, 1-31, 1-32, 1-33, 1-34, 1-35, 1-36, 1-37, 1-38, 1-40, 1-41, 1-42, 1-43, 1-44, 1-46, 1-57, 1-58, 1-59, 1-60, 1-61, 1-63, 1-64, 1-79, 1-93, 1-94, 1-98, 1-99, 1-100, 1-101, 1-102, 1-106, 1-128, 1-129, 1-131, 1-133, 1-140, 2-2, 2-3, 2-4, 2-5, 2-6, 2-46, 2-47, 2-54, 7-1

BIOLOGICAL TEST EXAMPLE 7-1

Test Against *Lucillia cuprina*

---
Solvent: Dimethylformamide
---

In order to prepare an appropriate formulation of an active compound, 10 mg of the active compound was dissolved in 0.5 mL of the aforementioned solvent, and the mixture was diluted to a prescribed concentration with water.

About 20 to 30 larvae of *Lucillia cuprina* were placed into a test tube containing 1 cm$^3$ of minced horsemeat and 0.5 mL of an aqueous solution of a compound prepared as above.

After a certain period of time, the death rate of *Lucillia cuprina* was calculated. For this test, the death rate of 100% means death of all *Lucillia cuprina*, while the death rate of 0% means that all the flies survived.

In this biological test, the compound 1-64 showed more than 80% of death rate at a concentration of 100 ppm of the active ingredient.

BIOLOGICAL TEST EXAMPLE 7-2

Test Against *Lucillia cuprina*

---
Solvent: Dimethyl Sulfoxide
---

To produce a suitable preparation of active compound, 10 mg of active compound are dissolved in 0.5 ml solvent, and the concentrate is diluted with water to the desired concentration.

Approximately 20-30 (*Lucilia cuprina* larvae) are transferred into a test tube containing 1 cm$^3$ of minced horse meat and 0.5 ml aqueous dilution of test compound.

After the specified period of time, mortality in % is determined. 100% means that all the larvae have been killed; 0% means that none of the larvae have been killed.

In this test for example, the following compounds from the preparation examples showed good activity of ≧80% at application rate of 100 ppm:

Example number 1-1, 1-5, 1-6, 1-12, 1-13, 1-15, 1-16, 1-19, 1-20, 1-21, 1-23, 1-24, 1-25, 1-26, 1-27, 1-28, 1-31, 1-32, 1-33, 1-34, 1-35, 1-36, 1-37, 1-38, 1-40, 1-41, 1-42, 1-43, 1-44, 1-46, 1-57, 1-58, 1-59, 1-60, 1-61, 1-63, 1-64, 1-93, 1-94, 1-98, 1-101, 1-129, 1-131, 1-140, 2-2, 2-5, 2-6, 2-46, 2-47, 7-1

BIOLOGICAL TEST EXAMPLE 8-1

Test Against *Musca domestica*

---
Solvent: Dimethylformamide
---

In order to prepare an appropriate formulation of an active compound, 10 mg of the active compound was dissolved in 0.5 mL of the above solvent, and the resultant mixture was diluted to a prescribed concentration with water.

As a preparatory stage, a mixture of sugar and an aqueous solution of a compound prepared as above was absorbed into a sponge of a given size, and the sponge was place into a test container. 10 adult insects of *Musca domestica* were placed into the container, and the container was covered with a perforated cover.

After a certain period of time, the death rate of *Musca domestica* is calculated. In this test, the death rate of 100% means death of all *Musca domestica*, while the death rate of 0% means that all the flies survived.

In this biological test, the compound 1-64 showed more than 80% of death rate at a concentration of 100 ppm of the active ingredient.

BIOLOGICAL TEST EXAMPLE 8-2

Test Against *Musca domestica*

| Solvent: | Dimethyl Sulfoxide |
|---|---|

To produce a suitable preparation of active compound, 10 mg of active compound are dissolved in 0.5 ml solvent, and the concentrate is diluted with water to the desired concentration.

Prior to the assay, a piece or kitchen sponge is soaked with a mixture of sugar and compound solution and placed into a container. 10 adults (*Musca domestica*) are placed into the container and closed with a perforated lid.

After the specified period of time, mortality in % is determined. 100% means that all the flies have been killed; 0% means that none of the flies have been killed.

In this test for example, the following compounds from the preparation examples showed good activity of ≧80% at application rate of 100 ppm:

Example number 1-1, 1-6, 1-12, 1-13, 1-15, 1-16, 1-19, 1-20, 1-21, 1-23, 1-26, 1-36, 1-38, 1-40, 1-41, -42, 1-44, 1-46, 1-57, 1-58, 1-59, 1-60, 1-61, 1-63, 1-64, 1-79, 1-94, 1-99, 1-101, 1-129, 1-131, 1-140, 2-5, 7-1

BIOLOGICAL TEST EXAMPLE 9

Test Against *Boophilus microplus* (Dip)

| Solvent: | Dimethyl Sulfoxide |
|---|---|

To produce a suitable preparation of active compound, 10 mg of active compound are dissolved in 0.5 ml solvent, and the concentrate is diluted with water to the desired concentration.

Eight to ten adult engorged female *Boophilus microplus* ticks are placed in perforated plastic beakers and immersed in aqueous compound solution for one minute. Ticks are transferred to a filter paper in a plastic tray. Egg deposition of fertile eggs is monitored after seven days.

After the specified period of time, mortality in % is determined. 100% means that all the ticks have been killed; 0% means that none of the ticks have been killed.

In this test for example, the following compounds from the preparation examples showed good activity of ≧80% at application rate of 100 ppm:

Example number 1-4, 7-1, 1-12, 1-13, 1-16, 1-19, 1-20, 1-21, 1-24, 1-27, 1-28, 1-31, 1-33, 1-40, 1-41, 1-42, 1-44, 1-57, 1-58, 1-59, 1-60, 1-63, 1-64, 1-94, 1-99, 1-101, 1-129, 1-131, 1-133, 1-140

BIOLOGICAL TEST EXAMPLE 10

Test Against *Amblyomma hebraeum*

| Solvent: | Dimethyl Sulfoxide |
|---|---|

To produce a suitable preparation of active compound, 1 part by weight of active compound is mixed with the stated amount of solvent, and the concentrate is diluted with containing solvent to the desired concentration.

Nymphs of the tick *Amblyomma hebraeum* are placed in perforated plastic beakers and immersed in aqueous compound solution for one minute. Ticks are transferred to a filter paper in a Petri dish and incubated in a climate chamber for 42 days.

After the specified period of time, mortality in % is determined. 100% means that all the ticks have been killed; 0% means that none of the ticks have been killed.

In this test for example, the following compounds from the preparation examples showed good activity of ≧80% at application rate of 100 ppm:

Example number 1-13, 1-19, 1-20, 1-44, 1-58, 1-59, 1-101

BIOLOGICAL TEST EXAMPLE 11

Efficacy Against Fleas *Ctenocephalides felis Felis* (Bouché) on Cats

On study days −4 and −1 prior to treatment cats are infested with about 100 adult not fed fleas (*Ctenocephalides felis felis*). The fleas are released on the neck on the fur of the cats On study day 0 the flea infestation rate is checked by counting the fleas on the animals. The number of live fleas is recorded.

After flea counting the cats are treated with the investigational product. Cats of the control group are left untreated and serve as negative control group. The investigational veterinary product is applied dermally as one spot at a dose volume of 0.1 to 0.2 ml/kg body weight. Treatment is performed only once on study day 0. Only healthy cats are treated and included in the study.

Flea counts are performed on study days 1 and/or 2 where the cats are combed and the number of live fleas recorded. The results are documented.

In weekly intervals the cats are reinfested with about 100 adult not fed fleas per cat. One and/or two days after reinfestation the cats are combed and the live fleas counted for each animal. The results are recorded.

An active ingredient is seen as highly effective if an efficacy of >95% is achieved 24 h to 48 h after treatment and weekly reinfestation. Efficacy should be given over a three to four week period For the calculation of the effectiveness the modified Abbott formula is used:

$$\text{Efficacy \%} = \frac{\varnothing \text{ Number of fleas } CG - \varnothing \text{ Number of fleas } TG \times 100}{\varnothing \text{ Number of fleas } CG}$$

CG: Control Group

TG: Treatment Group

The active ingredient 1-129 at a dosage of 0.1 ml/kg (15 mg/kg) applied as Spot-on, was highly effective against the cat flea *Ctenocephalides felis felis*>95%.

BIOLOGICAL TEST EXAMPLE 12

Efficacy Against Ticks (*Ixodes ricinus*) on Cats

On study days −4 and/or −1 cats are sedated with a combination of the active ingredients ketaminhydrochloride and acepromazinmaleat. After all cats are sedated (approximately after 10-15 minutes) the cats are placed in single cages and 50 *Ixodes ricinus* ticks (25 female and 25 male) are released on the fur on the back of the cat. The cats are sleeping for about 1 h to 1.5 h and restrained from grooming and removing the ticks.

On study days −3 or 0 tick infestation rate is checked, while the cats are placed on an examination table. The area around the head, ears, eyes, neck and lateral and ventral part of the body and between the toes is checked intensively. The number of live attached engorged ticks is counted and recorded. Dead ticks are removed.

After tick counting on study day 0 treatment is performed. Cats of the control group are left untreated and serve as negative control group. The investigational veterinary product is applied as one single spot on the skin at the base of the skull. Treatment is performed only once on day 0. Only clinical healthy cats are enrolled into the study.

On study day 1 and/or 2 tick counts are performed and the number of life or dead attached ticks counted and recorded. On day 2 all life and dead ticks are removed.

In weekly intervals each cat is infested with 50 *Ixodes ricinus* ticks (25 female and 25 male) and tick counts are performed 1 and/or 2 days after reinfestation. Life and dead attached ticks are counted and recorded. Two days after reinfestation all ticks are removed.

An active ingredient is seen as highly effective if an efficacy of >90% is achieved 48 h after treatment and weekly reinfestation. Efficacy should be given over a three to four week period For the calculation of the effectiveness the modified Abbott formula is used:

$$\text{Efficacy \%} = \frac{\varnothing \text{ Number of fleas } CG - \varnothing \text{ Number of fleas } TG \times 100}{\varnothing \text{ Number of fleas } CG}$$

CG: Control Group

TG: Treatment Group

The active ingredient 1-129 at a dosage of 0.1 ml/kg (15 mg/kg) applied as Spot on, was highly effective against ticks *Ixodes ricinus*>90%.

FORMULATION EXAMPLE 1

Granules

To a mixture containing 10 parts of the compound of the present invention (No. 1-1), 30 parts of bentonite (montmorillonite), 58 parts of talc and 2 parts of ligninsulfonic acid salt, 25 parts of water are added, and the mixture was well kneaded and granulated with 10 to 40 mesh by an extruding granulator and dried at a temperature of from 40 to 50° C. to obtain granules.

FORMULATION EXAMPLE 2

Granules

Nintyfive (95) parts of clay mineral particles having particle diameter distribution in a range of from 0.2 to 2 mm are put into a rotary mixer. While rotating the mixer, 5 parts of the compound of the present invention (No. 1-2) are sprayed together with a liquid diluent, wetted uniformly and dried at a temperature of from 40 to 50° C. to obtain granules.

FORMULATION EXAMPLE 3

Emulsifiable Concentrate

Thirty (30) parts of the compound of the present invention (No. 1-13), 55 parts of xylene, 8 parts of polyoxyethylene alkylphenyl ether and 7 parts of calcium alkylbenzenesulfonate are mixed and stirred to obtain an emulsifiable concentrate.

FORMULATION EXAMPLE 4

Wettable Powder

Fifteen (15) parts of the compound of the present invention (No. 1-13), 80 parts of mixture of white carbon (hydrous amorphous silicon oxide fine powder) and powder clay (1:5), 2 parts of sodium alkylbenzenesulfonate and 3 parts of sodium alkylnaphthalenesulfonate-formalin-condensate are mixed together and crushed and mixed to obtain a wettable powder.

FORMULATION EXAMPLE 5

Water Dispersible Granule

Twenty (20) parts of the compound of the present invention (No. 1-1), 30 parts of sodium ligninsulfonate, 15 parts of bentonite and 35 parts of calcined diatomaceous earth are well mixed, and after addition of water, extruded with a 0.3 mm screen and dried to obtain water dispersible granules.

Industrial availability: Novel aryl isoxazoline derivatives of the present invention have an excellent insecticidal and acaricidal activity as insecticides and/or acaricides as shown herein.

The invention claimed is:

1. A compound represented by formula (I):

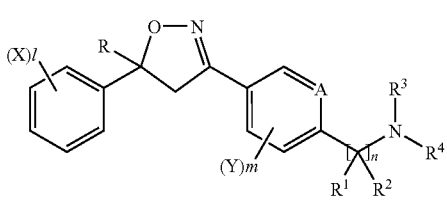

wherein
A represents C or N;
R represents alkyl or haloalkyl;
X which may be identical or different, represents halogen, haloalkyl, nitro, alkyl, alkoxy, cyano, haloalkoxy, alkylsulfinyl, alkylsulfenyl, alkylsulfonyl, haloalkylsulfinyl, haloalkylsulfenyl, haloalkylsulfonyl, amino, acylamino, alkoxycarbonylamino, haloalkylcarbonylamino, haloalkoxycarbonylamino, alkylsulfonylamino, haloalkylsulfonylamino, hydroxyl or mercapto;
Y which may be identical or different, represents halogen, haloalkyl, nitro, alkyl, alkoxy, cyano, haloalkoxy, alkylsulfinyl, alkylsulfenyl, alkylsulfonyl, haloalkylsulfinyl, haloalkylsulfenyl, haloalkylsulfonyl, hydroxyl, mercapto, amino, acylamino, alkoxycarbonylamino, haloalkylcarbonylamino, haloalkoxycarbonylamino, alkylsulfonylamino or haloalkylsulfonylamino; or two adjacent Y, together with the carbon atoms to which they are attached to, form an optionally substituted cycle;
l represents 0, 1, 2, 3, 4 or 5;
m represents 0, 1, 2, 3 or 4;
n represents 1, 2 or 3;
$R^1$ and $R^2$ each independently represent hydrogen, alkyl, optionally substituted cycloalkyl, haloalkyl, cyano, alkoxycarbonyl, alkenyl or alkynyl, or alternatively $R^1$ and $R^2$ together represent $C_{2-5}$ alkylene;
$R^3$ represents hydrogen, alkyl, optionally substituted cycloalkyl, haloalkyl, cyano, alkenyl, alkynyl, alkylcarbonyl or $CH_2$—$R^5$, wherein $R^5$ represents optionally substituted phenyl or an optionally substituted heterocyclic group; and
$R^4$ represents hydrogen, formyl, cyano, alkylcarbonyl, alkylthiocarbonyl, haloalkylcarbonyl, haloalkylthiocarbonyl, alkylaminocarbonyl, alkylaminothiocarbonyl, dialkylaminocarbonyl, dialkylaminothiocarbonyl, alkoxyaminocarbonyl, alkoxythiocarbonyl, alkoxyaminothiocarbonyl, alkoxycarbonyl, thioalkoxycarbonyl, thioalkoxythiocarbonyl,

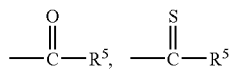

alkylsulfonyl or haloalkylsulfonyl, wherein $R^5$ is as defined above.

2. A compound according to claim 1, wherein
A represents C or N;
R represents $C_{1-6}$ alkyl or $C_{1-6}$ haloalkyl;
X which may be identical or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfinyl, $C_{1-6}$ alkylsulfenyl, $C_{1-6}$ alkylsulfonyl, $C_{1-6}$ haloalkylsulfinyl, $C_{1-6}$ haloalkylsulfenyl, $C_{1-6}$ haloalkylsulfonyl, amino, $C_{1-6}$ alkylcarbonyl, $C_{1-6}$ alkoxycarbonylamino, $C_{1-6}$ haloalkylcarbonylamino, $C_{1-6}$ haloalkoxycarbonylamino, $C_{1-6}$ alkylsulfonylamino, $C_{1-6}$ haloalkylsulfonylamino, hydroxyl or mercapto;
Y which may be identical or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfinyl, $C_{1-6}$ alkylsulfenyl, $C_{1-6}$ alkylsulfonyl, $C_{1-6}$ haloalkylsulfinyl, $C_{1-6}$ haloalkylsulfenyl, $C_{1-6}$ haloalkylsulfonyl, hydroxyl, mercapto, amino, $C_{1-4}$ alkylcarbonylamino, benzoylamino, $C_{1-6}$ alkoxycarbonylamino, $C_{1-6}$ haloalkylcarbonylamino, $C_{1-6}$ haloalkoxycarbonylamino, $C_{1-6}$ alkylsulfonylamino or $C_{1-6}$ haloalkylsulfonylamino; or two adjacent Y, together with the carbon atoms to which they are attached to, form an optionally substituted benzene;
l represents 0, 1, 2 or 3;
m represents 0, 1 or 2;
n represents 1;
$R^1$ and $R^2$ each independently represent hydrogen, $C_{1-6}$ alkyl, optionally substituted $C_{3-7}$ cycloalkyl, $C_{1-6}$ haloalkyl, cyano, $C_{1-6}$ alkoxycarbonyl, $C_{2-4}$ alkenyl or $C_{2-4}$ alkynyl, or alternatively $R^1$ and $R^2$ together represent $C_{2-5}$ alkylene;
$R^3$ represents hydrogen, $C_{1-6}$ alkyl, optionally substituted $C_{3-7}$ cycloalkyl, $C_{1-6}$ haloalkyl, cyano, $C_{2-4}$ alkenyl, $C_{2-4}$ alkynyl, $C_{1-6}$ alkylcarbonyl or $CH_2$—$R^5$, wherein $R^5$ represents optionally substituted phenyl or an optionally substituted heterocyclic group; and
$R^4$ represents formyl, cyano, $C_{1-6}$ alkylcarbonyl, $C_{1-6}$ alkylthiocarbonyl, $C_{1-6}$ haloalkylcarbonyl, $C_{1-6}$ haloalkylthiocarbonyl, $C_{1-6}$ alkylaminocarbonyl, $C_{1-6}$ alkylaminothiocarbonyl, $C_{2-8}$ (total number of carbons) dialkylaminocarbonyl, $C_{2-8}$ (total number of carbons) dialkylaminothiocarbonyl, $C_{1-6}$ alkoxyaminocarbonyl, $C_{1-6}$ alkoxythiocarbonyl, $C_{1-6}$ alkoxyaminothiocarbonyl, $C_{1-6}$ alkoxycarbonyl, thio-$C_{1-6}$ alkoxycarbonyl, thio-$C_{1-6}$ alkoxythiocarbonyl,

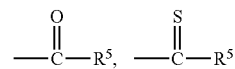

$C_{1-6}$ alkylsulfonyl or $C_{1-6}$ haloalkyl-sulfonyl, wherein $R^5$ is as defined above.

3. A composition for controlling insects, comprising the compound according to claim 1 or 2 and an extender a carrier, a surfactant, or combinations thereof.

4. Pharmaceutical composition comprising a compound according to claim 1 or 2.

5. A method for controlling animal pests, comprising applying the compound according to claim 1 to animal pests, animal habitats or a combination thereof.

6. A method of preparing a pharmaceutical composition for controlling pests on animals, comprising mixing the compound according to claim 1 with an extender, a carrier, a surfactant, or combinations thereof.

7. A method of treating a seed, comprising applying the compound according to claim 1 to the seed.

8. A method of treating a transgenic plant, comprising applying the compound according to claim 1 to the transgenic plant.

9. The compound of claim 1, wherein the compound is:

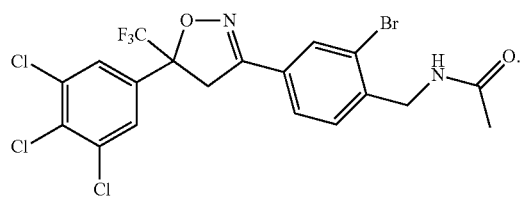 [SMILES: CC(=O)NCc1ccc(C2=NOC(c3cc(Cl)c(Cl)c(Cl)c3)(C(F)(F)F)C2)cc1Br]

* * * * *